United States Patent
Yano

(10) Patent No.: US 10,308,871 B2
(45) Date of Patent: *Jun. 4, 2019

(54) LIQUID CRYSTAL COMPOUND HAVING BENZOTHIOPHENE, LIQUID CRYSTAL COMPOSITION AND LIQUID CRYSTAL DISPLAY DEVICE

(71) Applicants: JNC CORPORATION, Tokyo (JP); JNC PETROCHEMICAL CORPORATION, Tokyo (JP)

(72) Inventor: Tomohiro Yano, Chiba (JP)

(73) Assignees: JNC CORPORATION, Tokyo (JP); JNC PETROCHEMICAL CORPORATION, Tokyo (JP)

( * ) Notice: Subject to any disclaimer, the term of this patent is extended or adjusted under 35 U.S.C. 154(b) by 64 days.

This patent is subject to a terminal disclaimer.

(21) Appl. No.: 15/547,063

(22) PCT Filed: Feb. 10, 2016

(86) PCT No.: PCT/JP2016/054004
§ 371 (c)(1),
(2) Date: Jul. 27, 2017

(87) PCT Pub. No.: WO2016/132998
PCT Pub. Date: Aug. 25, 2016

(65) Prior Publication Data
US 2018/0016501 A1 Jan. 18, 2018

(30) Foreign Application Priority Data
Feb. 19, 2015 (JP) .................................. 2015-030164

(51) Int. Cl.
G02F 1/1333 (2006.01)
C09K 19/34 (2006.01)
(Continued)

(52) U.S. Cl.
CPC ........ *C09K 19/3491* (2013.01); *C07D 333/54* (2013.01); *C07D 333/56* (2013.01); *C07D 333/64* (2013.01); *C07D 409/04* (2013.01); *C07D 409/08* (2013.01); *C07D 409/10* (2013.01); *C07D 409/12* (2013.01); *C09K 19/30* (2013.01); *C09K 19/32* (2013.01); *C09K 19/34* (2013.01); *C09K 19/42* (2013.01); *C09K 19/54* (2013.01); *C09K 19/542* (2013.01);
(Continued)

(58) Field of Classification Search
CPC .... C09K 19/3491; C09K 19/30; C09K 19/32; C09K 19/34; C09K 19/42; C09K 19/54; C09K 19/542; C09K 19/586; C09K 2019/548; G02F 1/13; G02F 1/1333; C07D 333/54; C07D 333/56; C07D 333/64; C07D 409/04; C07D 409/08; C07D 409/10; C07D 409/12

USPC .................................................... 252/299.61
See application file for complete search history.

(56) References Cited

U.S. PATENT DOCUMENTS

| 6,403,172 B1 | 6/2002 | Wingen et al. |
| 10,059,878 B2 * | 8/2018 | Saito .................. C09K 19/3491 |
| 10,100,252 B2 * | 10/2018 | Okabe ................ C09K 19/3491 |

FOREIGN PATENT DOCUMENTS

| JP | 2003509507 | 3/2000 |
| JP | 2000328062 | 11/2000 |

(Continued)

OTHER PUBLICATIONS

Registry [STN online], RN:1529477-85-7(Jan. 24, 2014), RN:1427454-19-0(Apr. 8, 2013), RN:1427437-51-1(Apr. 8, 2013), RN:1427401-28-2(Apr. 8, 2013), RN:1427327-00-1(Apr. 5, 2013), RN:1388060-95-4(Aug. 8, 2012), RN:1388034-21-6(Aug. 8, 2012),Retrieved on Jul. 6, 2017, Available at: https://scifinder.cas.org/scifinder/view/scifinder/scifinderExplore.jsf.

(Continued)

*Primary Examiner* — Geraldina Visconti
(74) *Attorney, Agent, or Firm* — JCIPRNET

(57) ABSTRACT

Provided is a liquid crystal compound that has high stability to heat, light and so forth, a high clearing point, low minimum temperature of a liquid crystal phase, small viscosity, suitable optical anisotropy, large negative dielectric anisotropy, a suitable elastic constant and excellent compatibility with other liquid crystal compounds, a liquid crystal composition containing the compound and a liquid crystal display device including the composition.

The compound is represented by formula (1).

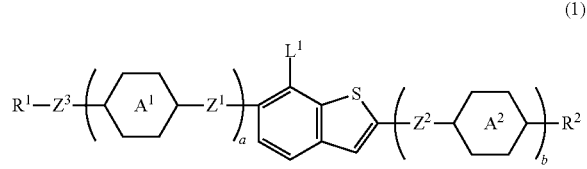

(1)

For example, $R^1$ is alkyl having 1 to 10 carbons, alkoxy having 1 to 9 carbons or alkenyl having 2 to 10 carbons; $R^2$ is alkyl having 1 to 10 carbons, alkoxy having 1 to 9 carbons or alkenyl having 3 to 10 carbons; ring $A^1$ is 1,4-cyclohexylene or 1,4-phenylene; ring $A^2$ is 1,4-cyclohexylene or 1,4-phenylene; $Z^1$ and $Z^2$ are a single bond; $Z^3$ is —O— or a single bond; and $L^1$ is F, $CF_3$ or $CF_2H$.

16 Claims, No Drawings

(51) Int. Cl.
*C07D 333/54* (2006.01)
*C07D 333/56* (2006.01)
*C09K 19/30* (2006.01)
*C09K 19/32* (2006.01)
*C09K 19/42* (2006.01)
*G02F 1/13* (2006.01)
*C07D 333/64* (2006.01)
*C07D 409/04* (2006.01)
*C07D 409/08* (2006.01)
*C07D 409/10* (2006.01)
*C07D 409/12* (2006.01)
*C09K 19/54* (2006.01)
*C09K 19/58* (2006.01)

(52) U.S. Cl.
CPC ............. *C09K 19/586* (2013.01); *G02F 1/13* (2013.01); *C09K 2019/548* (2013.01)

(56) References Cited

FOREIGN PATENT DOCUMENTS

| | | |
|---|---|---|
| JP | 2002500618 | 1/2002 |
| JP | 2004059433 | 2/2004 |
| JP | 2007518683 | 7/2007 |
| JP | 2010065049 | 3/2010 |
| JP | 2013521237 | 6/2013 |
| JP | 2014114276 | 6/2014 |
| JP | 2014129336 | 7/2014 |
| WO | 9804544 | 2/1998 |
| WO | 2014031784 | 2/2014 |
| WO | 2014130310 | 8/2014 |
| WO | 2014171272 | 10/2014 |
| WO | 2015008872 | 1/2015 |

OTHER PUBLICATIONS

Daniel Allen et al.,"An improved synthesis of substituted benzo[b]thiophenes using microwave irradiation",Tetrahedron Letters, vol. 45, No. 52, Nov. 11, 2004,pp. 9645-9647.

Nobuyuki Matsunaga et al.,"C17,20-Lyase inhibitors I. Structure-based de novo design and SAR study of C17,20-lyase inhibitors", Bioorganic & Medical Chemistry, vol. 12, No. 9, May 1, 2004, pp. 2251-2273.

Ma. Rosa Cuberes et al.,"Halogeno-Substituted 2- and 3-Methylbenzo [b] thiophenes: Use of 1H NMR Spectral Analysis and 1H{1 H} Nuclear Overhauser Effect for Locating the Halogen Substituent", Magnetic Resonance in Chemistry, vol. 23, No. 10, Oct. 1985,pp. 814-821.

Hideo Sawada et al., "Trifluoromethylation of Aromatic Compounds with Bis(Trifluoroacetyl) Peroxide", Journal of Fluorine Chemistry,vol. 46, No. 3, Mar. 1990, pp. 423-431.

Takeo Akiyama et al., "Photochemical Trifluoromethylation of Some Aromatic and Heteroaromatic Compounds with Trifluoromethyl Bromide", Bulletin of the Chemical Society of Japan, vol. 61,Oct. 1988,pp. 3531-3537.

Andrew J. Eberhart et al., "Sulfoxide-directed metal-free cross-couplings in the expedient synthesis of benzothiophene-based components of materials",Chemical Science, vol. 7, No. 2, Nov. 9, 2015, pp. 1281-1285.

"International Search Report (Form PCT/ISA/210) of PCT/JP2016/054004", dated May 10, 2016, with English translation thereof, pp. 1-8.

* cited by examiner

LIQUID CRYSTAL COMPOUND HAVING BENZOTHIOPHENE, LIQUID CRYSTAL COMPOSITION AND LIQUID CRYSTAL DISPLAY DEVICE

CROSS-REFERENCE TO RELATED APPLICATION

This application is a 371 application of International PCT application serial no. PCT/JP2016/054004, filed on Feb. 10, 2016, which claims the priority benefit of Japan application no. 2015-030164, filed on Feb. 19, 2015. The entirety of each of the abovementioned patent applications is hereby incorporated by reference herein and made a part of this specification.

TECHNICAL FIELD

The invention relates to a liquid crystal compound, a liquid crystal composition and a liquid crystal display device. More specifically, the invention relates to a compound having 7-fluoro-benzothiophene and negative dielectric anisotropy, a liquid crystal composition containing the compound, and a liquid crystal display device including the composition.

BACKGROUND ART

A liquid crystal display device has been widely used in a display of a personal computer, a television and so forth. The device utilizes optical anisotropy, dielectric anisotropy and so forth of a liquid crystal compound. As an operating mode of the liquid crystal display device, such a mode is known as a phase change (PC) mode, a twisted nematic (TN) mode, a super twisted nematic (STN) mode, a bistable twisted nematic (BTN) mode, an electrically controlled birefringence (ECB) mode, an optically compensated bend (OCB) mode, an in-plane switching (IPS) mode, a vertical alignment (VA) mode, a fringe field switching (FFS) mode and a polymer sustained alignment (PSA) mode.

Among the modes, the IPS mode, the FFS mode and the VA mode are known to improve narrowness of a viewing angle, being a disadvantage of the operating mode such as the TN mode and the STN mode. In the liquid crystal display device having the mode of the kind, a liquid crystal composition having negative dielectric anisotropy is mainly used. In order to further improve characteristics of the liquid crystal display device, a liquid crystal compound contained in the composition preferably has physical properties described in (1) to (8) below.

(1) High stability to heat, light and so forth,
(2) a high clearing point,
(3) low minimum temperature of a liquid crystal phase,
(4) small viscosity (n),
(5) suitable optical anisotropy (Δn),
(6) large negative dielectric anisotropy (Δε),
(7) a suitable elastic constant ($K_{33}$: bend elastic constant) and
(8) excellent compatibility with other liquid crystal compounds.

An effect of physical properties of the liquid crystal compound on the characteristics of the device is as described below. A compound having the high stability to heat, light and so forth as described in (1) increases a voltage holding ratio of the device. Thus, a service life of the device becomes longer. A compound having the high clearing point as described in (2) extends a temperature range in which the device can be used. A compound having the low minimum temperature of the liquid crystal phase such as the nematic phase and a smectic phase as described in (3), particular a compound having the low minimum temperature of the nematic phase, also extends the temperature range in which the device can be used. A compound having the small viscosity as described in (4) shortens a response time of the device.

A compound having suitable optical anisotropy as described in (5) improves contrast of the device. According to a design of the device, a compound having large optical anisotropy or small optical anisotropy, more specifically, a compound having the suitable optical anisotropy is required. When the response time is shortened by decreasing a cell gap of the device, a compound having large optical anisotropy is suitable. A compound having large negative dielectric anisotropy as described in (6) decreases a threshold voltage of the device. Thus, electric power consumption of the device is reduced.

With regard to (7), a compound having a large elastic constant shortens the response time of the device. A compound having a small elastic constant decreases the threshold voltage of the device. Therefore, the suitable elastic constant is required according to the characteristics that are desirably improved. A compound having the excellent compatibility with other liquid crystal compounds as described in (8) is preferred. The reason is that the physical properties of the composition are adjusted by mixing liquid crystal compounds having different physical properties.

Several liquid crystal compounds having benzothiophene skeleton have so far been prepared. Compounds (A) to (C) or the like are shown in patent literature No. 1. However, the compounds have small Δε or the like and a position of substituent on a benzothiophene ring does not optimal, and therefore the compounds are far from sufficiently suitable for use in a liquid crystal display device as a liquid crystal compound.

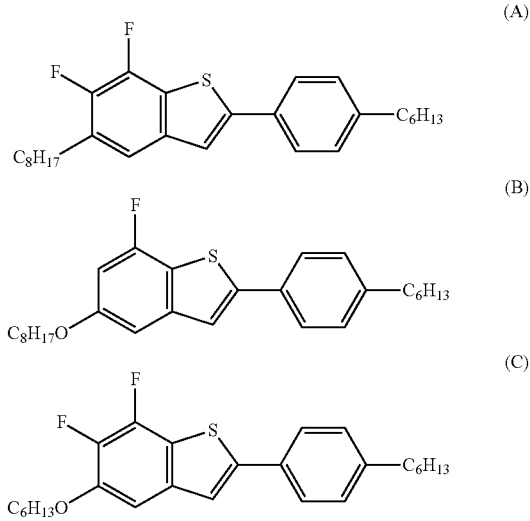

In a new compound, excellent physical properties that are not found in a conventional compound can be expected. The new compound is expected to have a suitable balance between two physical properties required upon preparing the liquid crystal composition. In view of such a situation, development has been desired for a compound having excellent physical properties and a suitable balance regarding the physical properties with regard to (1) to (8) as described above.

CITATION LIST

Patent Literature

Patent literature No. 1: JP 2000-328062 A.

SUMMARY OF INVENTION

Technical Problem

A first object of the invention is to provide high stability to heat, light and so forth, a high clearing point, low minimum temperature of a liquid crystal phase, small viscosity, suitable optical anisotropy, large negative dielectric anisotropy, a suitable elastic constant and excellent compatibility with other liquid crystal compounds. A second object is to provide a liquid crystal composition contains the compound, and has high maximum temperature of a nematic phase, low minimum temperature of the nematic phase, small viscosity, suitable optical anisotropy, large negative dielectric anisotropy, and a suitable elastic constant. The object is to provide a liquid crystal composition having a suitable balance regarding at least two of the physical properties. A third object is to provide a liquid crystal display device includes the composition, and has a wide temperature range in which the device can be used, a short response time, a large voltage holding ratio, low threshold voltage, a large contrast ratio and a long service life.

Solution to Problem

The invention concerns a compound represented by formula (1), a liquid crystal composition containing the compound, and a liquid crystal display device including the composition:

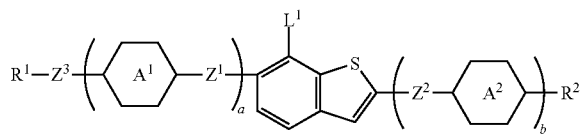

(1)

wherein, in formula (1), $R^1$ and $R^2$ are independently hydrogen, halogen or alkyl having 1 to 20 carbons, and in the alkyl, at least one piece of —$CH_2$— may be replaced by —O— or —S—, at least one piece of —$(CH_2)_2$— may replace by —CH=CH—, and in the groups, at least one piece of hydrogen may be replaced by halogen;

ring $A^1$ and ring $A^2$ are independently 1,4-cyclohexylene, 1,4-cyclohexenylene, 1,4-phenylene, tetrahydropyran-2,5-diyl, 1,3-dioxane-2,5-diyl, pyrimidine-2,5-diyl, 2,6,7-trioxabicyclo[2.2.2]octane-1,4-diyl, naphthalene-2,6-diyl or pyridine-2,5-diyl, and at least one piece of hydrogen on the rings may be replaced by halogen;

$Z^1$ and $Z^2$ are independently a single bond or alkylene having 1 to 4 carbons, in the alkylene, at least one piece of —$CH_2$— may be replaced by —O— or —COO—, and at least one piece of —$(CH_2)_2$— may replace by —CH=CH— or —C≡C—, and in the groups, at least one piece of hydrogen may be replaced by halogen;

$Z^3$ is —O— or a single bond;

$L^1$ is F, $CF_3$ or $CF_2H$; and a and b are independently 0, 1, 2, 3 or 4, and a sum of a and b is 4 or less, and when a or b is 2 or more, two of ring $A^1$ and $A^2$, and two of $Z^1$ and $Z^2$ may be identical or different.

Advantageous Effects of Invention

A first advantage of the invention is to provide a liquid crystal compound having high stability to heat, light and so forth, a high clearing point, low minimum temperature of a liquid crystal phase, small viscosity, suitable optical anisotropy, large negative dielectric anisotropy, a suitable elastic constant and excellent compatibility with other liquid crystal compounds. A second advantage is to provide a liquid crystal composition that contains the compound and has high maximum temperature of a nematic phase, low minimum temperature of the nematic phase, small viscosity, suitable optical anisotropy, large negative dielectric anisotropy and a suitable elastic constant. The object is to provide a liquid crystal composition having a suitable balance regarding at least two of the physical properties. A third advantage is to provide a liquid crystal display device that includes the composition and has a wide temperature range in which the device can be used, a short response time, a large voltage holding ratio, low threshold voltage, a large contrast ratio and a long service life.

Usage of terms herein is as described below. A liquid crystal compound is a generic term for a compound having a liquid crystal phase such as a nematic phase or a smectic phase, and also a compound having no liquid crystal phase but being useful as a component of the liquid crystal composition. The liquid crystal compound, a liquid crystal composition and a liquid crystal display device may be occasionally abbreviated as "compound," "composition" and "device," respectively. The liquid crystal display device is a generic term fora liquid crystal display panel and a liquid crystal display module. A clearing point is transition temperature between the liquid crystal phase and an isotropic phase in the liquid crystal compound. A minimum temperature of the liquid crystal phase is transition temperature between a solid and the liquid crystal phase (a smectic phase, a nematic phase or the like) in the liquid crystal compound. The maximum temperature of the nematic phase is transition temperature between the nematic phase and the isotropic phase in the liquid crystal composition, and may be occasionally abbreviated as "maximum temperature." A minimum temperature of the nematic phase may be occasionally abbreviated as "minimum temperature." A compound represented by formula (1-1) may be occasionally abbreviated as "compound (1-1)." The abbreviation may also apply occasionally to a compound represented by formula (2) or the like. In formula (1-1), formula (2) or the like, a symbol of $A^1$, $D^1$ or the like surrounded by a hexagonal shape corresponds to ring $A^1$ and ring $D^1$, respectively. A plurality of rings $A^1$ are described in one formula or indifferent formulas. In the compounds, two groups represented by two of arbitrary ring $A^1$ may be identical or different. A same rule also applies to a symbol of ring $A^2$, $Z^2$ or the like. Moreover, the same rule also applies to two of ring $A^1$ when 1 is 2. An amount of a compound expressed in terms of "percentage" is expressed in terms of "weight percent (% by weight)" based on the total amount of the composition.

An expression "at least one piece of "A" may be replaced by "B"" means that, when the number of "A" is 1, a position of "A" is arbitrary, and also when the number of "A" is 2 or more, positions thereof can be selected without restriction. An expression "at least one piece of A may be replaced by B, C or D" includes a case where arbitrary A is replaced by B, a case where arbitrary A is replaced by C, and a case where arbitrary A is replaced by D, and also a case where a plurality of pieces of A are replaced by at least two pieces of B, C and D. For example, "alkyl in which at least one piece of —$CH_2$— may be replaced by —O— or —CH═CH—" includes alkyl, alkenyl, alkoxy, alkoxyalkyl, alkoxyalkenyl and alkenyloxyalkyl. In addition, a case where two pieces of consecutive —$CH_2$— are replaced by —O— to form —O—O— is not preferred. In alkyl or the like, a case where —$CH_2$— of a methyl part (—$CH_2$—H) is replaced by —O— to form —O—H is not preferred, either.

Then, 2-fluoro-1,4-phenylene means two divalent groups described below. Fluorine may be leftward or rightward. A same rule applies also to an asymmetrical divalent group, such as tetrahydropyran-2,5-diyl.

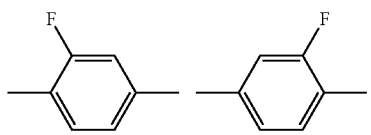

The invention includes the content described in item 1 to item 15 described below.

Item 1. A compound, represented by formula (1):

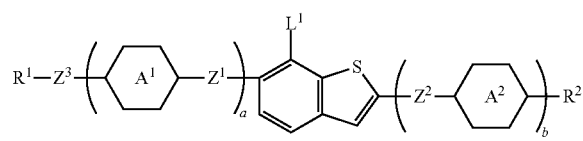

(1)

wherein, in formula (1), $R^1$ and $R^2$ are independently hydrogen, halogen or alkyl having 1 to 20 carbons, and in the alkyl, at least one piece of —$CH_2$— may be replaced by —O— or —S—, at least one piece of —$(CH_2)_2$— may replace by —CH═CH—, and in the groups, at least one piece of hydrogen may be replaced by halogen;

ring $A^1$ and ring $A^2$ are independently 1,4-cyclohexylene, 1,4-cyclohexenylene, 1,4-phenylene, tetrahydropyran-2,5-diyl, 1,3-dioxane-2,5-diyl, pyrimidine-2,5-diyl, 2,6,7-trioxabicyclo[2.2.2]octane-1,4-diyl, naphthalene-2,6-diyl or pyridine-2,5-diyl, and at least one piece of hydrogen on the rings may be replaced by halogen;

$Z^1$ and $Z^2$ are independently a single bond or alkylene having 1 to 4 carbons, in the alkylene, at least one piece of —$CH_2$— may be replaced by —O— or —COO—, and at least one piece of —$(CH_2)_2$— may replace by —CH═CH— or and in the groups, at least one piece of hydrogen may be replaced by halogen;

$Z^3$ is —O— or a single bond;

$L^1$ is F, $CF_3$ or $CF_2H$; and a and b are independently 0, 1, 2, 3 or 4, and a sum of a and b is 4 or less, and when a or b is 2 or more, two of arbitrary ring $A^1$, two of arbitrary ring $A^2$, two pieces of arbitrary $Z^1$ or two pieces of arbitrary $Z^2$ may be identical or different.

Item 2. The compound according to item 1, represented by formula (1-2):

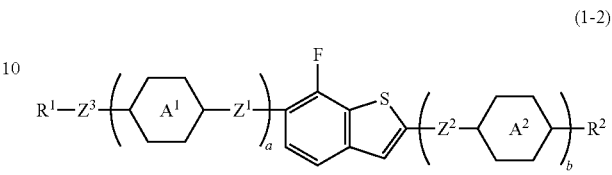

(1-2)

wherein, in formula (1-2), $R^1$ and $R^2$ are independently hydrogen, halogen or alkyl having 1 to 20 carbons, and in the alkyl, at least one piece of —$CH_2$— may be replaced by —O— or —S—, at least one piece of —$(CH_2)_2$— may replace by —CH═CH—, and in the groups, at least one piece of hydrogen may be replaced by halogen;

ring $A^1$ and ring $A^2$ are independently 1,4-cyclohexylene, 1,4-cyclohexenylene, 1,4-phenylene, tetrahydropyran-2,5-diyl, 1,3-dioxane-2,5-diyl, pyrimidine-2,5-diyl, 2,6,7-trioxabicyclo[2.2.2]octane-1,4-diyl, naphthalene-2,6-diyl or pyridine-2,5-diyl, and at least one piece of hydrogen on the rings may be replaced by halogen;

$Z^1$ and $Z^2$ are independently a single bond or alkylene having 1 to 4 carbons, in the alkylene, at least one piece of —$CH_2$— may be replaced by —O— or —COO—, and at least one piece of —$(CH_2)_2$— may replace by —CH═CH— or —C≡C—, and in the groups, at least one piece of hydrogen may be replaced by halogen;

$Z^3$ is —O— or a single bond; and a and b are independently 0, 1, 2, 3 or 4, and a sum of a and b is 4 or less, and when a or b is 2 or more, two of ring $A^1$ and $A^2$, and two of $Z^1$ and $Z^2$ may be identical or different.

Item 3. The compound according to item 2, wherein, in formula (1-2) described in item 2, $R^1$ and $R^2$ are independently chlorine, fluorine, alkyl having 1 to 10 carbons, alkoxy having 1 to 9 carbons, alkenyl having 2 to 10 carbons, polyfluoroalkyl having 1 to 10 carbons or polyfluoroalkyl having 1 to 9 carbons;

ring $A^1$ and ring $A^2$ are independently 1,4-cyclohexylene, 1,4-cyclohexenylene, 1,4-phenylene in which at least one piece of hydrogen may be replaced by halogen, or tetrahydropyran-2,5-diyl;

$Z^1$ and $Z^2$ are independently a single bond, —$(CH_2)_2$—, —CH═CH—, —CF═CF—, —C≡C—, —COO—, —OCO—, —$CF_2O$—, —$OCF_2$—, —$CH_2O$—, —$OCH_2$—, —$(CH_2)_4$—, —$(CH_2)_2CF_2O$—, —$(CH_2)_2OCF_2$—, —$CF_2O(CH_2)_2$—, —$OCF_2(CH_2)_2$—, —CH═CH—$(CH_2)_2$— or —$(CH_2)_2$—CH═CH—; and a and b are independently 0, 1, 2, 3 or 4, and a sum of a and b is 4 or less.

Item 4. The compound according to item 2 or 3, wherein, in formula (1-2), a sum of a and b is 0, 1, 2 or 3;

$R^1$ and $R^2$ are independently chlorine, fluorine, alkyl having 1 to 10 carbons, alkoxy having 1 to 9 carbons, alkenyl having 2 to 10 carbons, polyfluoroalkyl having 1 to 10 carbons or polyfluoroalkyl having 1 to 9 carbons;

ring $A^1$ and ring $A^2$ are independently 1,4-cyclohexylene, 1,4-cyclohexenylene, 1,4-phenylene in which at least one piece of hydrogen may be replaced by halogen, or tetrahydropyran-2,5-diyl; and $Z^1$ and $Z^2$ are independently a single bond, —(CH$_2$)$_2$—, —CH=CH—, —CF=CF—, —C≡C—, —COO—, —OCO—, —CF$_2$O—, —OCF$_2$—, —CH$_2$O—, —OCH$_2$—, —(CH$_2$)$_4$—, —(CH$_2$)$_2$CF$_2$O—, —(CH$_2$)$_2$OCF$_2$—, —CF$_2$O(CH$_2$)$_2$—, —OCF$_2$(CH$_2$)$_2$—, —CH=CH—(CH$_2$)$_2$— or —(CH$_2$)$_2$—CH=CH—.

(1-2)

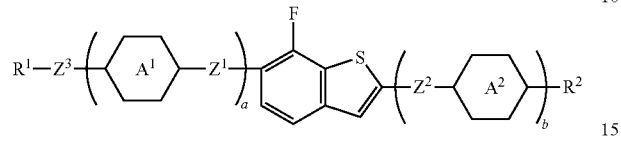

Item 5. The compound according to any one of items 1 to 4, represented by any one of formulas (1-2-1) to (1-2-10):

(1-2-1)

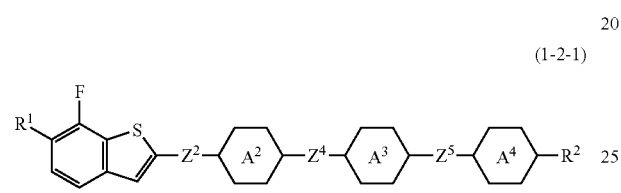

(1-2-2)

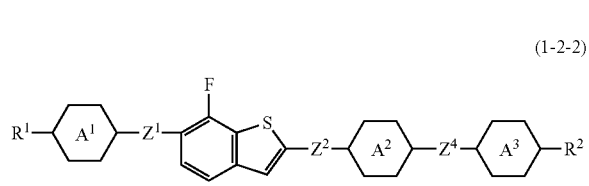

(1-2-3)

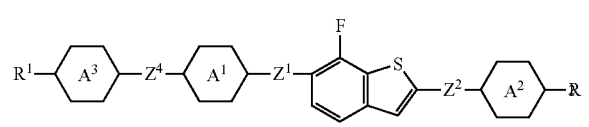

(1-2-4)

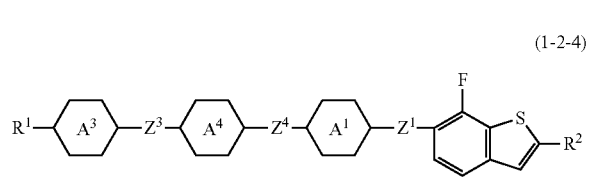

(1-2-5)

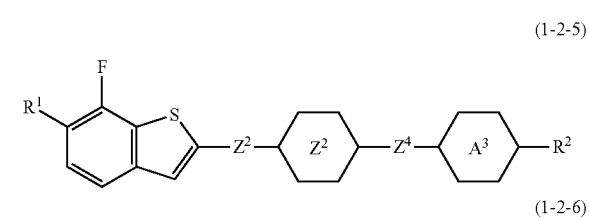

(1-2-6)

(1-2-7)

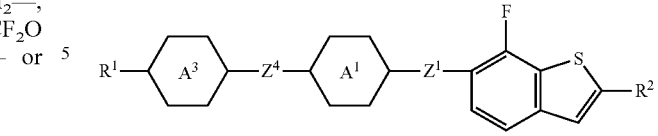

(1-2-8)

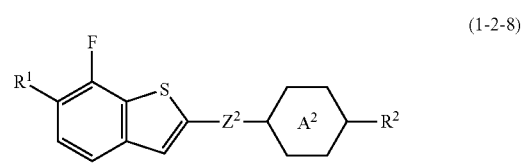

(1-2-9)

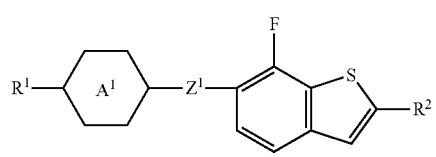

(1-2-10)

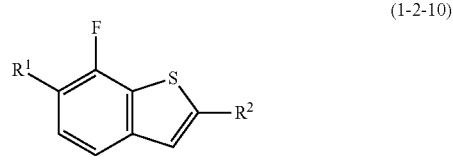

wherein, in formulas (1-2-1) to (1-2-10), $R^1$ and $R^2$ are independently chlorine, fluorine, alkyl having 1 to 10 carbons, alkoxy having 1 to 9 carbons, alkenyl having 2 to 10 carbons, polyfluoroalkyl having 1 to 10 carbons or polyfluoroalkyl having 1 to 9 carbons;

ring $A^1$, ring $A^2$, ring $A^3$ and ring $A^4$ are independently 1,4-cyclohexylene, 1,4-cyclohexenylene, 1,4-phenylene, 1,4-phenylene in which at least one piece of hydrogen is replaced by halogen, or tetrahydropyran-2,5-diyl; and $Z^1$, $Z^2$, $Z^4$ and $Z^5$ are independently a single bond, —(CH$_2$)$_2$—, —CH=CH—, —CF=CF—, —C≡C—, —COO—, —OCO—, —CF$_2$O—, —OCF$_2$—, —CH$_2$O—, —OCH$_2$—, —(CH$_2$)$_4$—, —(CH$_2$)$_2$CF$_2$O—, —(CH$_2$)$_2$OCF$_2$—, —CF$_2$O(CH$_2$)$_2$—, —OCF$_2$(CH$_2$)$_2$—, —CH=CH—(CH$_2$)$_2$— or —(CH$_2$)$_2$—CH=CH—.

Item 6. The compound according to item 5, wherein, in formulas (1-2-1) to (1-2-10) described in item 5, $R^1$ and $R^2$ are independently fluorine, alkyl having 1 to 10 carbons, alkoxy having 1 to 9 carbons, alkenyl having 2 to 10 carbons or polyfluoroalkyl having 1 to 9 carbons;

ring $A^1$, ring $A^2$, ring $A^3$ and ring $A^4$ are independently 1,4-cyclohexylene, 1,4-cyclohexenylene, 1,4-phenylene in which at least one piece of hydrogen may be replaced by halogen, or tetrahydropyran-2,5-diyl; and $Z^1$, $Z^2$, $Z^4$ and $Z^5$ are independently a single bond, —(CH$_2$)$_2$—, —CH=CH—, —CF$_2$O—, —OCF$_2$—, —CH$_2$O— or —OCH$_2$—.

Item 7. The compound according to item 6, represented by any one of formulas (1-2-4), (1-2-7) and (1-2-9):

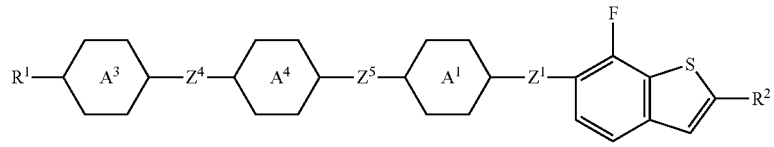
(1-2-4)

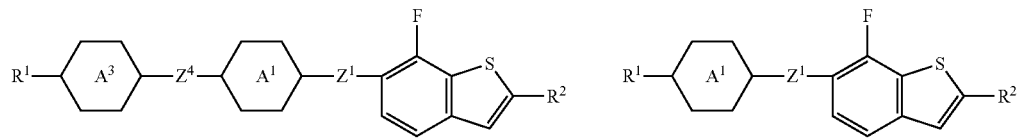
(1-2-7) (1-2-9)

Item 8. The compound according to item 6, represented by any one of formulas (1-2-1), (1-2-5), (1-2-8) and (1-2-10), wherein, $R^1$ is alkoxy having 1 to 6 carbons:

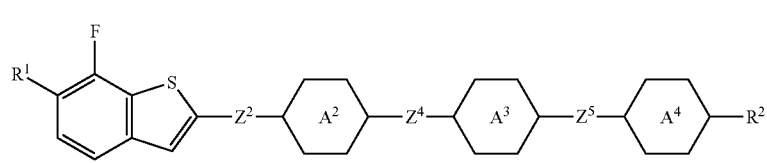
(1-2-1)

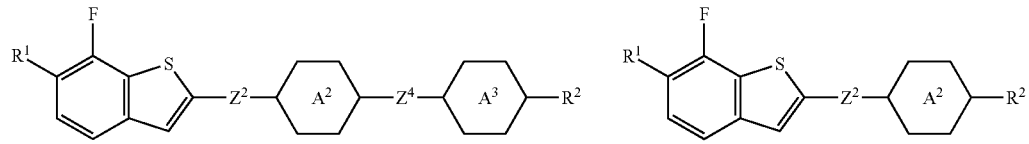
(1-2-5) (1-2-8)

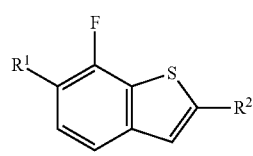
(1-2-10)

Item 9. A liquid crystal composition, containing at least one compound according to any one of items 1 to 8.

Item 10. The liquid crystal composition according to item 9, further containing at least one compound selected from the group of compounds represented by formulas (6) to (12):

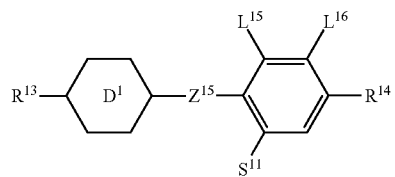
(6)

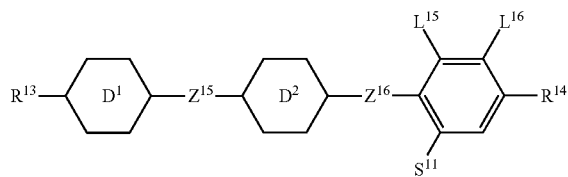
(7)

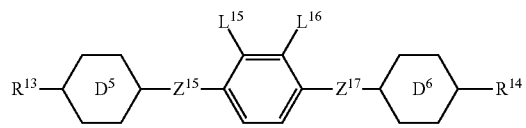
(8)

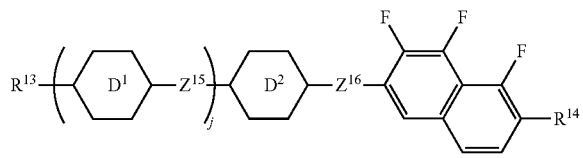
(9)

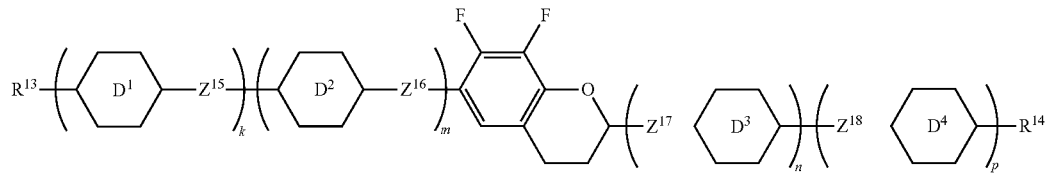

(10)

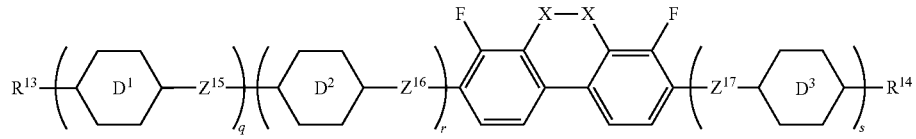

(11)

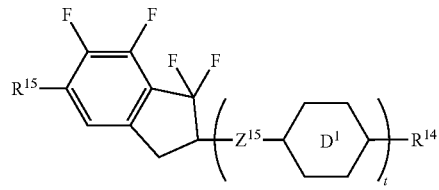

(12)

wherein in formulas (6) to (12), $R^{13}$ is alkyl having 1 to 10 carbons or alkenyl having 2 to 10 carbons, and in the alkyl and the alkenyl, at least one piece of —CH$_2$— may be replaced by —O—, and at least one piece of hydrogen may be replaced by fluorine;

$R^{14}$ is alkyl having 1 to 10 carbons, in the alkyl, at least one piece of —CH$_2$— may be replaced by —O—, and at least one piece of hydrogen may be replaced by fluorine;

$R^{15}$ is hydrogen, fluorine, alkyl having 1 to 10 carbons or alkenyl having 2 to 10 carbons, and in the alkyl and the alkenyl, at least one piece of —CH$_2$— may be replaced by —O—, and at least one piece of hydrogen may be replaced by fluorine;

$S^{11}$ is hydrogen or methyl;

X is —CF$_2$—, —O— or —CHF—;

ring $D^1$, ring $D^2$, ring $D^3$ and ring $D^4$ are independently 1,4-cyclohexylene, 1,4-cyclohexenylene, 1,4-phenylene in which at least one piece of hydrogen may be replaced by fluorine, tetrahydropyran-2,5-diyl, or decahydronaphthalene-2,6-diyl;

ring $D^5$ and ring $D^6$ are independently 1,4-cyclohexylene, 1,4-cyclohexenylene, 1,4-phenylene, tetrahydropyran-2,5-diyl or decahydronaphthalene-2,6-diyl;

$Z^{15}$, $Z^{16}$, $Z^{17}$ and $Z^{18}$ are independently a single bond, —CH$_2$CH$_2$—, —COO—, —CH$_2$O—, —OCF$_2$— or —OCF$_2$CH$_2$CH$_2$—;

$L^{15}$ and $L^{16}$ are independently fluorine or chlorine; and j, k, m, n, p, q, r and s are independently 0 or 1, a sum of k, m, n and p is 1 or 2, and a sum of q, r and s is 0, 1, 2 or 3, and t is 1, 2 or 3.

Item 11. The liquid crystal composition according to items 9 or 10, further containing at least one compound selected from the group of compounds represented by formulas (13) to (15):

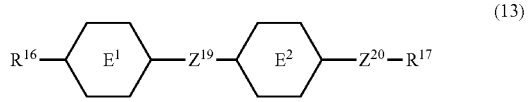

(13)

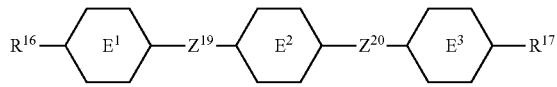

(14)

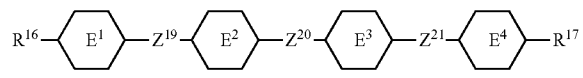

(15)

wherein in formulas (13) to (15), $R^{16}$ and $R^{17}$ are independently alkyl having 1 to 10 carbons or alkenyl having 2 to 10 carbons, and in the alkyl and the alkenyl, at least one piece of —CH$_2$— may be replaced by —O—, and at least one piece of hydrogen may be replaced by fluorine;

ring $E^1$, ring $E^2$, ring $E^3$ and ring $E^4$ are independently 1,4-cyclohexylene, 1,4-phenylene, 2-fluoro-1,4-phenylene, 2,5-difluoro-1,4-phenylene or pyrimidine-2,5-diyl; and $Z^{19}$, $Z^{20}$ and $Z^{21}$ are independently a single bond, —CH$_2$CH$_2$—, —CH=CH—, —C≡C— or —COO—.

Item 12. The liquid crystal composition according to any one of items 9 to 11, further containing at least one compound selected from the group of compounds represented by formulas (2) to (4):

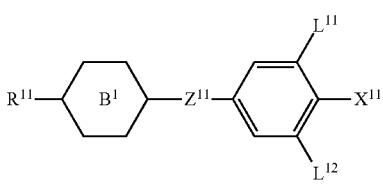

(2)

-continued

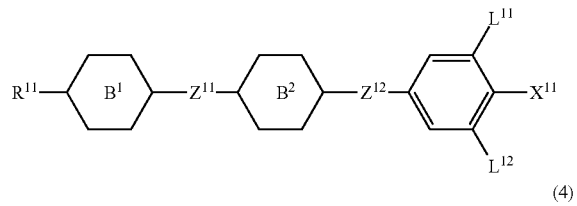

(3)

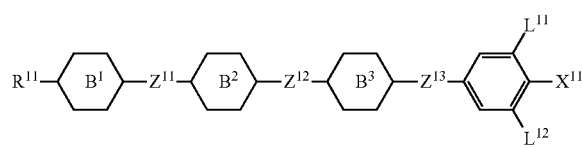

(4)

wherein in formulas (2) to (4), $R^{11}$ is alkyl having 1 to 10 carbons or alkenyl having 2 to 10 carbons, and in the alkyl and the alkenyl, at least one piece of hydrogen may be replaced by fluorine, and at least one piece of —CH$_2$— may be replaced by —O—;

$X^{11}$ is fluorine, chlorine, —OCF$_3$, —OCHF$_2$, —CF$_3$, —CHF$_2$, —CH$_2$F, —OCF$_2$CHF$_2$ or —OCF$_2$CHFCF$_3$;

ring $B^1$, ring $B^2$ and ring $B^3$ are independently 1,4-cyclohexylene, 1,4-phenylene in which at least one piece of hydrogen may be replaced by fluorine, tetrahydropyran-2,5-diyl, 1,3-dioxane-2,5-diyl, or pyrimidine-2,5-diyl;

$Z^{11}$, $Z^{12}$ and $Z^{13}$ are independently a single bond, —CH$_2$CH$_2$—, —CH=CH—, —C≡C—, —COO—, —CF$_2$O—, —OCF$_2$—, —CH$_2$O— or —(CH$_2$)$_4$—; and $L^{11}$ and $L^{12}$ are independently hydrogen or fluorine.

Item 13. The liquid crystal composition according to any one of items 9 to 12, further containing at least one optically active compound and/or at least one polymerizable compound.

Item 14. The liquid crystal composition according to any one of items 9 to 13, further containing at least one antioxidant and/or at least one ultraviolet light absorbent.

Item 15. A liquid crystal display device, including the liquid crystal composition according to any one of items 9 to 14.

Item 16. The liquid crystal display device according to item 15, wherein the liquid crystal composition according to any one of items 9 to 14 is encapsulated.

1-1. Compound (1)

Compound (1) of the invention will be described. Preferred examples of a terminal group, a ring structure and a bonding group in compound (1), and an effect of the groups on physical properties applies also to a compound represented by a subordinate formula of formula (1) for compound (1):

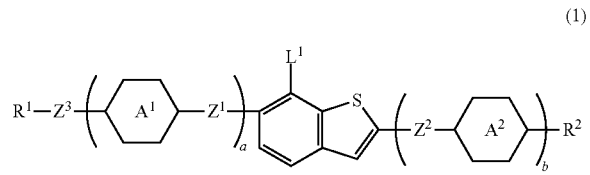

(1)

In formula (1), $R^1$ and $R^2$ are independently hydrogen, halogen or alkyl having 1 to 20 carbons, in the alkyl, at least one piece of —CH$_2$— may be replaced by —O— or —S—, and at least one piece of —(CH$_2$)$_2$— may be replace by —CH=CH—, and in the groups, at least one piece of hydrogen may be replaced by halogen. The groups have a straight chain or a branched chain, and include no cyclic group such as cyclohexyl. In the groups, the straight chain is preferred to the branched chain.

A preferred configuration of —CH=CH— in the alkenyl depends on a position of a double bond. A trans configuration is preferred in alkenyl having the double bond in an odd-numbered position, such as —CH=CHCH$_3$, —CH=CHC$_2$H$_5$, —CH=CHC$_3$H$_7$, —CH=CHC$_4$H$_9$, —C$_2$H$_4$CH=CHCH$_3$ or —C$_2$H$_4$CH=CHC$_2$H$_5$. A cis configuration is preferred in alkenyl having the double bond in an even-numbered position, such as —CH$_2$CH=CHCH$_3$, —CH$_2$CH=CHC$_2$H$_5$ or —CH$_2$CH=CHC$_3$H$_7$. An alkenyl compound having a preferred configuration has a high clearing point or a wide temperature range of the liquid crystal phase. A detailed description is found in Mol. Cryst. Liq. Cryst., 1985, 131, 109 and Mol. Cryst. Liq. Cryst., 1985, 131 and 327.

Preferred examples of $R^1$ or $R^2$ include alkyl, alkoxy, alkenyl and alkenyloxy. Further preferred examples of $R^1$ or $R^2$ include alkyl, alkoxy and alkenyl.

Specific examples of alkyl include —CH$_3$, —C$_2$H$_5$, —C$_3$H$_7$, —C$_4$H$_9$, —C$_5$H$_{11}$, —C$_6$H$_{13}$, —C$_7$H$_{15}$, —C$_8$H$_{17}$, —C$_9$H$_{19}$, —C$_{10}$H$_{21}$, —C$_{11}$H$_{23}$, —C$_{12}$H$_{25}$, —C$_{13}$H$_{27}$, —C$_{14}$H$_{29}$ and —C$_{15}$H$_{31}$.

Specific examples of alkoxy include —OCH$_3$, —OC$_2$H$_5$, —OC$_3$H$_7$, —OC$_4$H$_9$, —OC$_5$H$_{11}$, —OC$_6$H$_{13}$, —OC$_7$H$_{15}$, —OC$_8$H$_{17}$, —OC$_9$H$_{19}$, —OC$_{10}$H$_{21}$, —OC$_{11}$H$_{23}$, —OC$_{12}$H$_{25}$, —OC$_{13}$H$_{27}$ and —OC$_{14}$H$_{29}$.

Specific examples of alkoxyalkyl include —CH$_2$OCH$_3$, —CH$_2$OC$_2$H$_5$, —CH$_2$OC$_3$H$_7$, —(CH$_2$)$_2$—OCH$_3$, —(CH$_2$)$_2$—OC$_2$H$_5$, —(CH$_2$)$_2$—OC$_3$H$_7$, —(CH$_2$)$_3$—OCH$_3$, —(CH$_2$)$_4$—OCH$_3$ and —(CH$_2$)$_5$—OCH$_3$.

Specific examples of alkenyl include —CH=CH$_2$, —CH=CHCH$_3$, —CH$_2$CH=CH$_2$, —CH=CHC$_2$H$_5$, —CH$_2$CH=CHCH$_3$, —(CH$_2$)$_2$—CH=CH$_2$, —CH=CHC$_3$H$_7$, —CH$_2$CH=CHC$_2$H$_5$, —(CH$_2$)$_2$—CH=CHCH$_3$ and —(CH$_2$)$_3$—CH=CH$_2$.

Specific examples of alkenyloxy include —OCH$_2$CH=CH$_2$, —OCH$_2$CH=CHCH$_3$ and —OCH$_2$CH=CHC$_2$H$_5$.

Specific examples of alkyl in which at least one piece of hydrogen is replaced by halogen include —CH$_2$F, —CHF$_2$, —CF$_3$, —(CH$_2$)$_2$—F, —CF$_2$CH$_3$, —CF$_2$CH$_2$F, —CF$_2$CHF$_2$, —CH$_2$CF$_3$, —CF$_2$CF$_3$, —(CH$_2$)$_3$—F, —CF$_2$CH$_2$CH$_3$, —CH$_2$CHFCH$_3$, —CH$_2$CF$_2$CH$_3$, —(CF$_2$)$_3$—F, —CF$_2$CHFCF$_3$, —CHFCF$_2$CF$_3$, —(CH$_2$)$_4$—F, —CF$_2$(CH$_2$)$_2$CH$_3$, —(CF$_2$)$_4$—F, —(CH$_2$)$_5$—F, —(CF$_2$)$_5$—F, —CH$_2$Cl, —CHCl$_2$, —CCl$_3$, —(CH$_2$)$_2$—Cl, —CCl$_2$CH$_3$, —CCl$_2$CH$_2$Cl, —CCl$_2$CHCl$_2$, —CH$_2$CCl$_3$, —CCl$_2$CCl$_3$, —(CH$_2$)$_3$—Cl, —CCl$_2$CH$_2$CH$_3$, —(CCl$_2$)$_3$—Cl, —CCl$_2$CHClCCl$_3$, —CHClCCl$_2$CCl$_3$, —(CH$_2$)$_4$—Cl, —(CCl$_2$)$_4$—Cl, —CCl$_2$(CH$_2$)$_2$CH$_3$, —(CH$_2$)$_5$—Cl and —(CCl$_2$)$_5$—Cl.

Specific examples of alkoxy in which at least one piece of hydrogen is replaced by halogen include —OCH$_2$F, —OCHF$_2$, —OCF$_3$, —O—(CH$_2$)$_2$—F, —OCF$_2$CH$_2$F, —OCF$_2$CHF$_2$, —OCH$_2$CF$_3$, —O—(CH$_2$)$_3$—F, —O—(CF$_2$)$_3$—F, —OCF$_2$CHFCF$_3$, —OCHFCF$_2$CF$_3$, —O(CH$_2$)$_4$—F, —O—(CF$_2$)$_4$—F, —O—(CH$_2$)$_5$—F, —O—(CF$_2$)$_5$—F, —OCH$_2$CHFCH$_2$CH$_3$, —OCH$_2$Cl, —OCHCl$_2$, —OCCl$_3$, —O—(CH$_2$)$_2$—Cl, —OCCl$_2$CH$_2$Cl, —OCCl$_2$CHCl$_2$, —OCH$_2$CCl$_3$, —O—(CH$_2$)$_3$—Cl, —O—(CCl$_2$)$_3$—Cl, —OCCl$_2$CHClCCl$_3$, —OCHClCCl$_2$CCl$_3$, —O(CH$_2$)$_4$—Cl, —O—(CCl$_2$)$_4$—Cl, —O—(CH$_2$)$_5$—Cl and —O—(CCl$_2$)$_5$—Cl.

Specific examples of alkenyl in which at least one piece of hydrogen is replaced by halogen include —CH=CHF, —CH=CF$_2$, —CF=CHF, —CH=CHCH$_2$F, —CH=CHCF$_3$, —(CH$_2$)$_2$—CH=CF$_2$, —CH$_2$CH=CHCF$_3$, —CH=CHCF$_2$CF$_3$, —CH=CHCl, —CH=CCl$_2$, —CCl=CHCl, —CH=CHCH$_2$Cl, —CH=CHCCl$_3$, —(CH$_2$)$_2$—CH=CCl$_2$, —CH$_2$CH=CHCCl$_3$ and —CH=CHCCl$_2$CCl$_3$.

In formula (1), ring A$^1$ and ring A$^2$ are independently 1,4-cyclohexylene, 1,4-cyclohexenylene, 1,4-phenylene, tetrahydropyran-2,5-diyl, 1,3-dioxane-2,5-diyl, pyrimidine-2,5-diyl, 2,6,7-trioxabicyclo[2.2.2]octane-1,4-diyl, naphthalene-2,6-diyl or pyridine-2,5-diyl, and at least one piece of hydrogen on the rings may be replaced by halogen.

Specific examples of preferred ring A$^1$ or ring A$^2$ include 1,4-cyclohexylene, 1,4-cyclohexenylene, 1,4-phenylene, 1,4-phenylene in which at least one piece of hydrogen is replaced by fluorine, tetrahydropyran-2,5-diyl and 5,5,6,6-tetrafluoro-1,3-cyclohexadiene-1,4-diyl. Further preferred examples include 1,4-cyclohexylene, 1,4-phenylene, 1,4-phenylene in which at least one piece of hydrogen is replaced by fluorine, and tetrahydropyran-2,5-diyl. Then, 1,4-cyclohexylene has cis and trans configurations. From a viewpoint of high maximum temperature, the trans configuration is preferred.

Specific examples of preferred 1,4-phenylene in which at least one piece of hydrogen is replaced by halogen include a group represented by formulas (A-1) to (A-17). In order to have large negative dielectric anisotropy, the group represented by formulas (A-1), (A-5), (A-6), (A-7), (A-8), (A-9), (A-10) or (A-11) is further preferred.

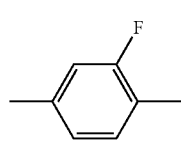
(A-1)

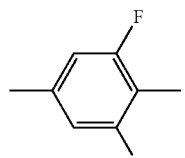
(A-2)

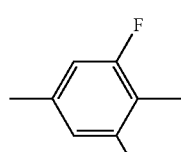
(A-3)

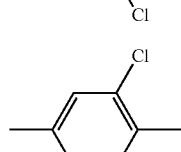
(A-4)

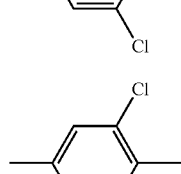
(A-5)

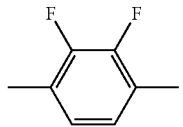
(A-6)

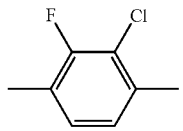
(A-7)

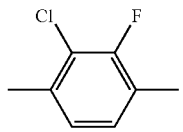
(A-8)

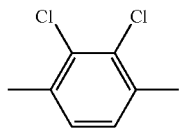
(A-9)

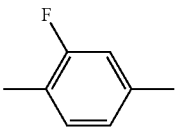
(A-10)

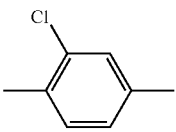
(A-11)

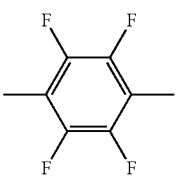
(A-12)

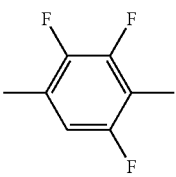
(A-13)

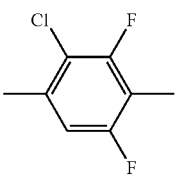
(A-14)

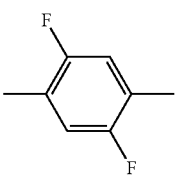
(A-15)

-continued

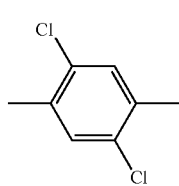
(A-16)

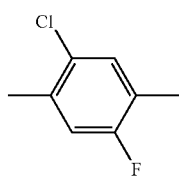
(A-17)

In formula (1), $Z^1$ and $Z^2$ are independently a single bond or alkylene having 1 to 4 carbons, in the alkylene, at least one piece of —$CH_2$— may be replaced by —O— or —COO—, and at least one piece of —$(CH_2)_2$— may replace by CH=CH— or —C≡C—, and in the groups, at least one piece of hydrogen may be replaced by halogen.

Preferred examples of $Z^1$ or $Z^2$ include a single bond, —$(CH_2)_2$—, —CH=CH—, —CF=CF—, —C≡C—, —COO—, —OCO—, —$CF_2O$—, —$OCF_2$—, —$CH_2O$—, —$OCH_2$—, —$(CH_2)_4$—, —$(CH_2)_2CF_2O$—, —$(CH_2)_2OCF_2$—, —$CF_2O(CH_2)_2$—, —$OCF_2(CH_2)_2$—, —CH=CH—$(CH_2)_2$— and —$(CH_2)_2$—CH=CH—. Further preferred examples include a single bond, —$(CH_2)_2$—, —CH=CH—, —COO—, —OCO—, —$CF_2O$—, —$OCF_2$—, —$CH_2O$— and —$OCH_2$—. Still further preferred examples include a single bond, —$(CH_2)_2$—, —$CH_2O$— and —$OCH_2$—.

In formula (1), $Z^3$ is —O— or a single bond. A compound in which $Z^3$ is —O— has large negative dielectric anisotropy, high maximum temperature and large refractive index anisotropy, and therefore such a compound is preferred. A compound in which $Z^3$ is a single bond has small viscosity, and therefore such a compound is preferred.

In formula (1), a and b are independently 0, 1, 2, 3 or 4, and a sum of a and b is 4 or less. If the compatibility with other liquid crystal compounds is taken into consideration, a compound in which a sum of a and b is 3 or less is preferred. When a sum of a and b is 1 or 0, the viscosity is small. When a sum of a and b is 2, balance regarding the viscosity and the maximum temperature is excellent. When a sum of a and b is 3, the maximum temperature is high.

In formula (1), $L^1$ is F, $CF_3$ or $CF_2H$, when $L^1$ is $CF_3$ or $CF_2H$, the dielectric anisotropy is large, and when $L^1$ is F, balance regarding the characteristics is good.

Compound (1) has a 7-$L^1$, 2,6-di-substituented benzothiophene skeleton. Due to an effect of such structure, the compound has a high clearing point, low minimum temperature of a liquid crystal phase, small viscosity, suitable optical anisotropy, large negative dielectric anisotropy, a suitable elastic constant and excellent compatibility with other liquid crystal compounds. Compound (1) is superb in the characteristics in comparison with a benzothiophene compound in which $L^1$ in 7-position and substituents in 2-position and 6-position of the benzothiophene skeleton are substituted in other positions.

As described above, a compound having objective physical properties can be obtained by suitably selecting kinds of the terminal groups, the ring structures, the bonding groups and so forth. Compound (1) may contain a larger amount of isotope such as $^2H$ (deuterium) and $^{13}C$ than the amount of natural abundance because no significant difference exists in the physical properties of the compound.

1-2. Preferred Compound

Preferred examples of compound (1) include compounds (1-2-1) to (1-2-10). Further preferred examples of compound (1) include the compound described in item 6 and item 7.

(1-2-1)

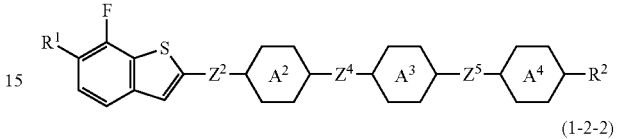
(1-2-2)

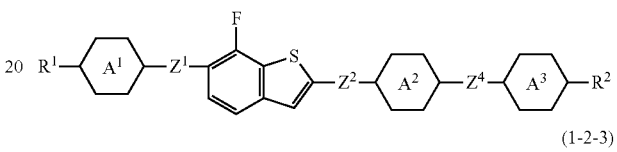
(1-2-3)

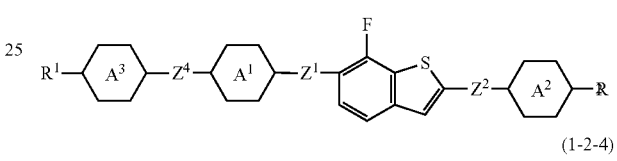
(1-2-4)

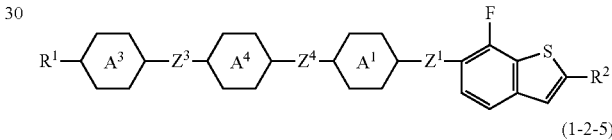
(1-2-5)

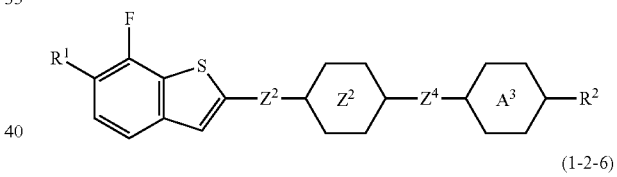
(1-2-6)

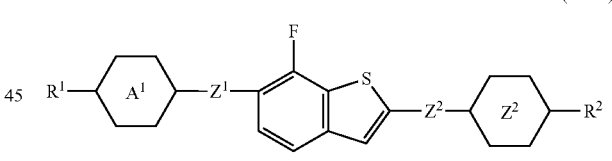
(1-2-7)

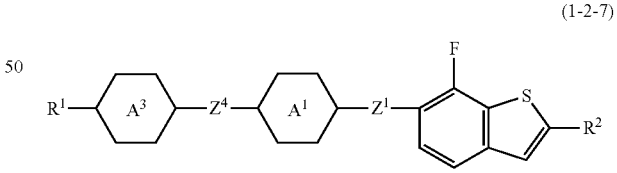
(1-2-8)

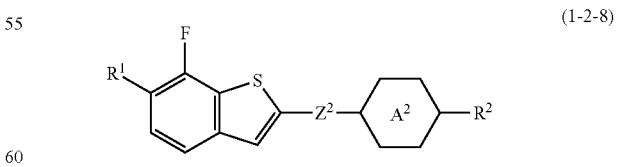
(1-2-9)

(1-2-10)

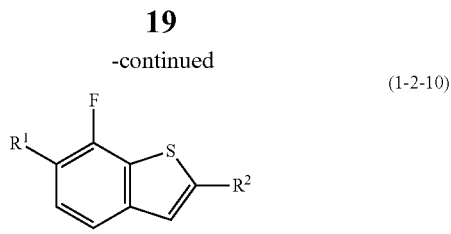

Preferred examples of ring $A^3$ and ring $A^4$ in compounds (1-2-1) to (1-2-10), and an effect of the groups on physical properties are similar to the preferred examples and the effect of ring $A^1$ and ring $A^2$ in formula (1). Then, preferred examples of $Z^4$ and $Z^5$, and the effect of the groups on physical properties are similar to the preferred examples and the effect of $Z^1$ and $Z^2$ in formula (1).

1-3. Synthesis of Compound (1)

A method for synthesizing compound (1) will be described. Compound (1) can be prepared by suitably combining techniques in synthetic organic chemistry. Methods for introducing an objective terminal group, ring and bonding group into a starting material are described in books such as "Organic Syntheses" (John Wiley & Sons, Inc.), "Organic Reactions" (John Wiley & Sons, Inc.), "Comprehensive Organic Synthesis" (Pergamon Press) and "New Experimental Chemistry Course (Shin Jikken Kagaku Koza in Japanese)" (Maruzen Co., Ltd.).

1-3-1. Formation of a Bonding Group

An example of a method for forming a bonding group in compound (1) is as described in a scheme below. In the scheme, MSG1 (or MSG2) is a monovalent organic group having at least one ring. Monovalent organic groups represented by a plurality of MSG1 (or MSG2) may be identical or different. Compounds (1A) to (1D) correspond to compound (1).

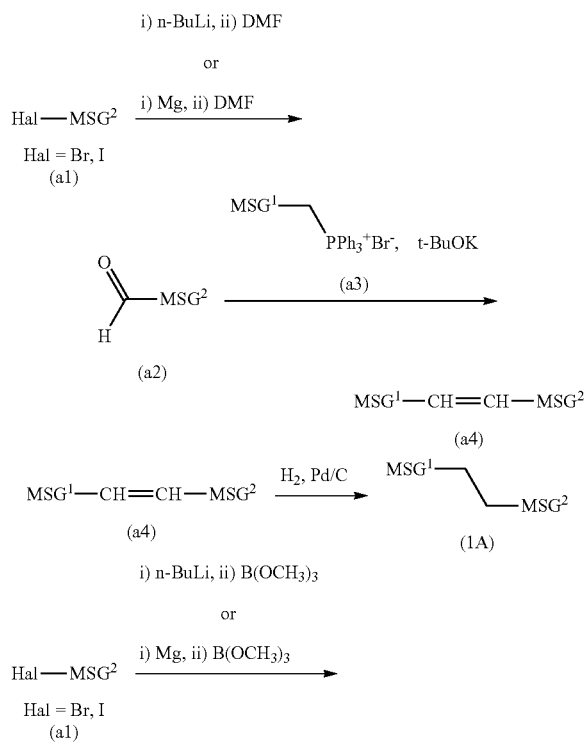

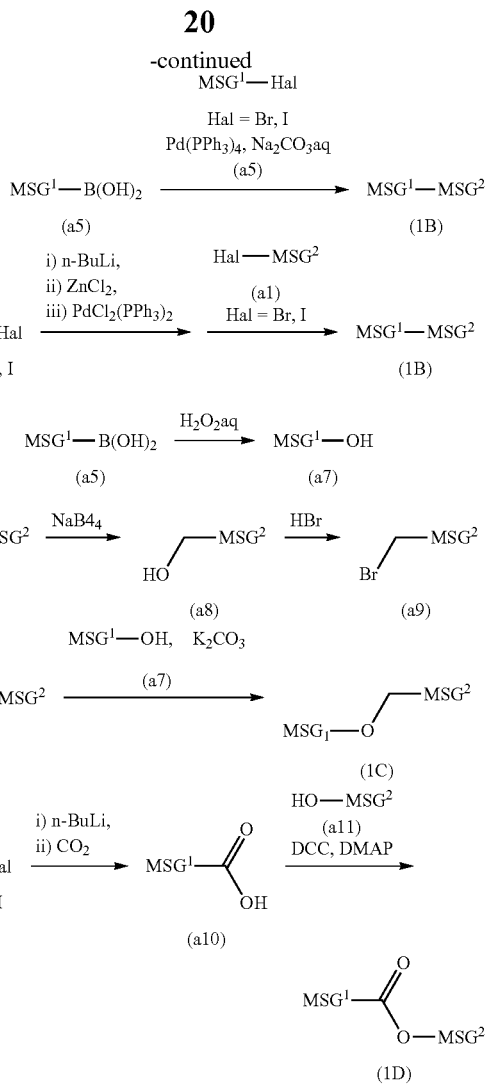

(1) Formation of —$(CH_2)_2$—

Aldehyde (a2) is obtained by allowing an intermediate obtained by allowing organohalogen compound (a1) to react with butyllithium (or magnesium) with formamide such as N,N-dimethylformamide (DMF). Compound (a4) having a double bond is obtained by allowing aldehyde (a2) to react with phosphorus ylide obtained by treating phosphonium salt (a3) with a base such as potassium t-butoxide. Compound (1A) is prepared by hydrogenating compound (a4) in the presence of a catalyst such as palladium on carbon (Pd/C).

(2) Formation of a Single Bond

A Grignard reagent (or lithium salt) is prepared by allowing organohalogen compound (a1) to react with magnesium (or butyllithium). Dihydroxyborane (a5) is obtained by allowing the Grignard reagent (or lithium salt) to react with a boric acid ester such as trimethyl borate, and then by hydrolyzing the resulting product in the presence of acid such as hydrochloric acid. Compound (1B) is prepared by allowing compound (a5) to react with organohalogen compound (a6) in an aqueous carbonate solution in the presence of a tetrakis(triphenylphosphine)palladium (Pd(PPh$_3$)$_4$) catalyst.

A method described below can also be applied thereto. Organohalogen compound (a6) is allowed to react with butyl lithium and further with zinc chloride. Compound (1B) is prepared by allowing the resulting intermediate to react with compound (a1) in the presence of bistriphenylphosphine dichloropalladium (Pd(PPh$_3$)$_2$C$_{12}$).

(3) Formation of —CH$_2$O— or —OCH$_2$—

Alcohol (a7) is obtained by oxidizing dihydroxyborane (a5) with an oxidizing agent such as hydrogen peroxide. Separately, alcohol (a8) is obtained by reducing aldehyde (a3) with a reducing agent such as sodium borohydride. Halogen compound (a9) is obtained by halogenating the alcohol (a8) with hydrobromic acid or the like. Compound (1C) is prepared by allowing the halide (a9) to react, in the presence of potassium carbonate or the like, with the alcohol (a7) previously obtained.

(4) Formation of —COO— or —OCO—

Carboxylic acid (a10) is obtained by allowing compound (a6) to react with n-butyllithium and subsequently with carbon dioxide. Compound (1D) having —COO— is prepared by dehydration of carboxylic acid (a10) and phenol (a11) in the presence of 1,3-dicyclohexylcarbodiimide (DCC) and 4-dimethylaminopyridine (DMAP). A compound having —OCO— can also be prepared according to the method.

1-3-2. Synthesis Example

An example of a method for preparing compound (1) is as described below. In the compounds, definitions of R$^1$, R$^2$, ring A$^1$, ring A$^2$, Z$^1$, Z$^2$, a and b are identical to definitions described in the above section 1. Then, (b-2) is obtained by lithiation, with sec-BuLi, compound (b-1) prepared according to a publicly known method, and allowing the resulting material to react with S and bromoacetaldehyde diethyl acetal. Then, (b-3) is obtained by allowing (b-2) to react with polyphosphoric acid in toluene or chlorobenzene. Various intermediates are obtained by lithiation, with LDA, (b-3) into (b-4), and allowing (b-4) to react with various reagents. Compound (1) is derived therefrom, by using the intermediates, by a publicly known method.

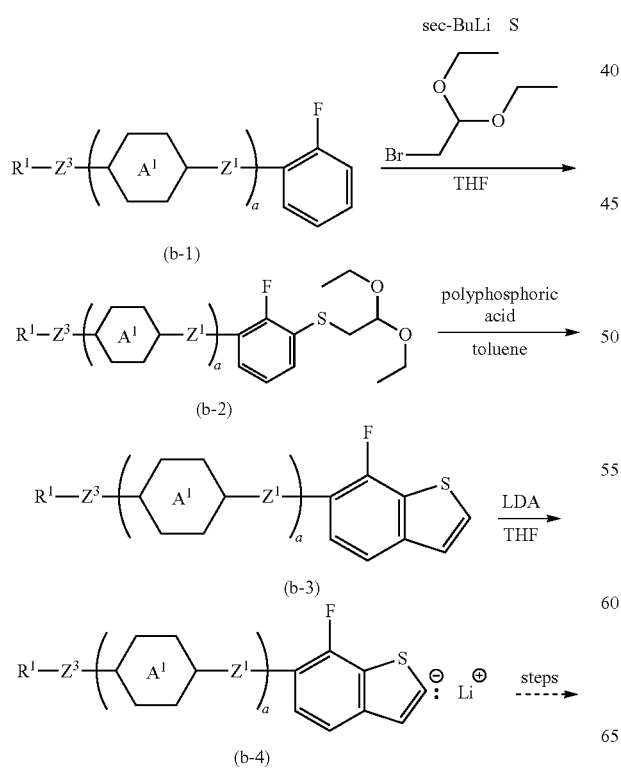

2. Composition (1)

A liquid crystal composition (1) of the invention will be described. The composition (1) contains at least one compound (1) as component A. The composition (1) may contain two or more compounds (1). A component of the liquid crystal composition may be compound (1) only. In order to develop excellent physical properties, composition (1) preferably contains at least one of compounds (1) in the range of 1 to 99% by weight. Ina composition having positive dielectric anisotropy, a preferred content of compound (1) is in the range of 5 to 60% by weight. In a composition having negative dielectric anisotropy, a preferred content of compound (1) is 30% by weight or less. Composition (1) may also contain compound (1) and various liquid crystal compounds that are not described herein.

A preferred composition contains a compound selected from components B, C, D and E shown below. When composition (1) is prepared, a component thereof can be selected, for example, by taking dielectric anisotropy of compound (1) into consideration. A composition prepared by suitably selecting the components has high maximum temperature of a nematic phase, low minimum temperature of the nematic phase, small viscosity, suitable optical anisotropy, large dielectric anisotropy and a suitable elastic constant.

Component B includes compounds (2) to (4). Component C is compound (5). Component D includes compounds (6) to (12). Component E includes compounds (13) to (15). The components will be described in the order.

Component B is a compound having a halogen-containing group or a fluorine-containing group at a right terminal. Preferred examples of component B include compounds (2-1) to (2-16), compounds (3-1) to (3-113) and compounds (4-1) to (4-57).

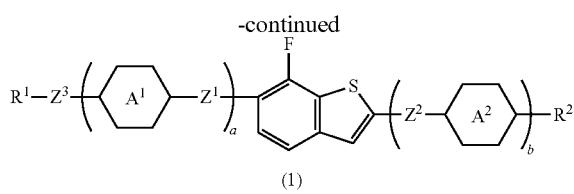

(1)

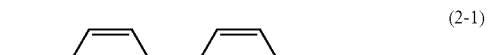

(2-1)

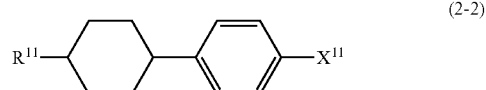

(2-2)

(2-3)

(2-4)

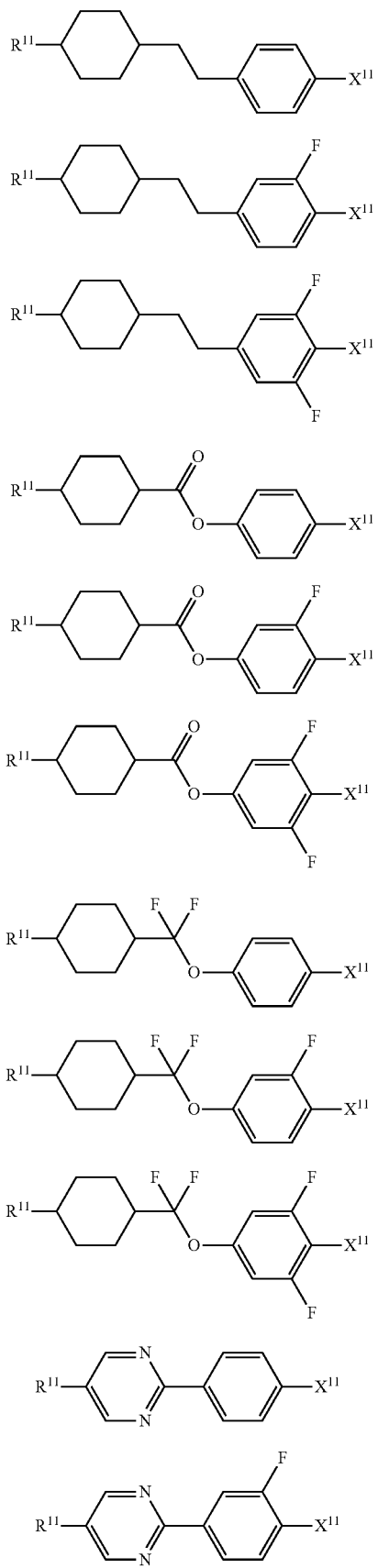
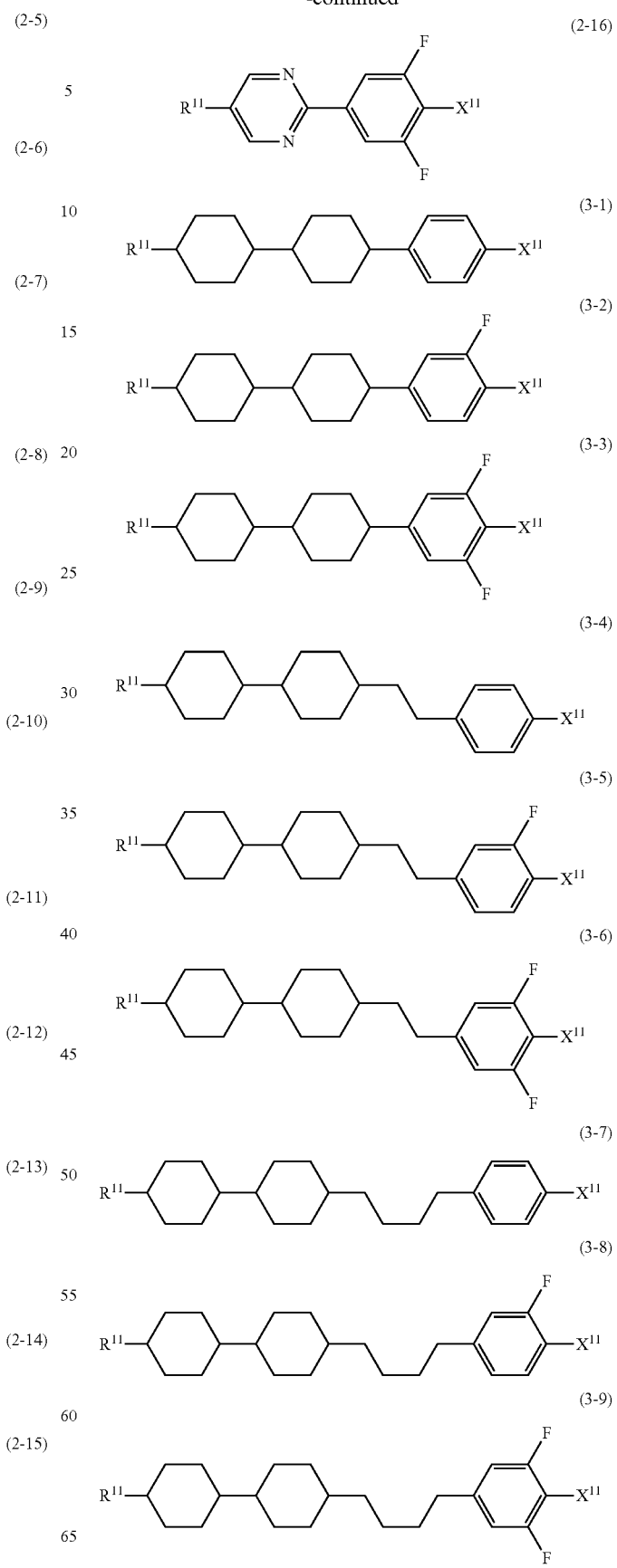

(3-10)
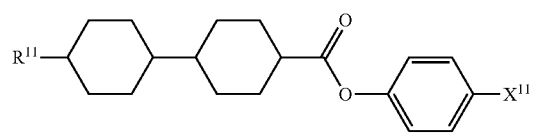
(3-11)
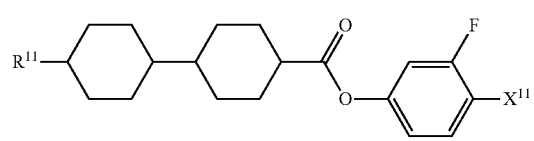
(3-12)
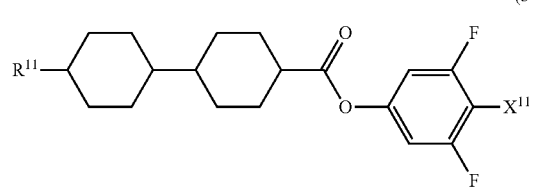
(3-13)
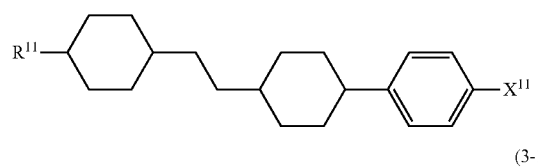
(3-14)
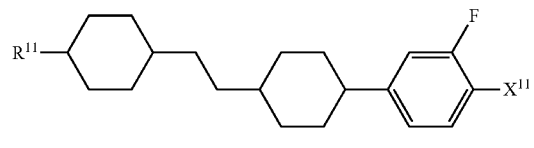
(3-15)
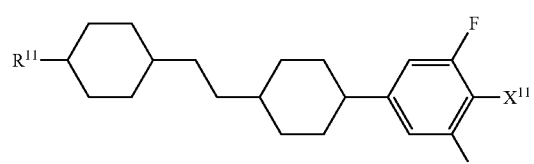
(3-16)
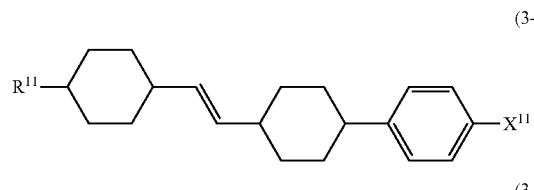
(3-17)
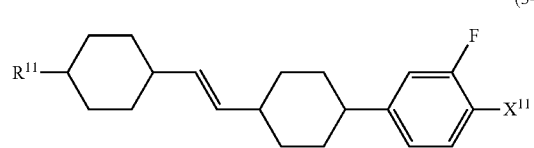
(3-18)
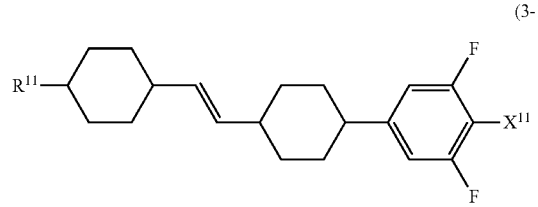
(3-19)
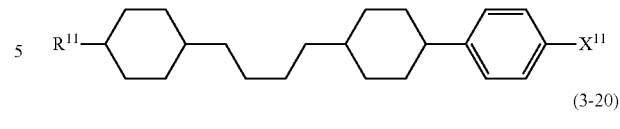
(3-20)
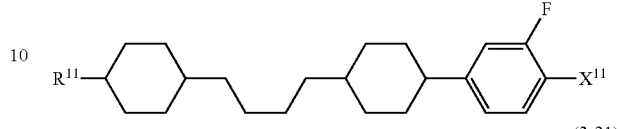
(3-21)
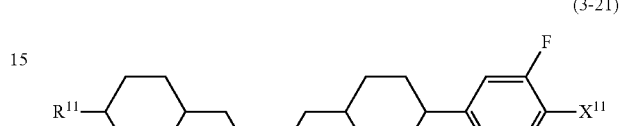
(3-22)
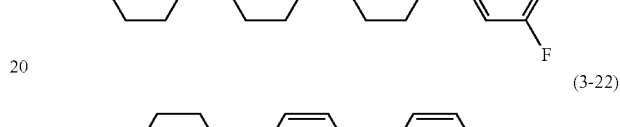
(3-23)
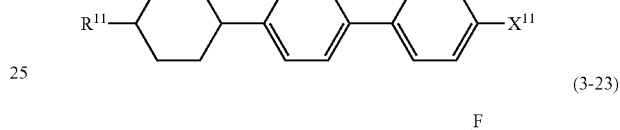
(3-24)
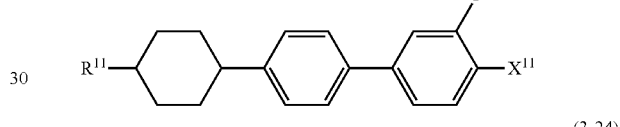
(3-25)
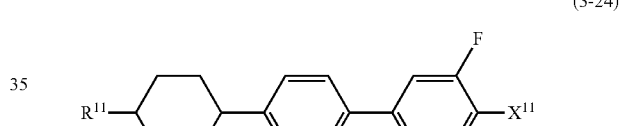
(3-26)
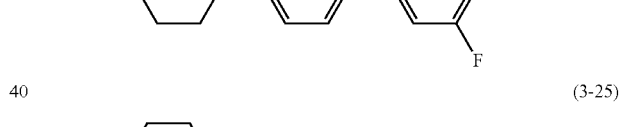
(3-27)
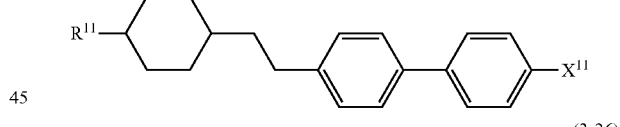
(3-28)
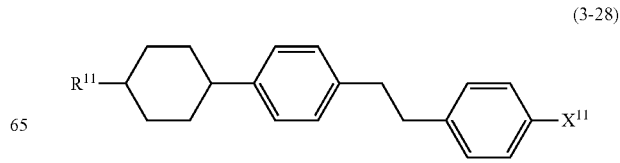

(3-29) 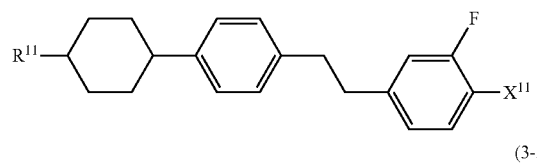
(3-30) 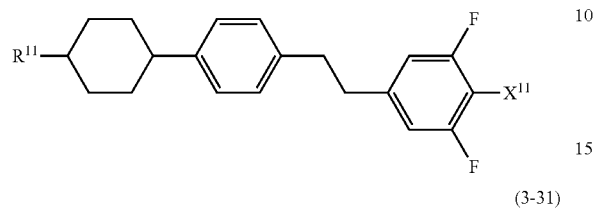
(3-31) 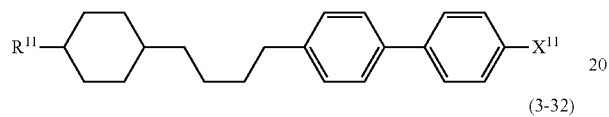
(3-32) 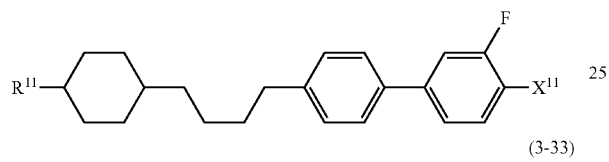
(3-33) 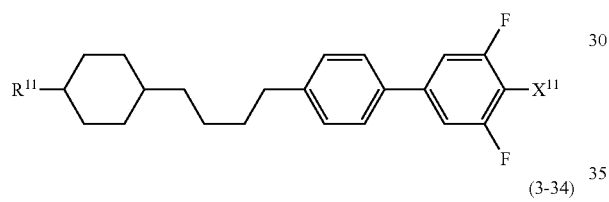
(3-34) 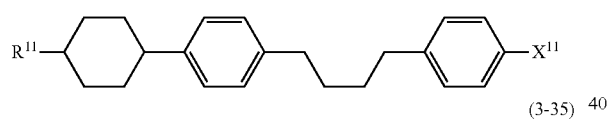
(3-35) 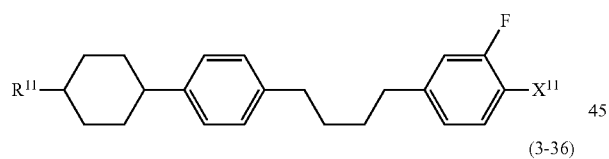
(3-36) 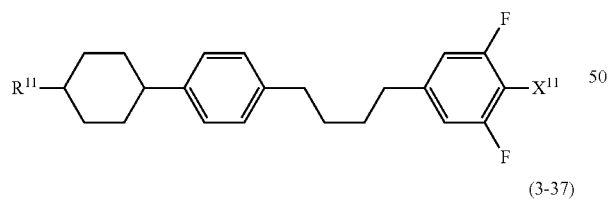
(3-37) 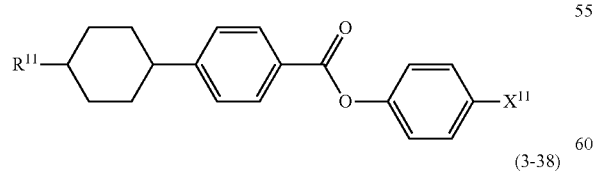
(3-38) 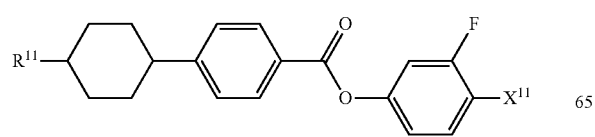
(3-39) 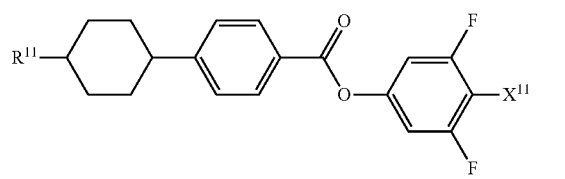
(3-40) 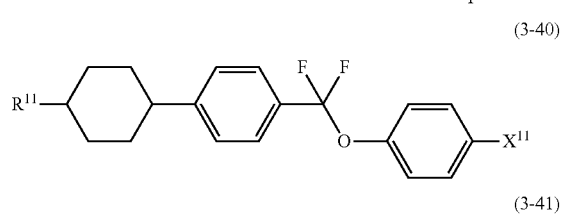
(3-41) 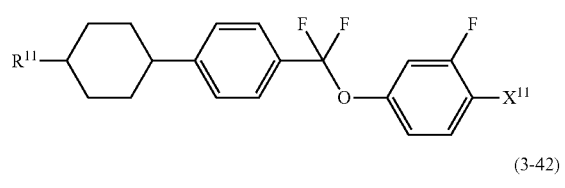
(3-42) 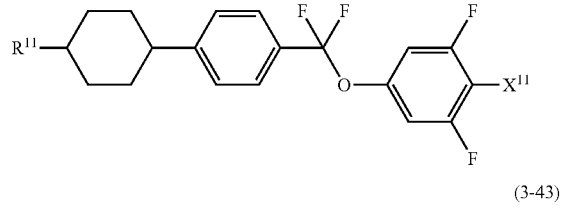
(3-43) 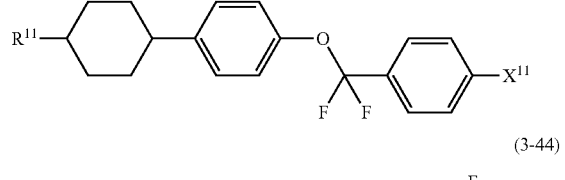
(3-44) 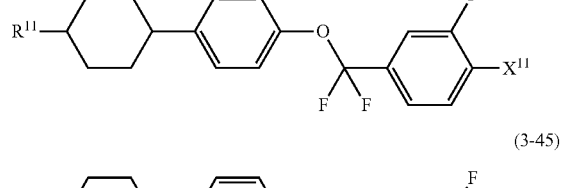
(3-45) 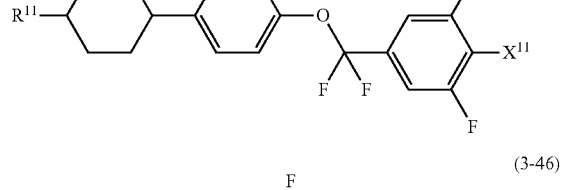
(3-46) 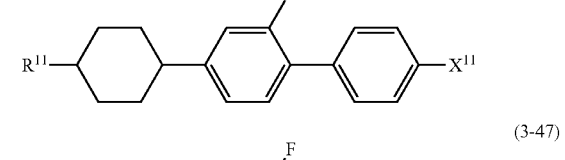
(3-47) 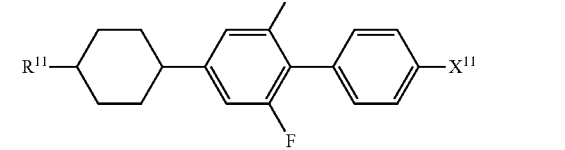

(3-48) 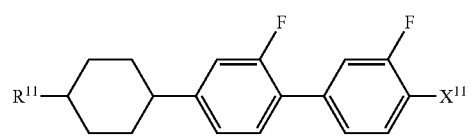
(3-49) 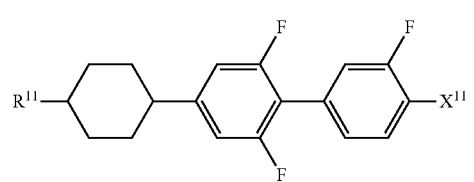
(3-50) 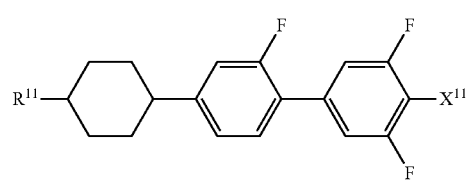
(3-51) 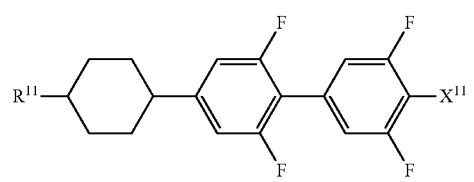
(3-52) 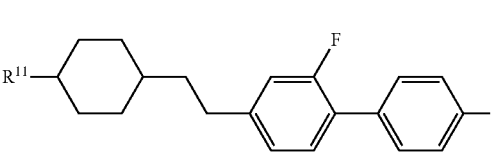
(3-53) 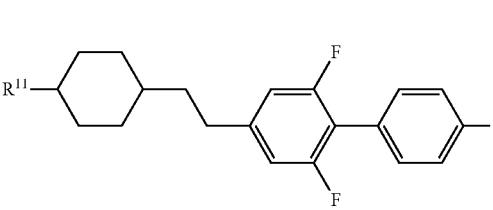
(3-54) 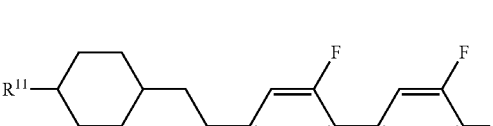
(3-55) 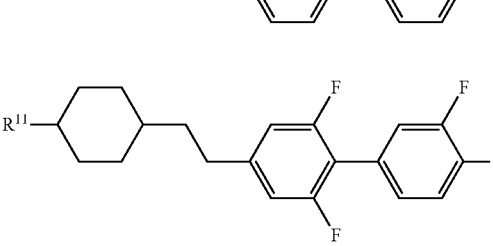
(3-56) 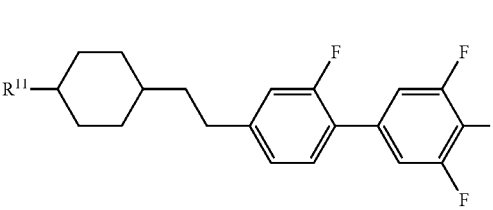
(3-57) 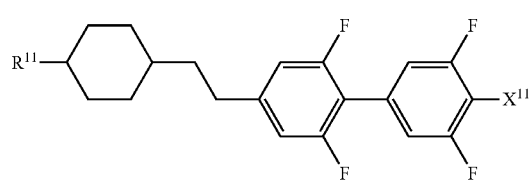
(3-58) 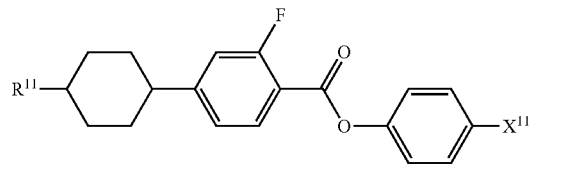
(3-59) 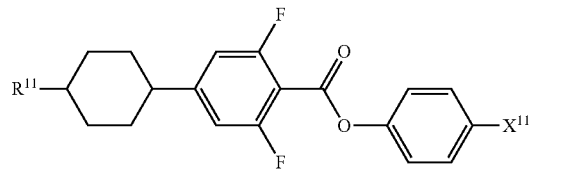
(3-60) 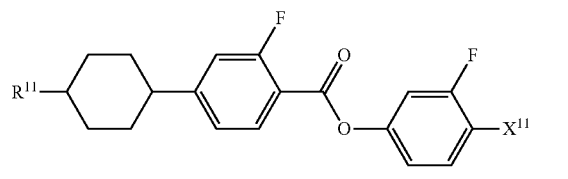
(3-61) 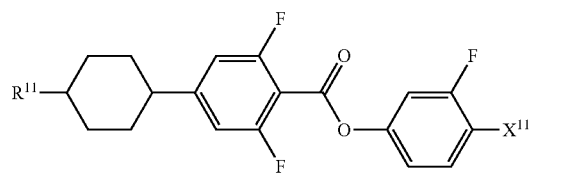
(3-62) 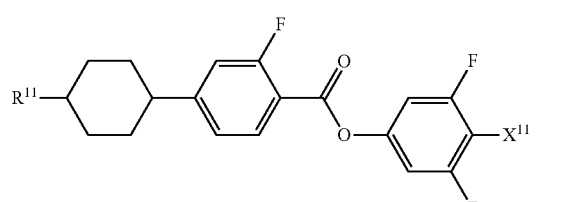
(3-63) 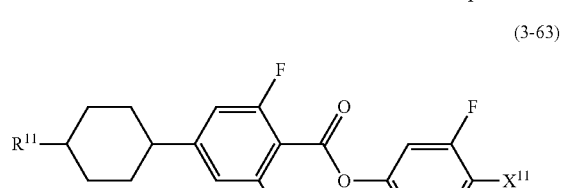
(3-64) 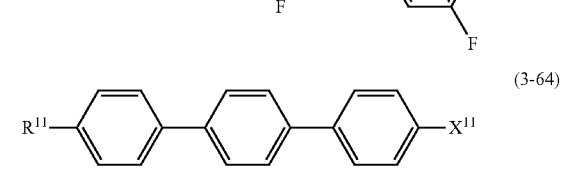

(3-65) 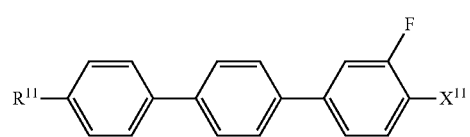
(3-66) 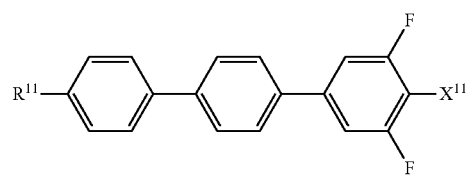
(3-67) 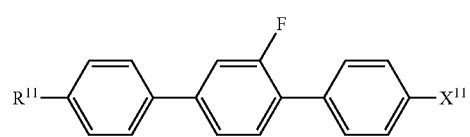
(3-68) 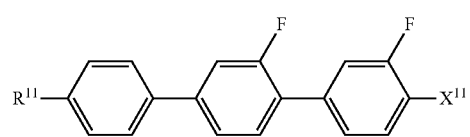
(3-69) 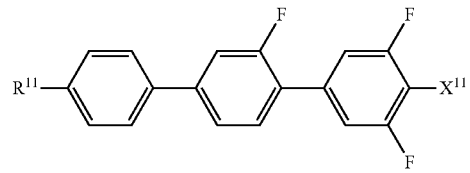
(3-70) 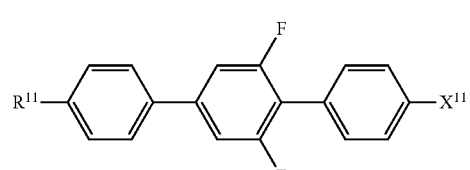
(3-71) 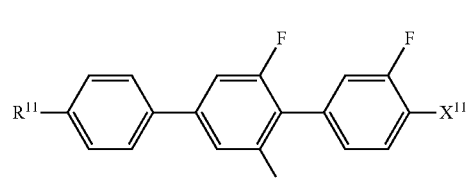
(3-72) 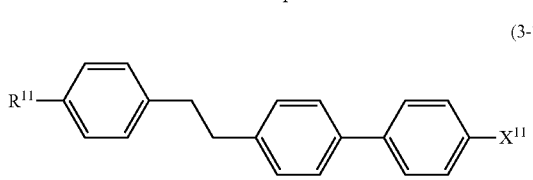
(3-73) 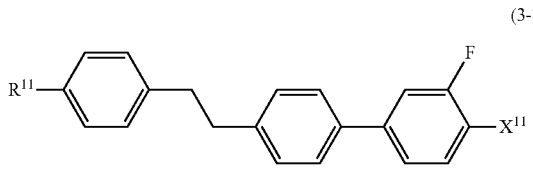
(3-74) 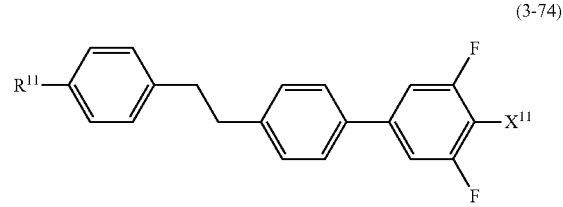
(3-75) 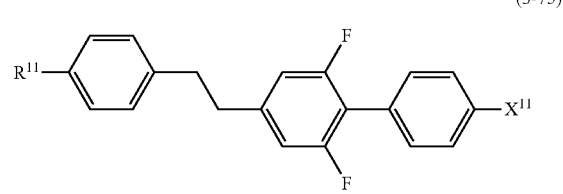
(3-76) 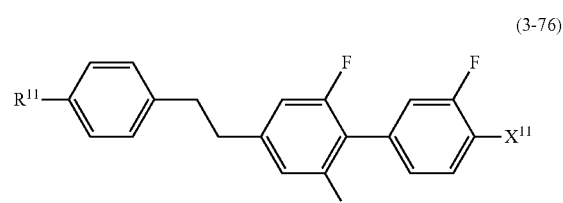
(3-77) 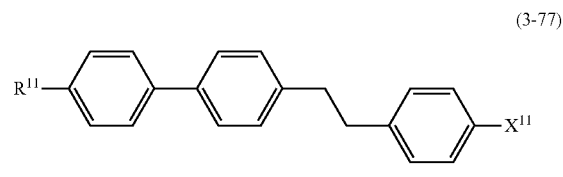
(3-78) 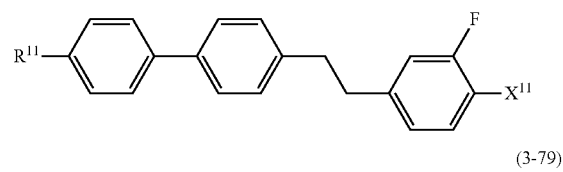
(3-79) 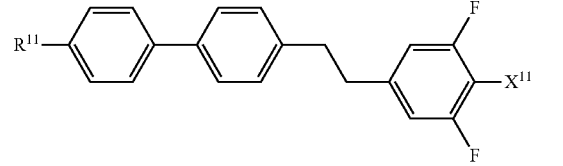
(3-80) 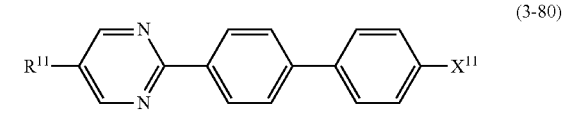
(3-81) 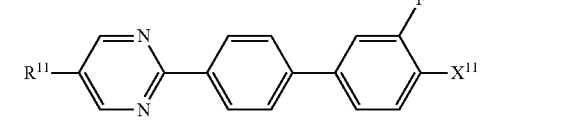
(3-82) 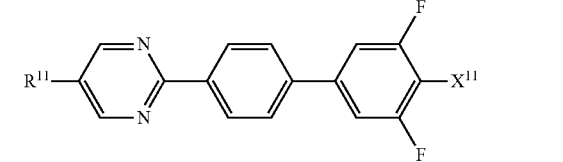

(3-83) 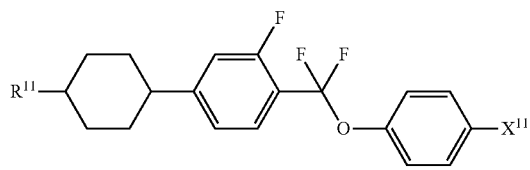
(3-84) 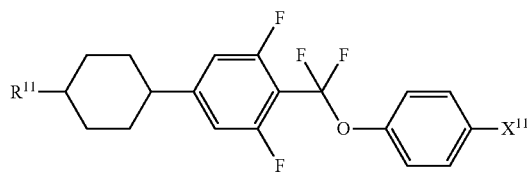
(3-85) 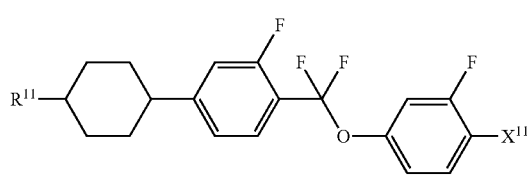
(3-86) 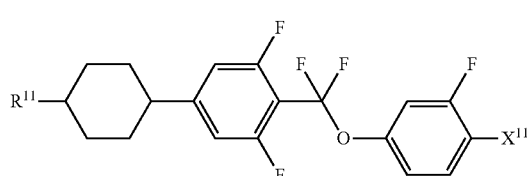
(3-87) 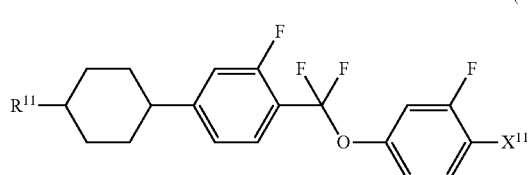
(3-88) 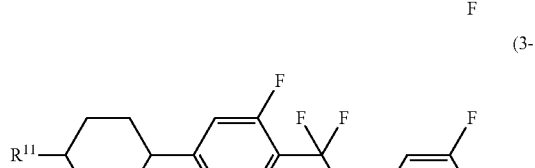
(3-89) 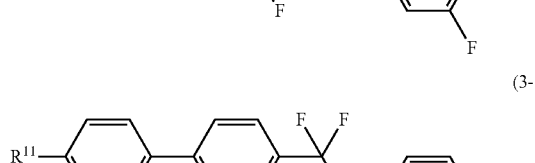
(3-90) 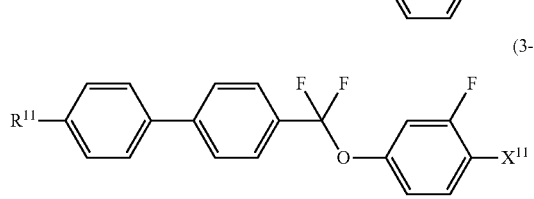
(3-91) 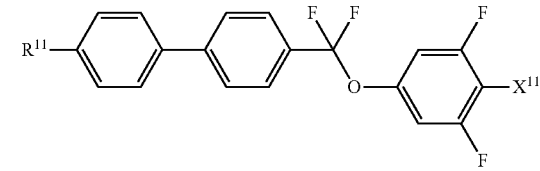
(3-92) 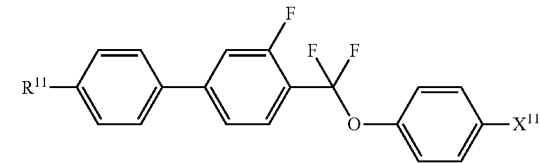
(3-93) 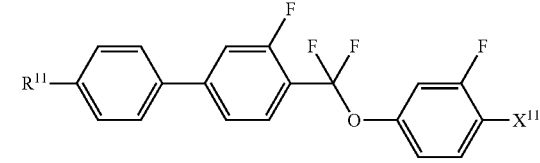
(3-94) 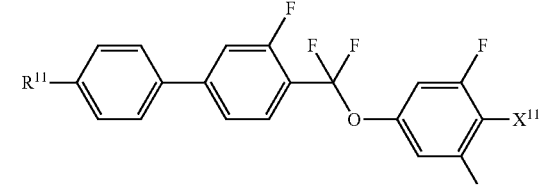
(3-95) 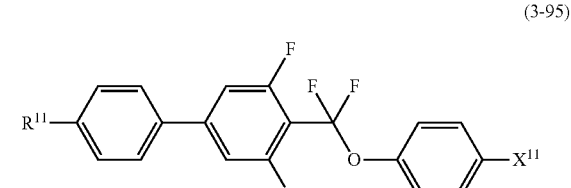
(3-96) 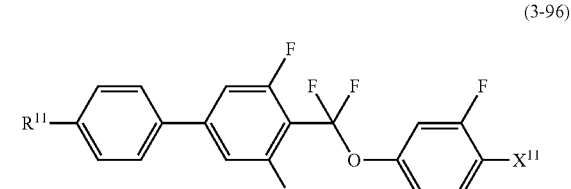
(3-97) 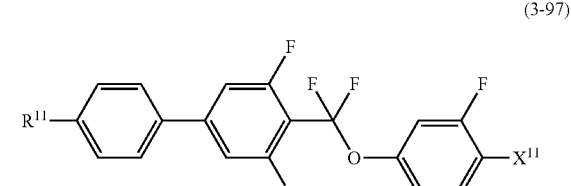
(3-98) 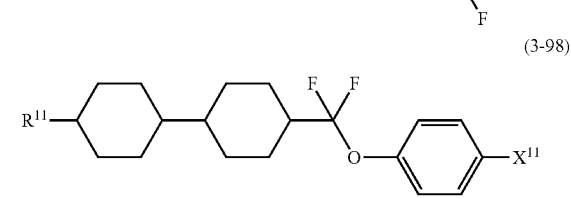

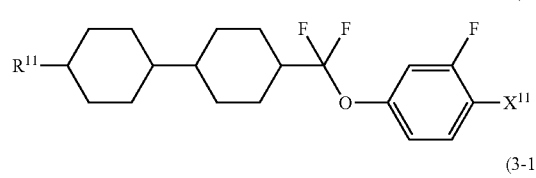
(3-99)
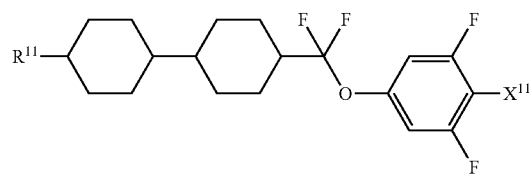
(3-100)
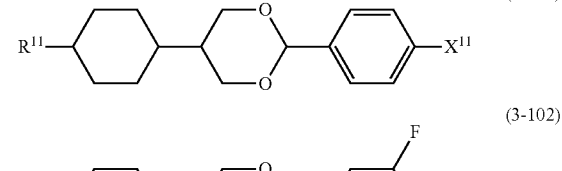
(3-101)
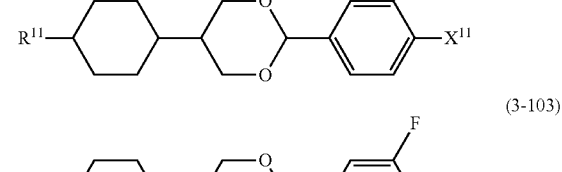
(3-102)
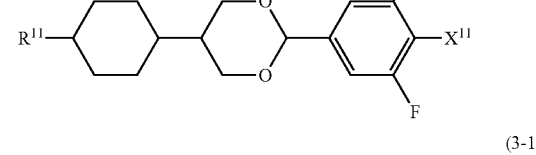
(3-103)
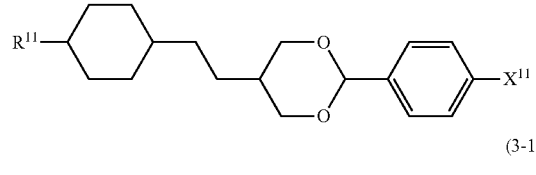
(3-104)
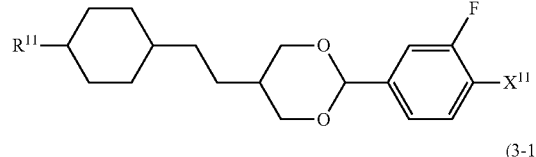
(3-105)
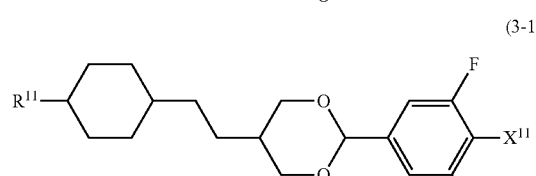
(3-106)
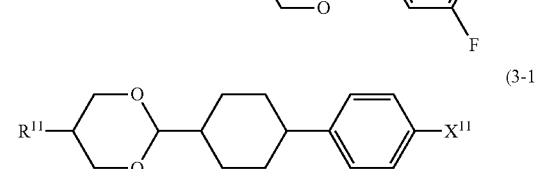
(3-107)
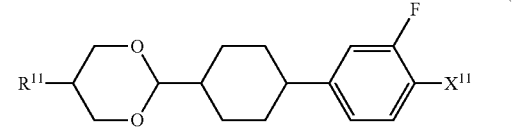
(3-108)
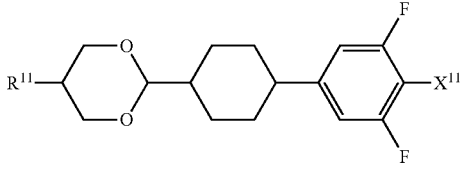
(3-109)
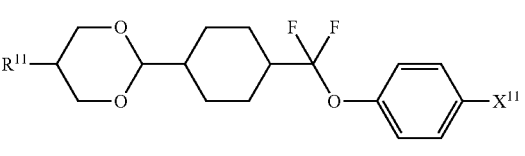
(3-110)
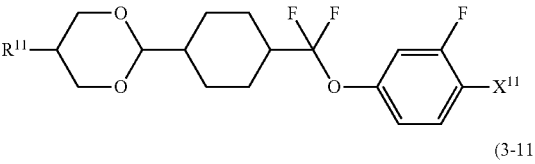
(3-111)
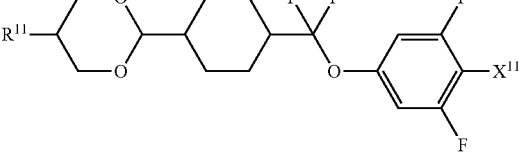
(3-112)
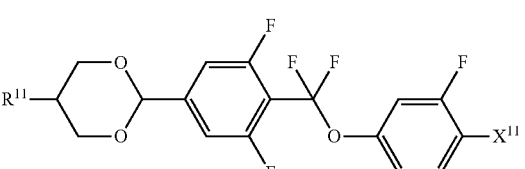
(3-113)
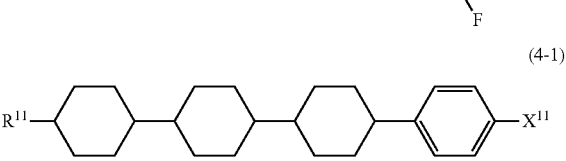
(4-1)
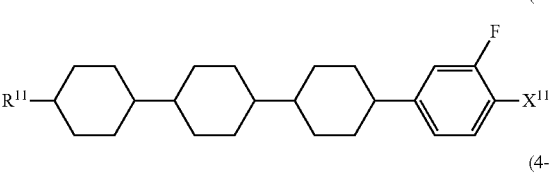
(4-2)
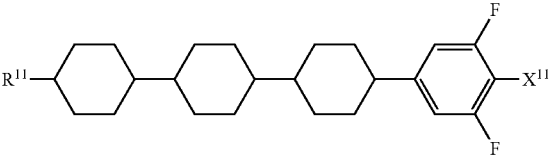
(4-3)
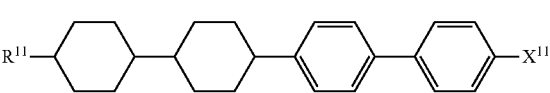
(4-4)

(4-5) 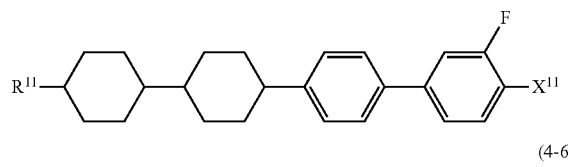
(4-6) 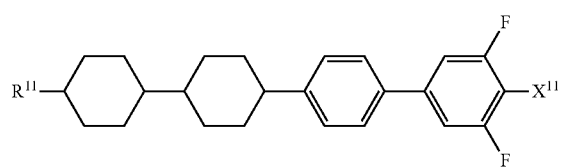
(4-7) 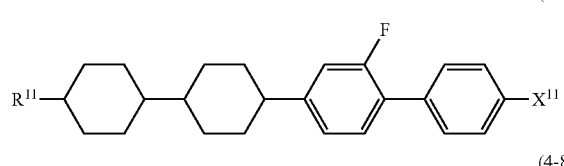
(4-8) 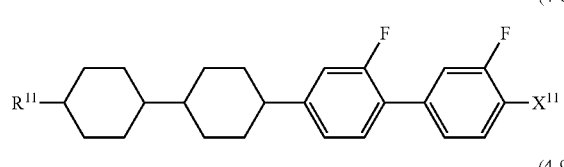
(4-9) 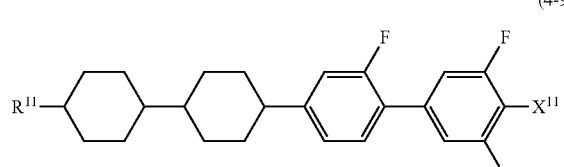
(4-10) 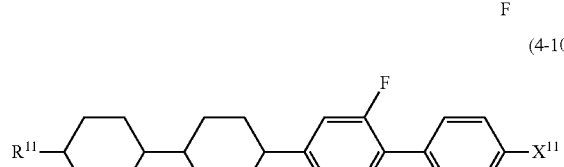
(4-11) 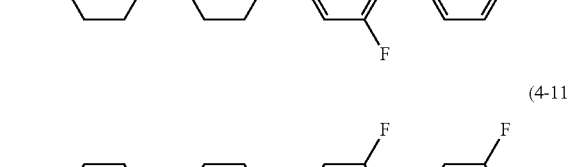
(4-12) 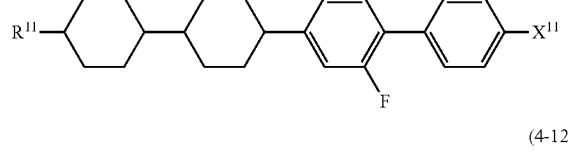
(4-13) 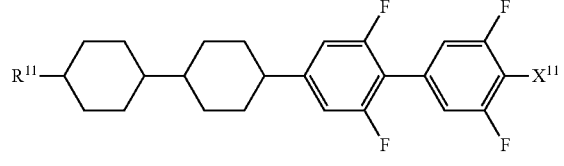
(4-14) 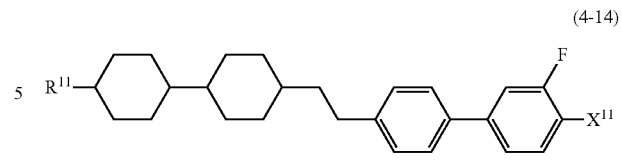
(4-15) 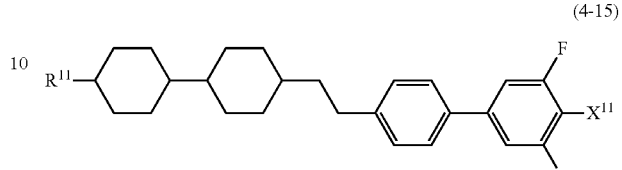
(4-16) 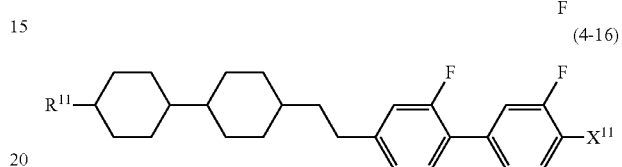
(4-17) 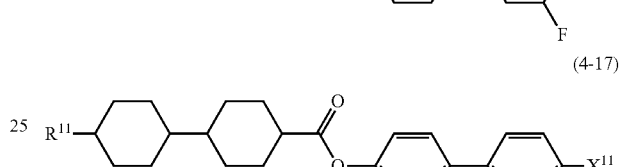
(4-18) 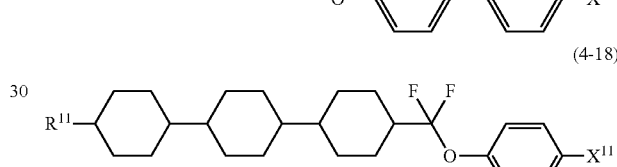
(4-19) 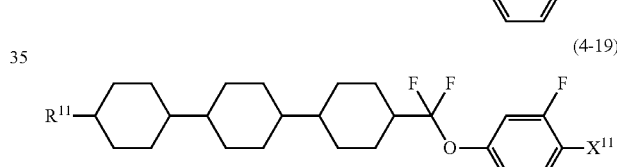
(4-20) 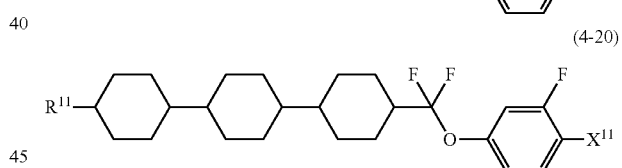
(4-21) 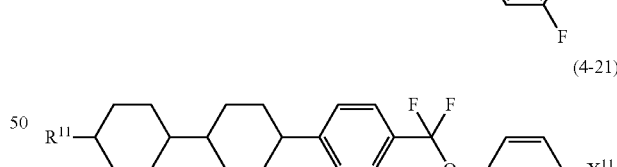
(4-22) 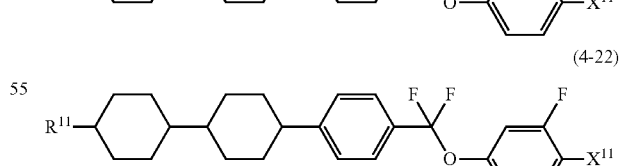
(4-23) 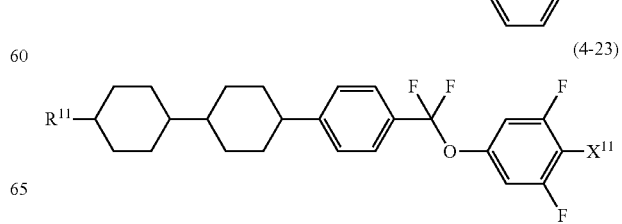

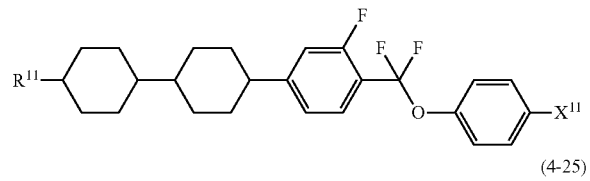
(4-24)
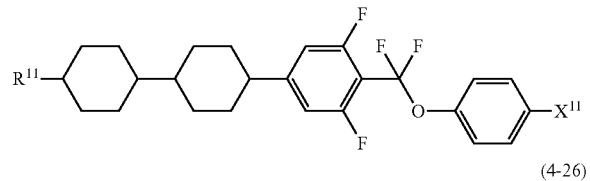
(4-25)
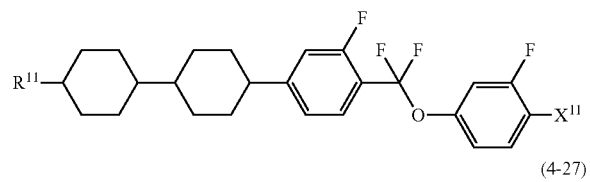
(4-26)
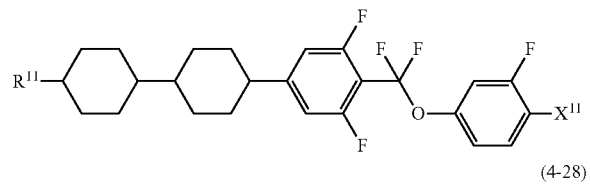
(4-27)
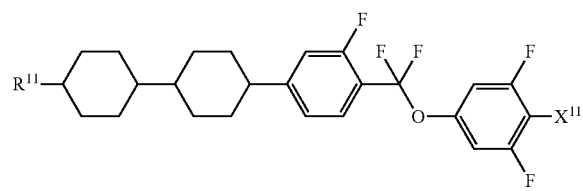
(4-28)
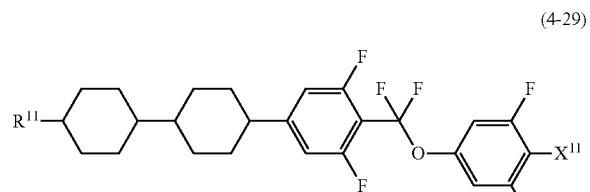
(4-29)
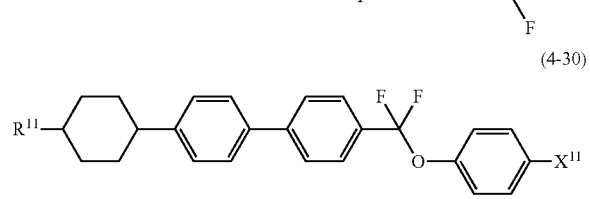
(4-30)
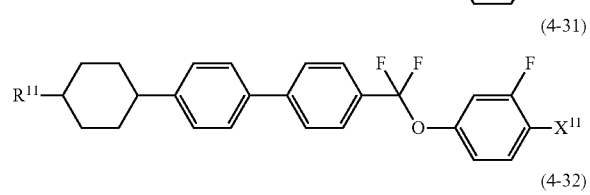
(4-31)
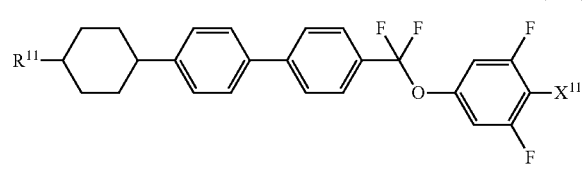
(4-32)
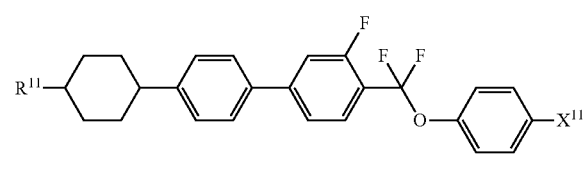
(4-33)
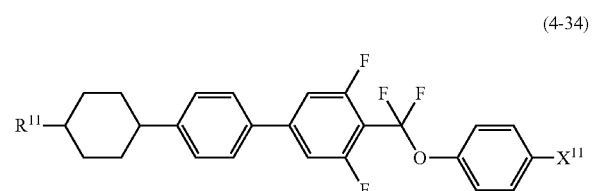
(4-34)
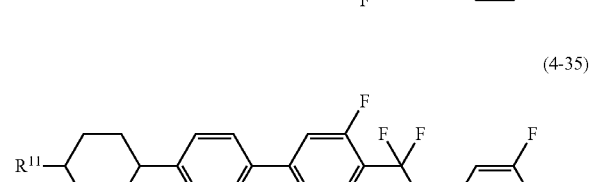
(4-35)
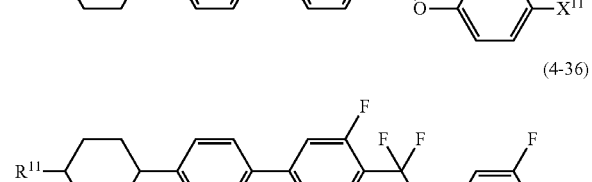
(4-36)
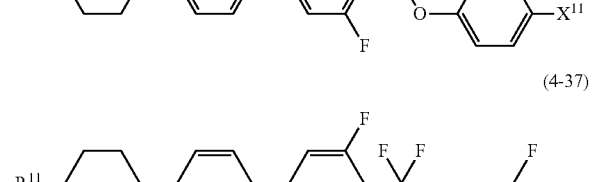
(4-37)
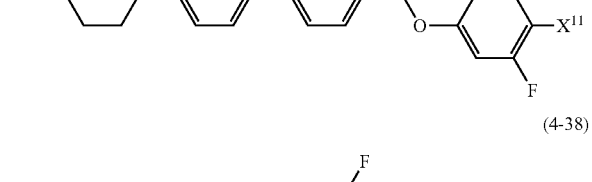
(4-38)
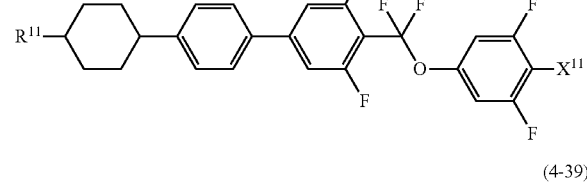
(4-39)
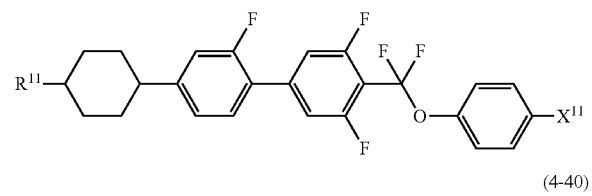
(4-40)
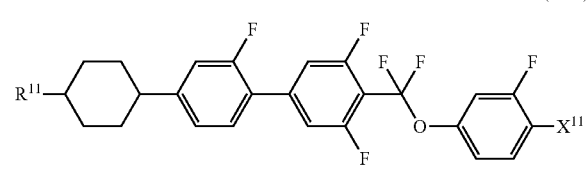

(4-41)
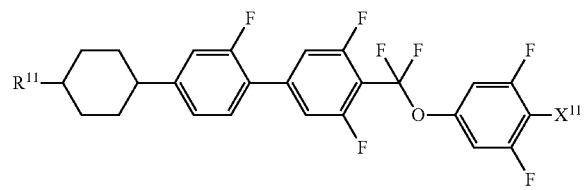
(4-42)
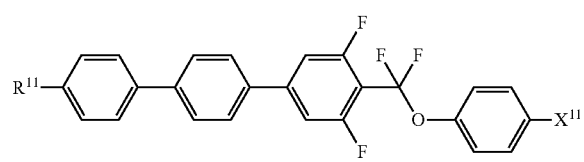
(4-43)
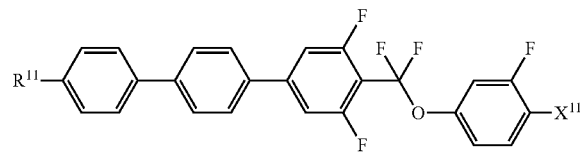
(4-44)
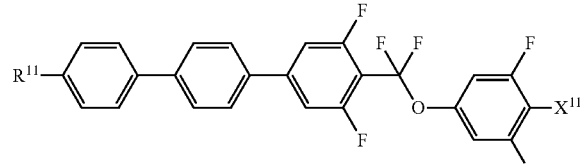
(4-45)
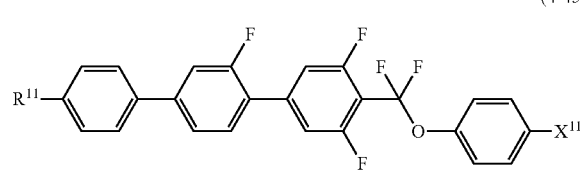
(4-46)
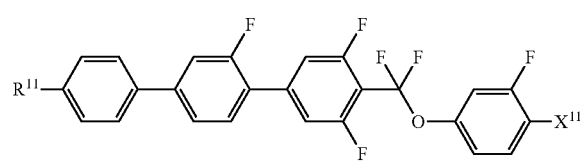
(4-47)
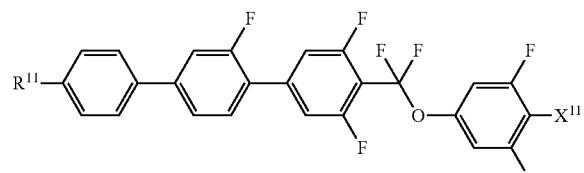
(4-48)
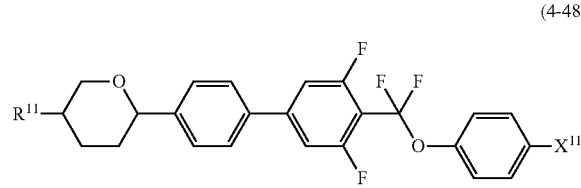
(4-49)
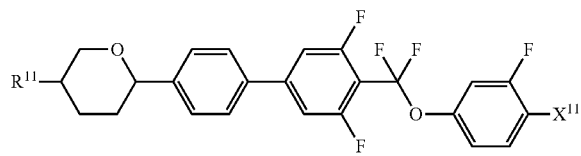
(4-50)
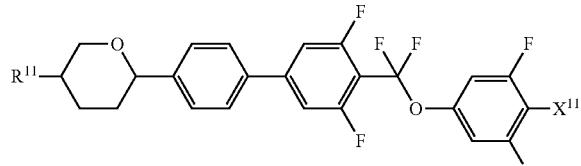
(4-51)
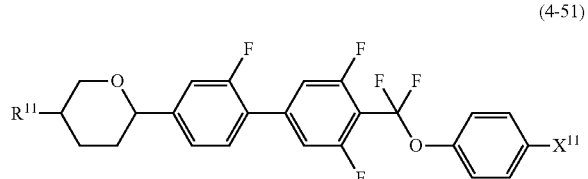
(4-52)
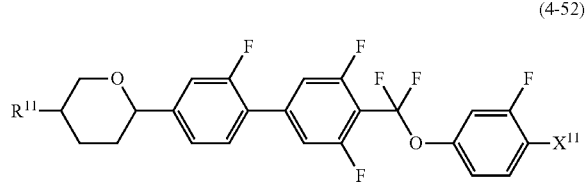
(4-53)
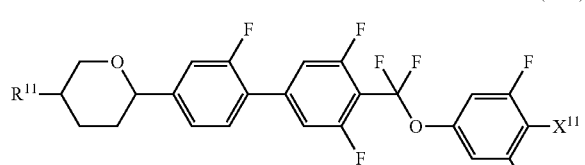
(4-54)
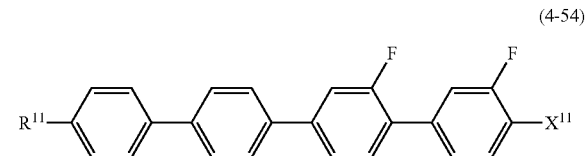
(4-55)
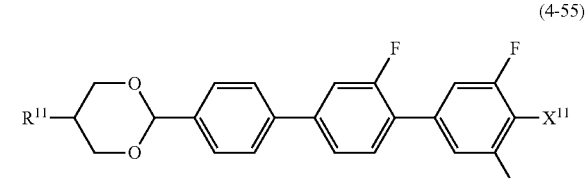
(4-56)
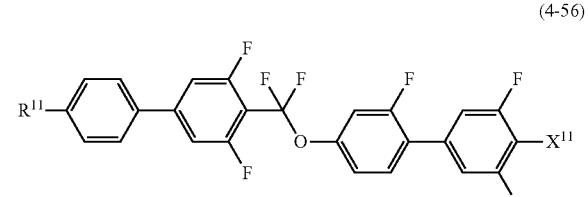

(4-57)
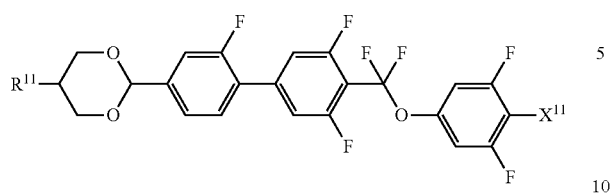

In the compounds (component B), $R^{11}$ and $X^{11}$ are defined in a manner identical with the definitions in the formulas (2) to (4).

Component B has positive dielectric anisotropy and superb stability to heat, light and so forth, and therefore is used when a composition for the TFT mode or the PSA mode is prepared. A content of component B is suitably in the range of 1 to 99% by weight, preferably in the range of 10 to 97% by weight, and further preferably in the range of 40 to 95% by weight, based on the total weight of the composition. Viscosity of the composition can be adjusted by further adding compounds (12) to (14) (component E) thereto.

Component C is a compound having —C≡N or —C≡C—C≡N at a right terminal group. Preferred examples of component C include compounds (5-1) to (5-64).

(5-1)
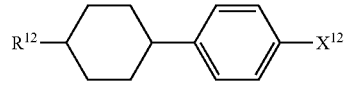

(5-2)
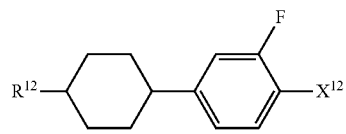

(5-3)
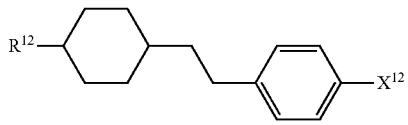

(5-4)
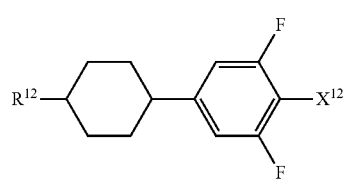

(5-5)
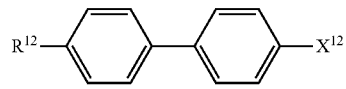

(5-6)
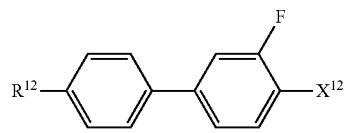

(5-7)
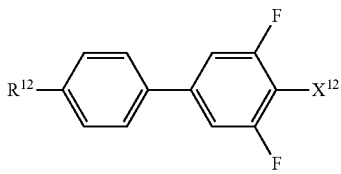

(5-8)
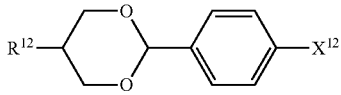

(5-9)
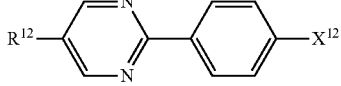

(5-10)
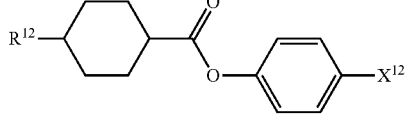

(5-11)
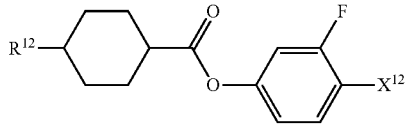

(5-12)
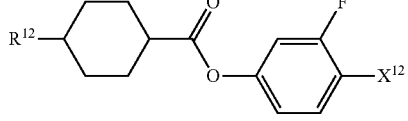

(5-13)
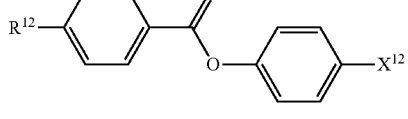

(5-14)
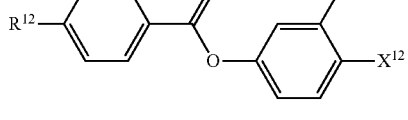

(5-15)
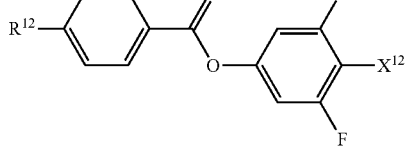

(5-16)
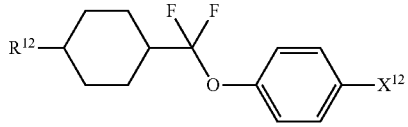

(5-17)
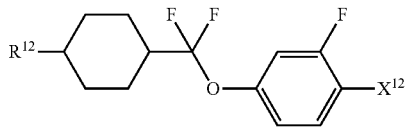

(5-18) 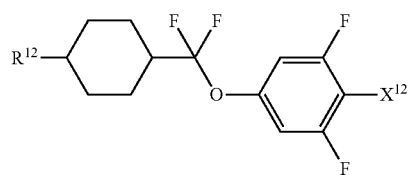
(5-19) 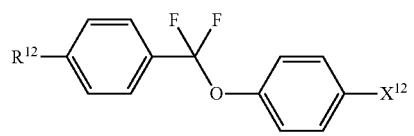
(5-20) 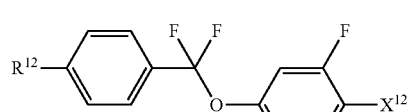
(5-21) 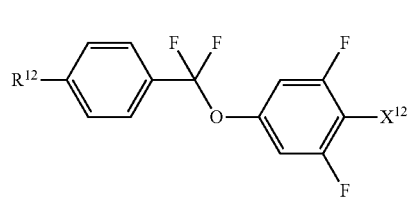
(5-22) 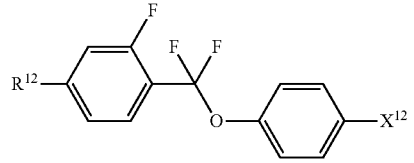
(5-23) 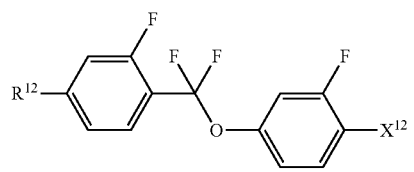
(5-24) 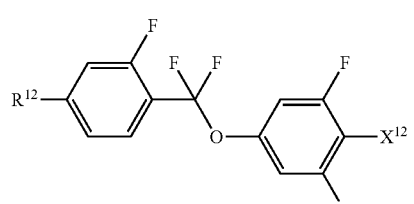
(5-25) 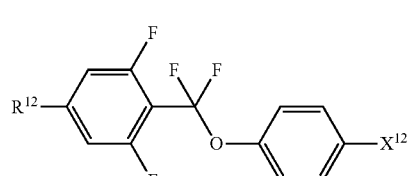
(5-26) 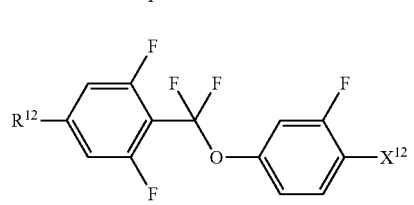
(5-27) 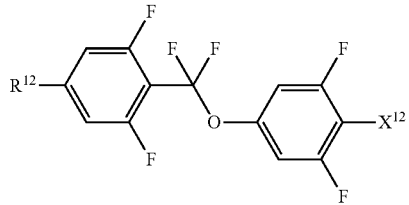
(5-28) 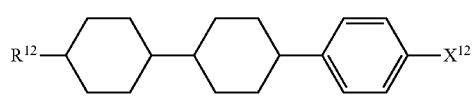
(5-29) 
(5-30) 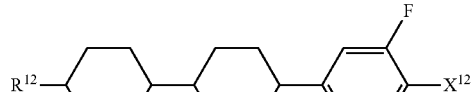
(5-31) 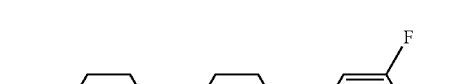
(5-32) 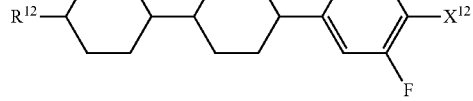
(5-33) 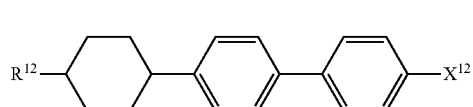
(5-34) 
(5-35) 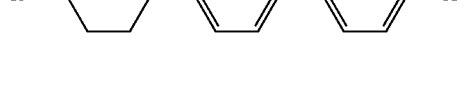
(5-36) 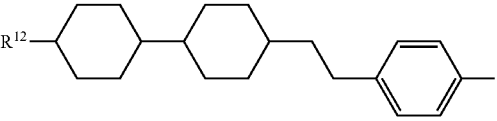

(5-37)
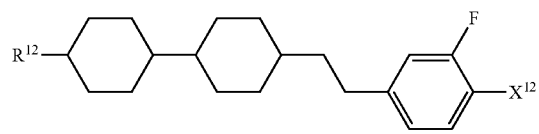
(5-38)
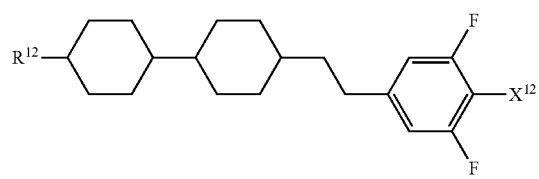
(5-39)
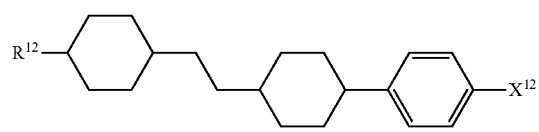
(5-40)
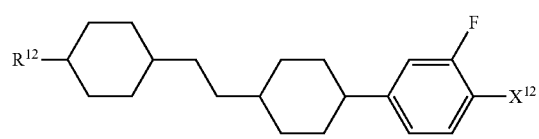
(5-41)
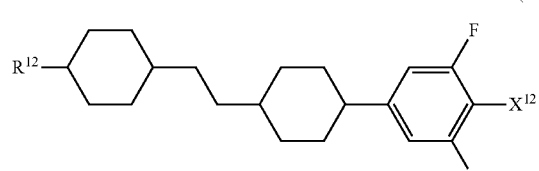
(5-42)
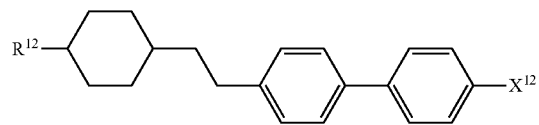
(5-43)
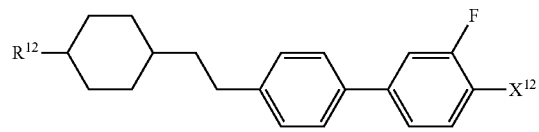
(5-44)
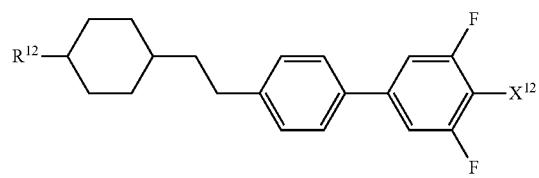
(5-45)
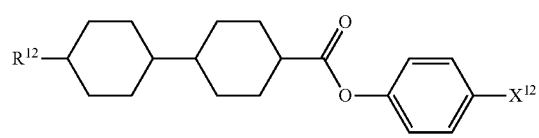
(5-46)
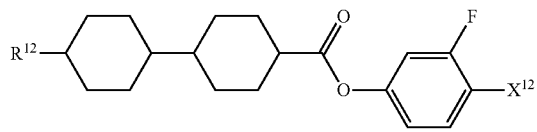
(5-47)
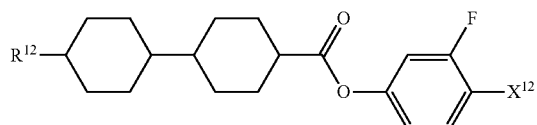
(5-48)
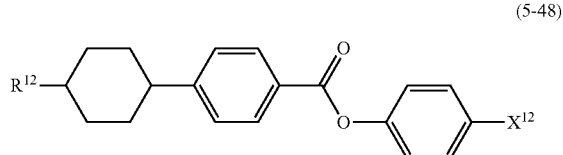
(5-49)
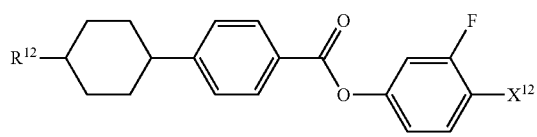
(5-50)
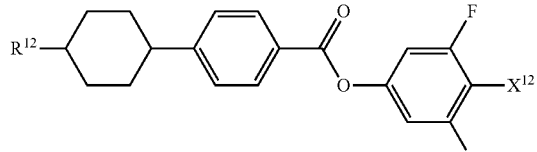
(5-51)
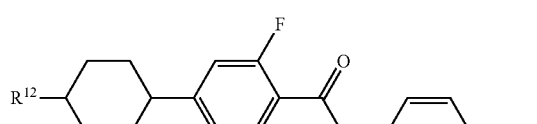
(5-52)
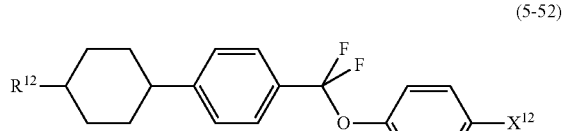
(5-53)
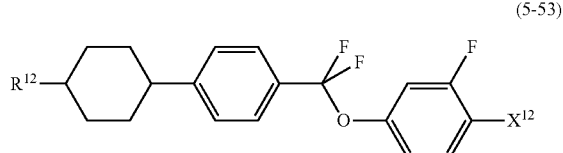
(5-54)
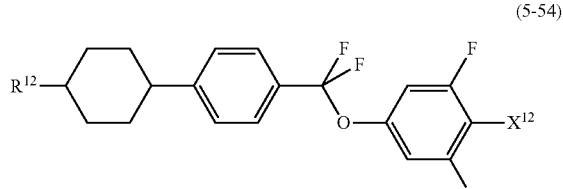

(5-55)
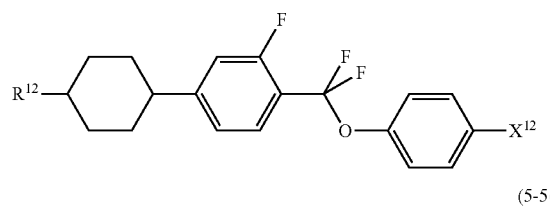

(5-56)
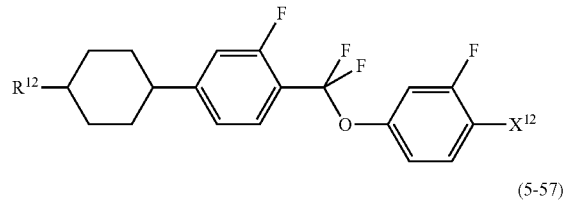

(5-57)
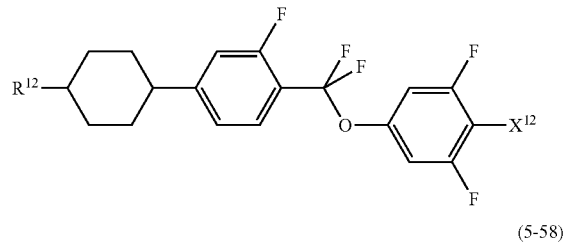

(5-58)
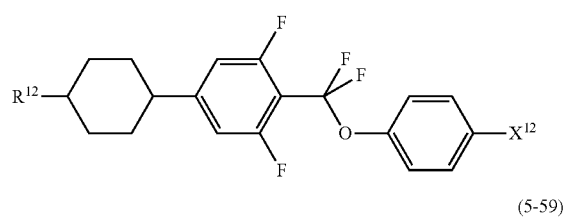

(5-59)
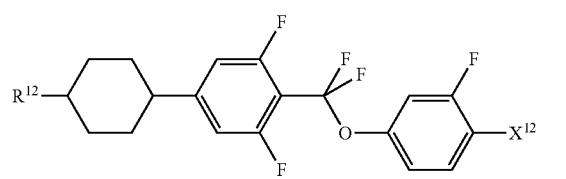

(5-60)
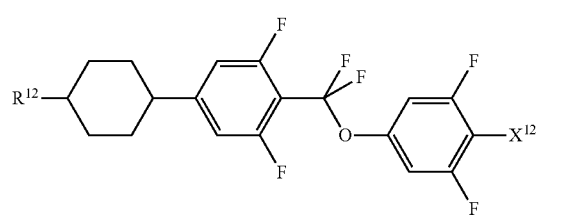

(5-61)
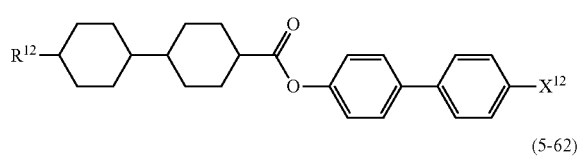

(5-62)
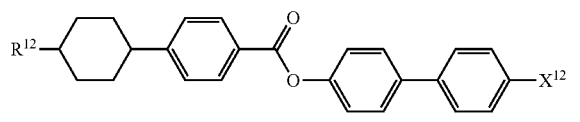

(5-63)

(5-64)
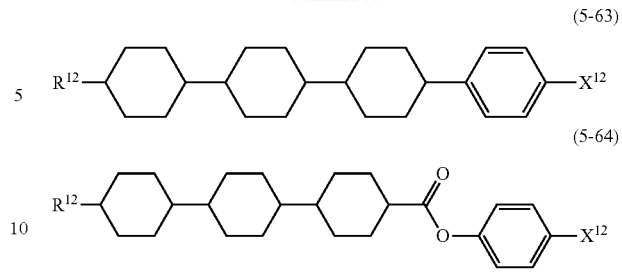

In the compounds (component C), $R^{12}$ and $X^{12}$ are defined in a manner identical with the definitions in formula (5).

Component C has positive dielectric anisotropy, and a large value thereof, and therefore is mainly used when a composition for the STN mode, the TN mode or the PSA mode is prepared. Dielectric anisotropy of the composition can be increased by adding the component C thereto. Component C is effective in extending the temperature range of the liquid crystal phase, adjusting the viscosity or adjusting the optical anisotropy. Component C is useful also for adjustment of a voltage-transmittance curve of the device.

When a composition for the STN mode or the TN mode is prepared, a content of component C is preferably in the range of 1 to 99% by weight, preferably in the range of 10 to 97% by weight, and further preferably in the range of 40 to 95% by weight, based on the total weight of the composition. The temperature range of the liquid crystal phase, the viscosity, the optical anisotropy, the dielectric anisotropy or the like of the composition can be adjusted by adding component E thereto.

Component D includes compounds (6) to (12). The compounds have a benzene ring in which hydrogen in lateral positions are replaced by two halogen atoms, such as 2,3-difluoro-1,4-phenylene Preferred examples of component D include compounds (6-1) to (6-8), compounds (7-1) to (7-17), compound (8-1), compounds (9-1) to (9-3), compounds (10-1) to (10-11), compounds (11-1) to (11-3) and compounds (12-1) to (12-3).

(6-1)
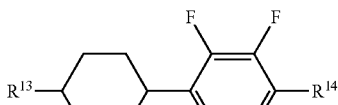

(6-2)
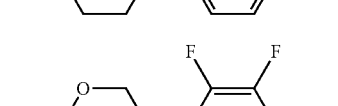

(6-3)
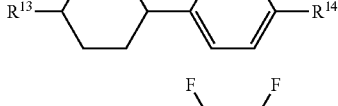

(6-4)
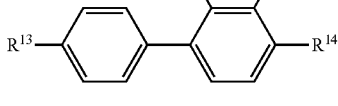

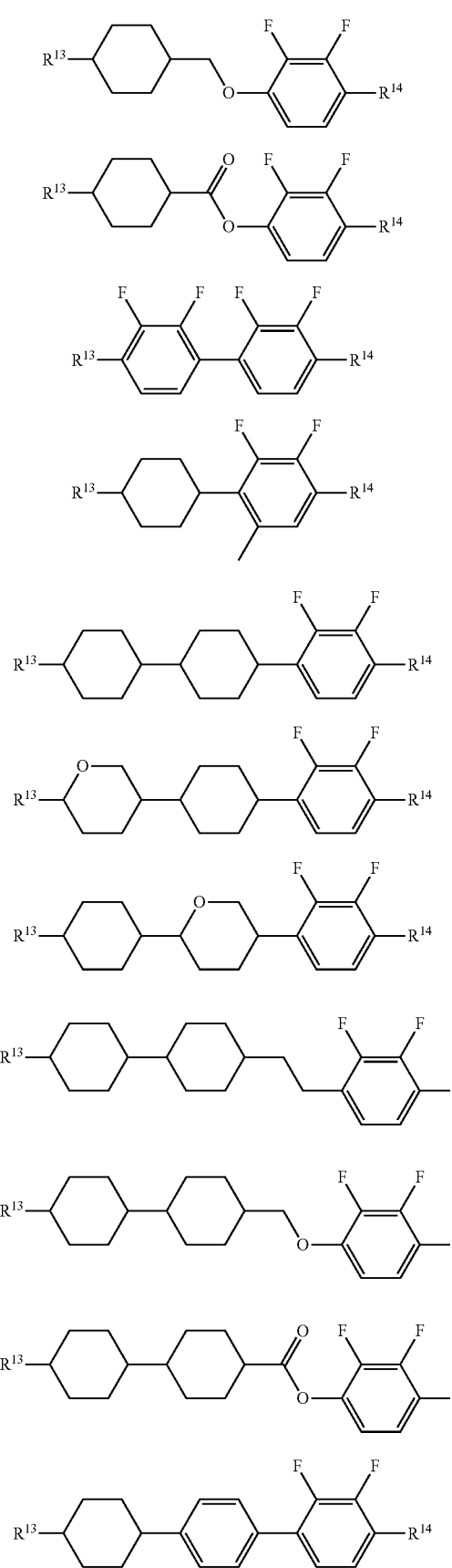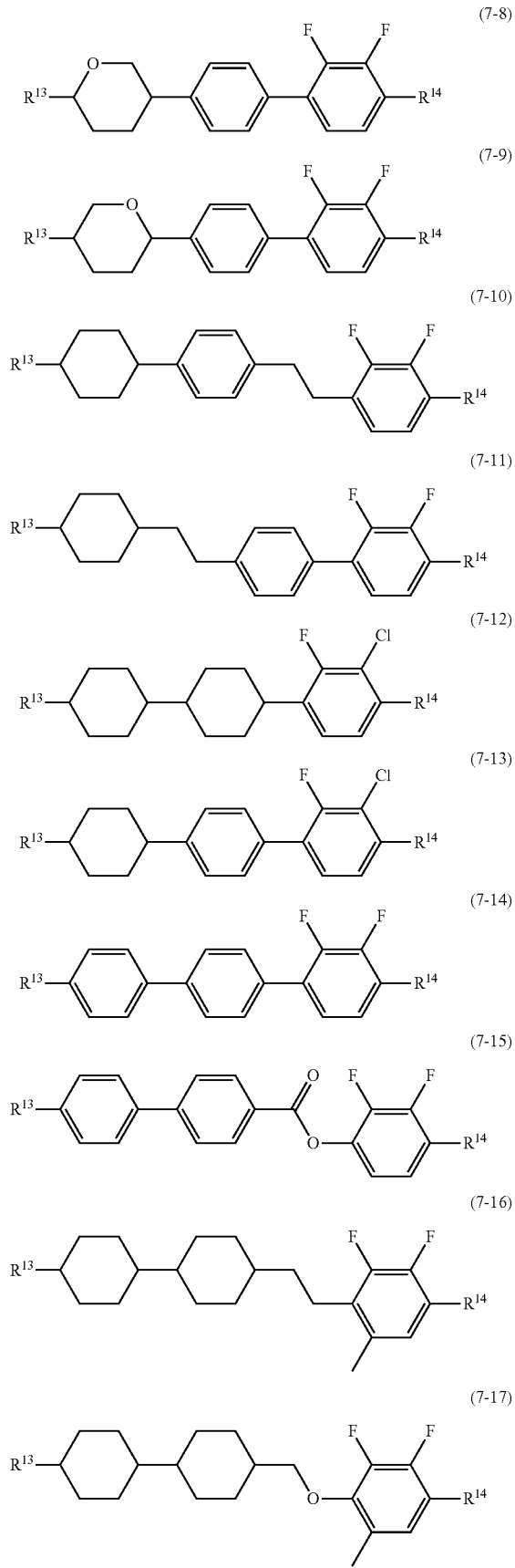

(8-1)
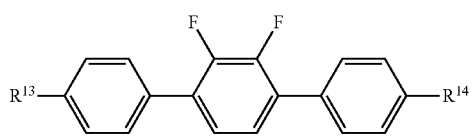

(9-1)
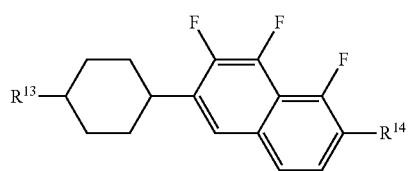

(9-2)
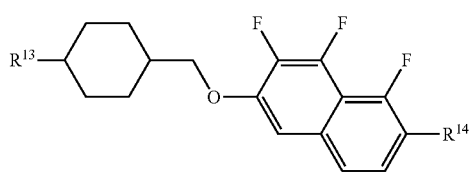

(9-3)
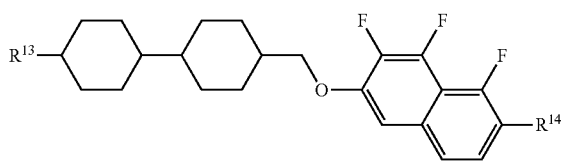

(10-1)
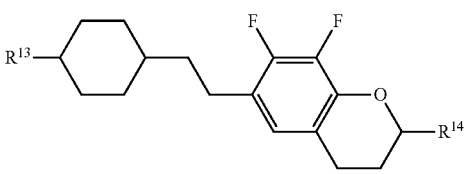

(10-2)
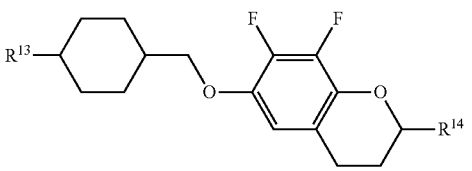

(10-3)
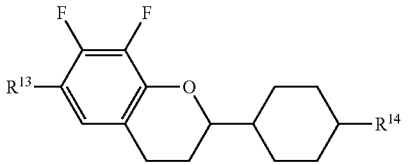

(10-4)
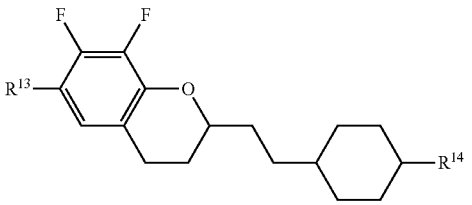

(10-5)
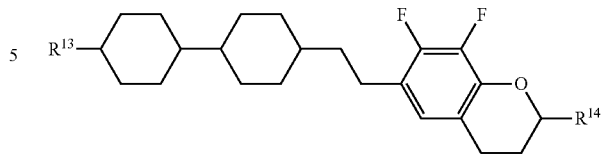

(10-6)
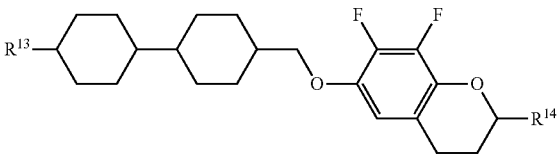

(10-7)
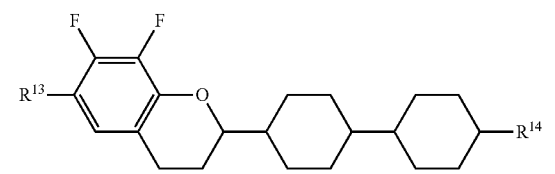

(10-8)
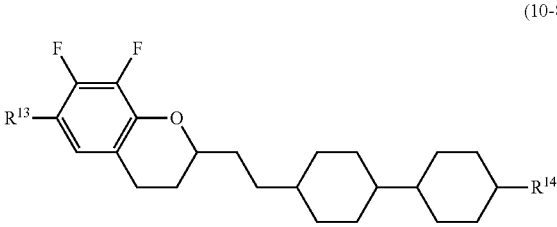

In the compounds (component D), $R^{13}$, $R^{14}$ and $R^{15}$ are defined in a manner identical with the definitions in the formulas (6) to (12).

Component D is a compound having negative dielectric anisotropy. Component D is mainly used when a composition for the VA mode or the PSA mode is prepared. Among types of component D, compound (6) is a bicyclic compound, and therefore is effective mainly in adjusting the viscosity, the optical anisotropy or the dielectric anisotropy. Compounds (7) and (8) are a tricyclic compound, and therefore effective in increasing the maximum temperature, the optical anisotropy or the dielectric anisotropy. Compounds (9) to (12) are effective in increasing the dielectric anisotropy.

When a composition for the VA mode or the PSA mode is prepared, a content of component D is preferably 40% by weight or more, and further preferably in the range of 50 to 95% by weight, based on the total weight of the composition. When component D is added to a composition having positive dielectric anisotropy, the content of component D is preferably 30% by weight or less based on the total weight of the composition. The elastic constant of the composition and the voltage-transmittance curve of the device can be adjusted by adding component D.

Component E is a compound in which two terminal groups are alkyl or the like. Preferred examples of component E include compounds (13-1) to (13-11), compounds (14-1) to (14-19) and compounds (15-1) to (15-7).

(13-1)

(13-2) 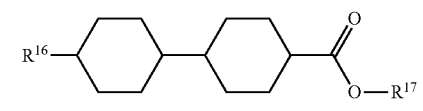
(13-3) 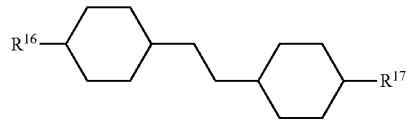
(13-4) 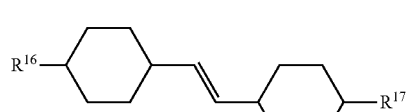
(13-5) 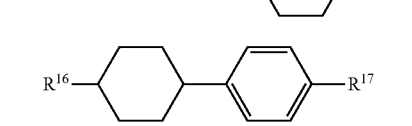
(13-6) 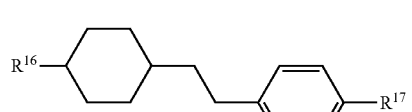
(13-7) 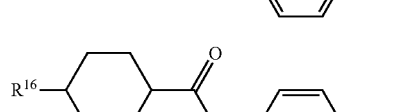
(13-8) 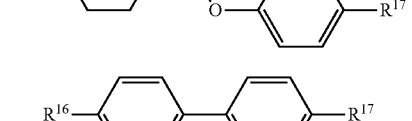
(13-9) 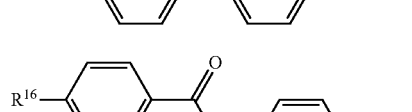
(13-10) 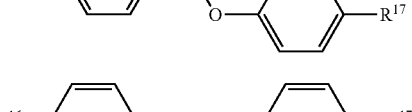
(13-11) 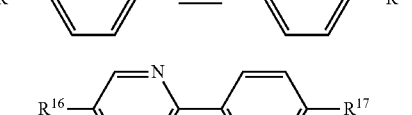
(14-1) 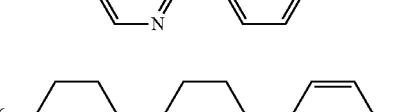
(14-2) 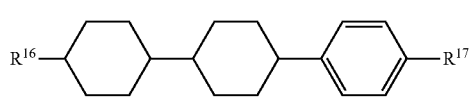
(14-3) 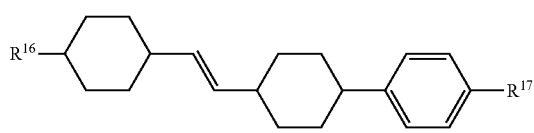
(14-4) 
(14-5) 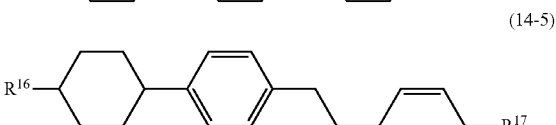
(14-6) 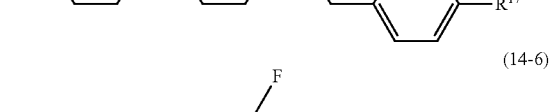
(14-7) 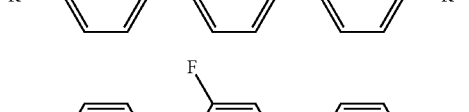
(14-8) 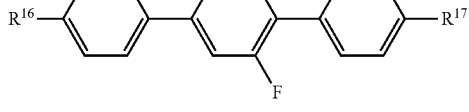
(14-9) 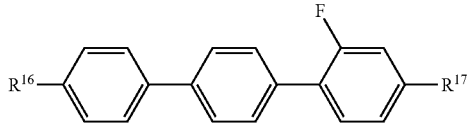
(14-10) 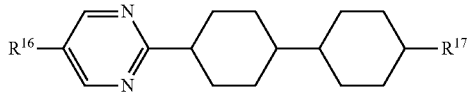
(14-11) 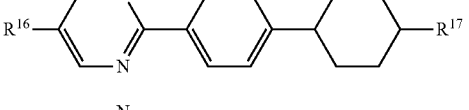
(14-12) 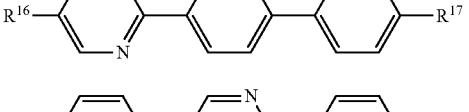
(14-13) 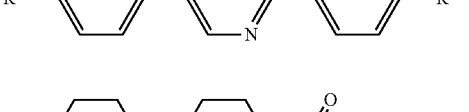
(14-14) 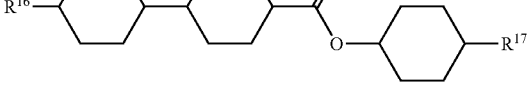
(14-15) 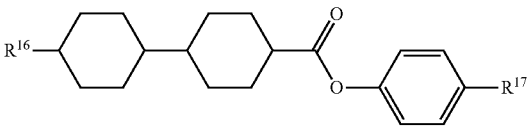

(14-16)
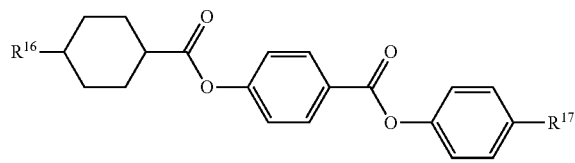

(14-17)
(14-18)
(14-19)
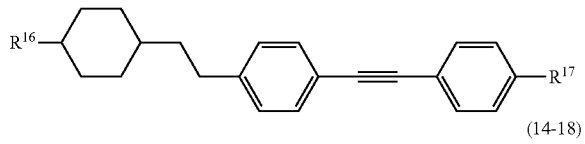

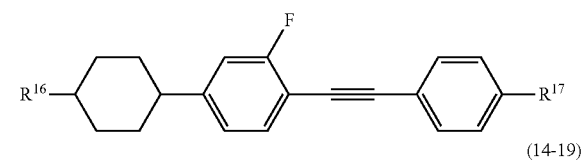

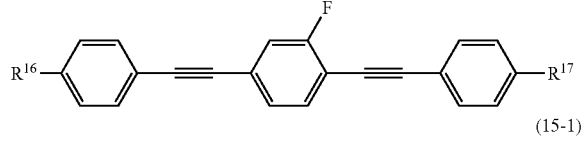

(15-1)
(15-2)
(15-3)
(15-4)
(15-5)
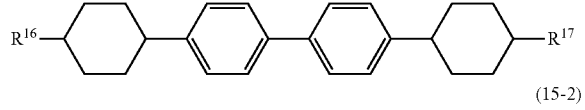

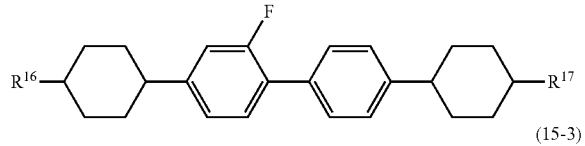

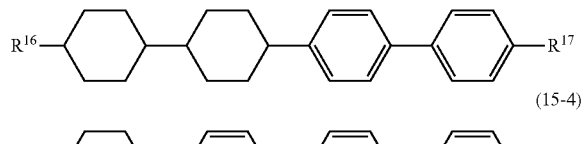

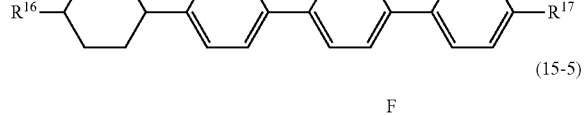

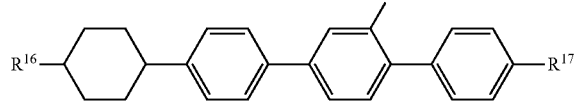

(15-6)
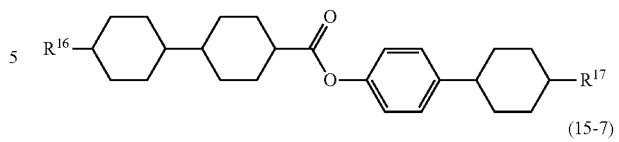

(15-7)
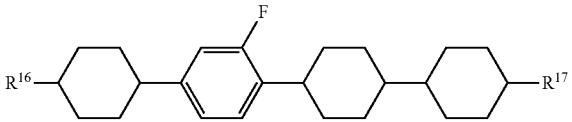

In the compounds (component E), $R^{16}$ and $R^{17}$ are defined in a manner identical with the definitions in the formulas (13) to (15).

Component E has a small absolute value of dielectric anisotropy, and therefore is a compound close to neutrality. Compound (13) is effective mainly in adjusting the viscosity or adjusting the optical anisotropy. Compound (14) and (15) are effective in extending the temperature range of the nematic phase by increasing the maximum temperature, or in adjusting the optical anisotropy.

When a content of component E is increased, the viscosity of the composition decreases, but the dielectric anisotropy also decreases. Thus, as long as a desired value of threshold voltage of the device is met, the content is preferably as large as possible. Accordingly, when a composition for the VA mode or the PSA mode is prepared, the content of component E is preferably 30% by weight or more, and further preferably 40% by weight or more, based on the total weight of the composition.

Composition (1) is prepared by a method of dissolving necessary components at a high temperature, or the like. According to an application, an additive may be added to the composition. Specific examples of the additive include an optically active compound, a polymerizable compound, a polymerization initiator, an antioxidant, an ultraviolet light absorber, a light stabilizer, a heat stabilizer and a defoaming agent. Such additives are well known to those skilled in the art, and described in literature.

Composition (1) may further contain at least one optically active compound. A publicly known chiral dopant can be added as the optically active compound. The chiral dopant is effective in inducing a helical structure in liquid crystal molecules to give a necessary twist angle, thereby preventing a reverse twist. Preferred examples of the chiral dopant include compounds (Op-1) to (Op-18) below. In compound (Op-18), ring J is 1,4-cyclohexylene or 1,4-phenylene, and $R^{24}$ is alkyl having 1 to 10 carbons.

(Op-1)
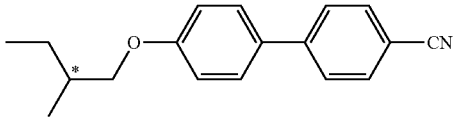

(Op-2)
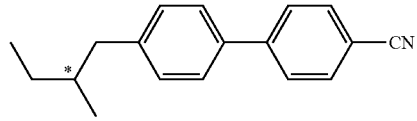

(Op-3)
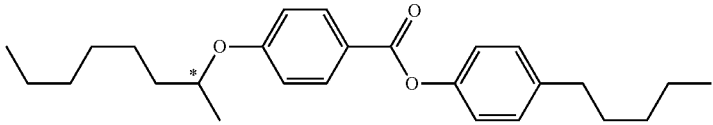

(Op-4)
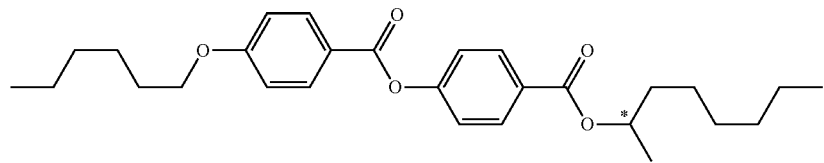
(Op-5)
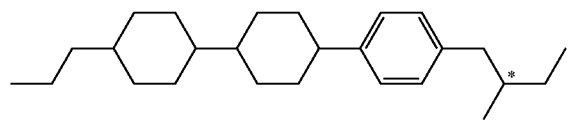
(Op-6)
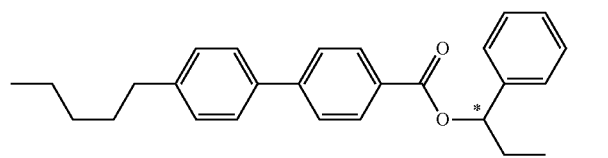
(Op-7)
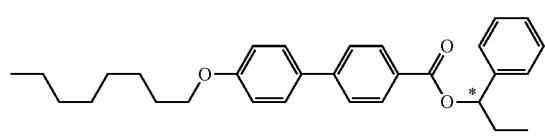
(Op-8)
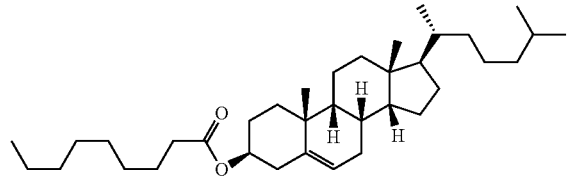
(Op-9)
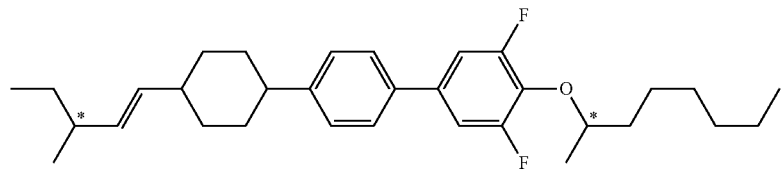
(Op-10)
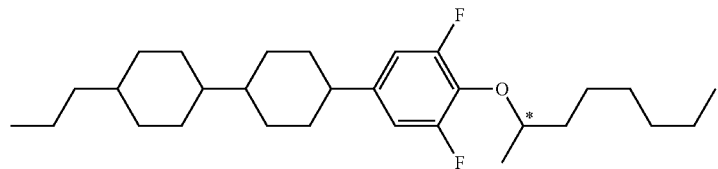
(Op-11)
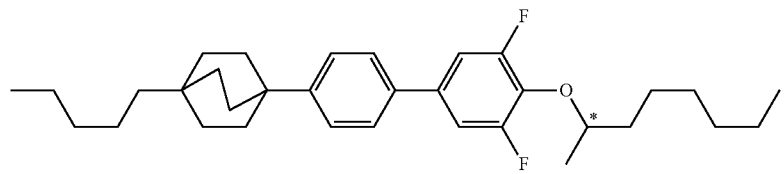
(Op-12)
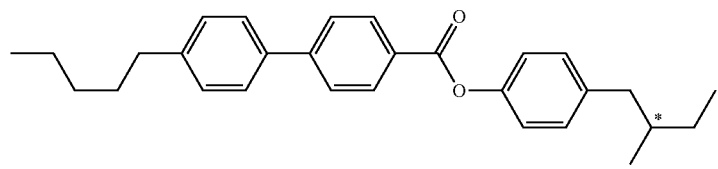
(Op-13)
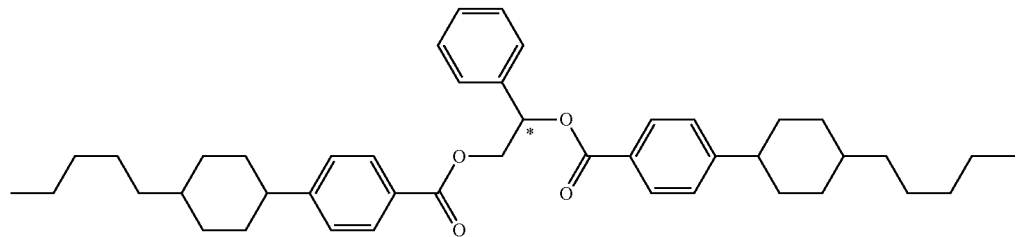

(Op-14) 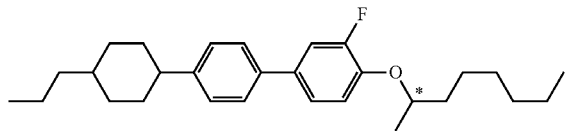

(Op-15) 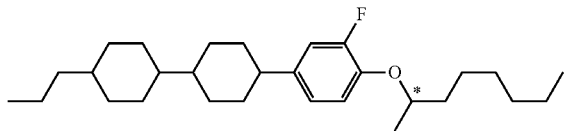

(Op-16) 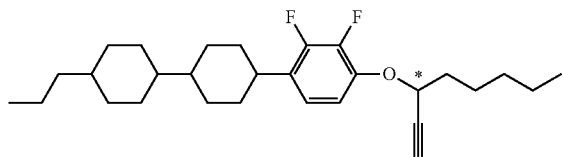

(Op-17) 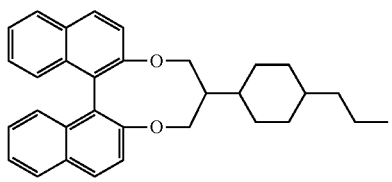

(Op-18) 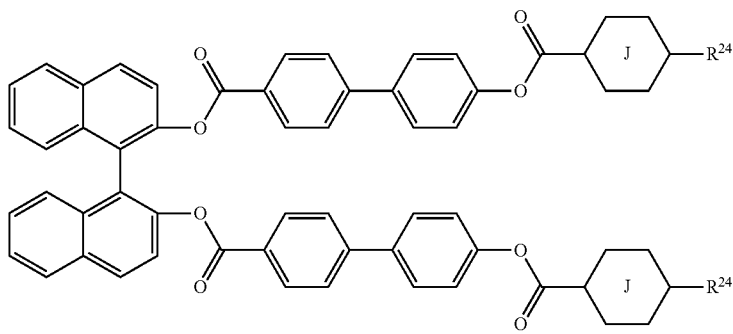

In composition (1), a helical pitch is adjusted by addition of such an optically active compound. The helical pitch is preferably adjusted to the range of 40 to 200 micrometers in a composition for the TFT mode and the TN mode. The helical pitch is preferably adjusted to the range of 6 to 20 micrometers in a composition for the STN mode. In the case of a composition for a BTN mode, the helical pitch is preferably adjusted to the range of 1.5 to 4 micrometers. Two or more optically active compounds may be added for the purpose of adjusting temperature dependence of the helical pitch.

Composition (1) can also be used for the PSA mode by adding the polymerizable compound. Specific examples of the polymerizable compound include acrylate, methacrylate, a vinyl compound, a vinyloxy compound, propenyl ether, an epoxy compound (oxirane, oxetane) and vinyl ketone, and preferred examples include compounds (M-1) to (M-12) described below. The polymerizable compound is polymerized by irradiation with ultraviolet light or the like. The compound may be polymerized in the presence of a suitable initiator such as a photopolymerization initiator. Suitable conditions for polymerization, suitable types of the initiator and suitable amounts thereof are known to those skilled in the art and are described in literature.

In compounds (M-1) to (M-12), $R^{20}$ is hydrogen or methyl; s is independently 0 or 1, respectively; and t and u are independently an integer from 1 to 10, respectively. A parenthesized symbol F stands for independently hydrogen or fluorine, respectively.

(M-1) 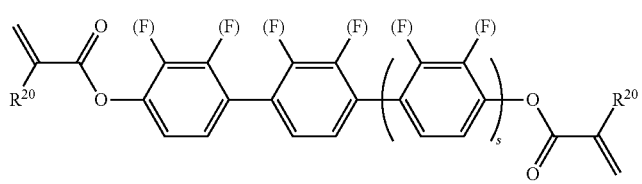

(M-2) 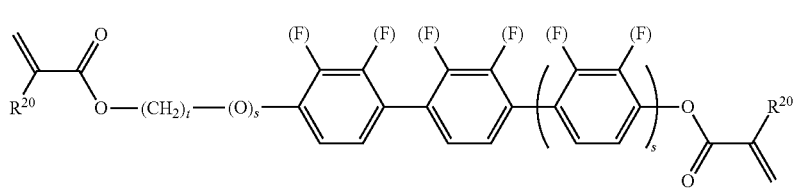

-continued
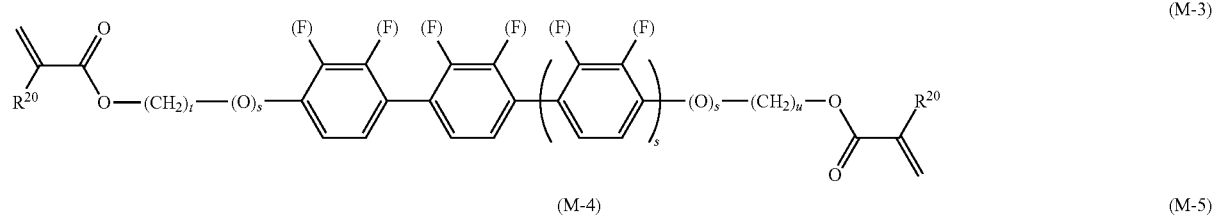
(M-3)
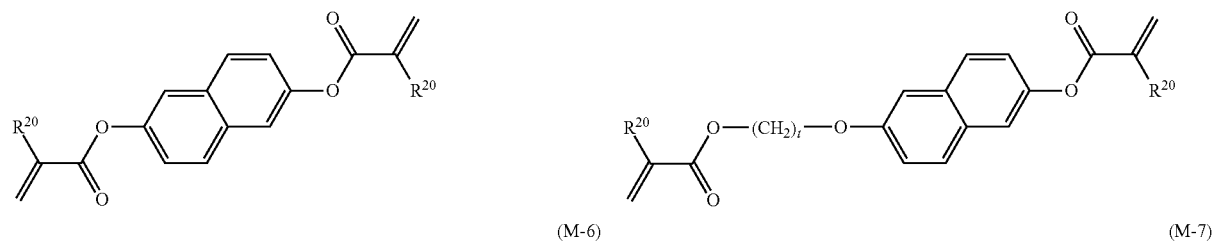
(M-4) (M-5)
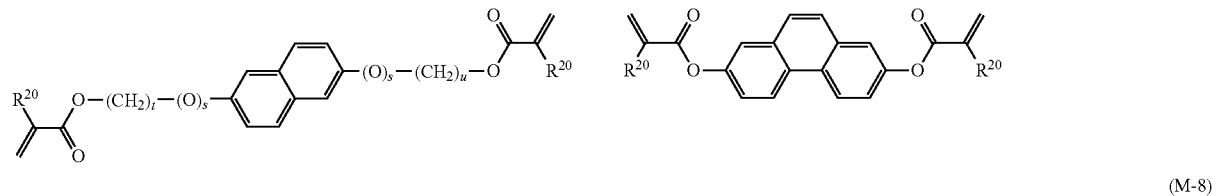
(M-6) (M-7)
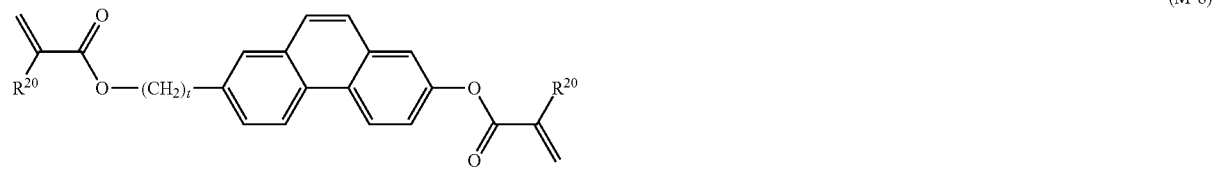
(M-8)
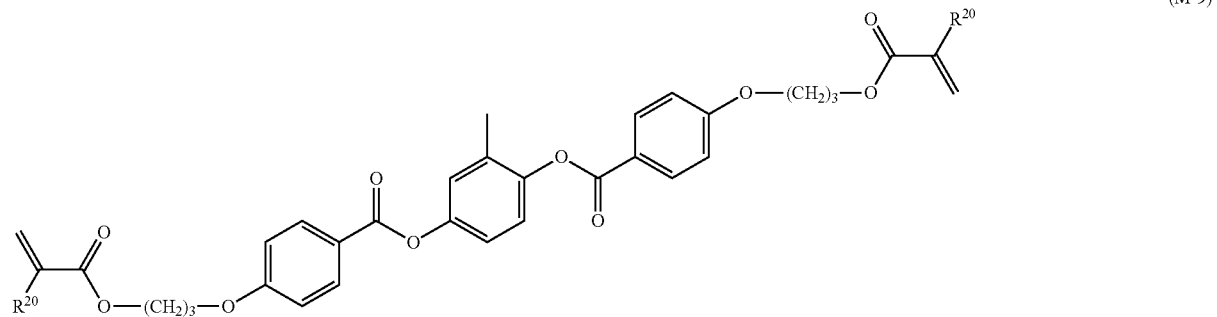
(M-9)
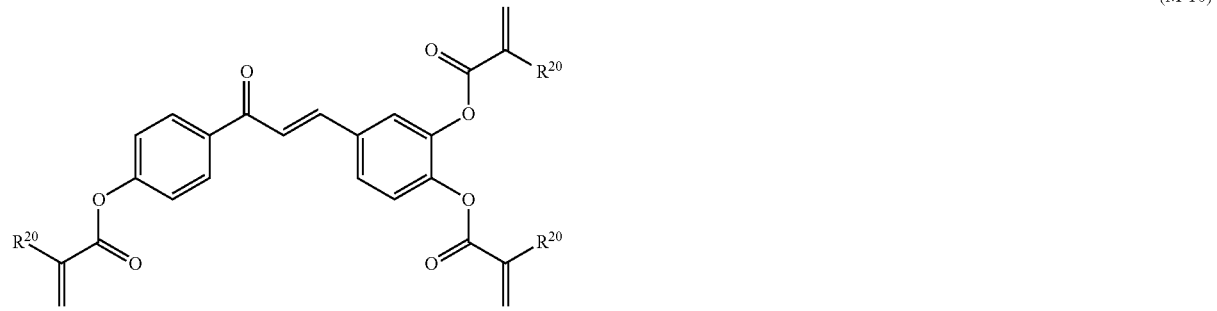
(M-10)
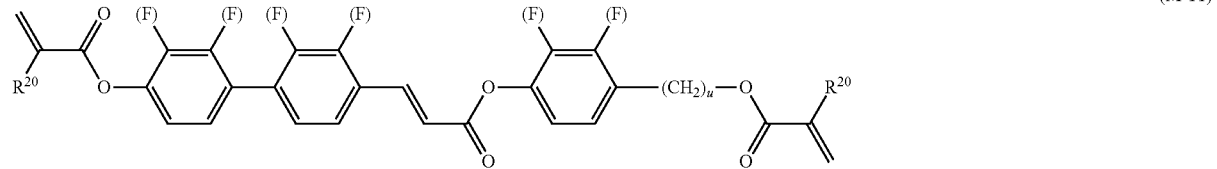
(M-11)

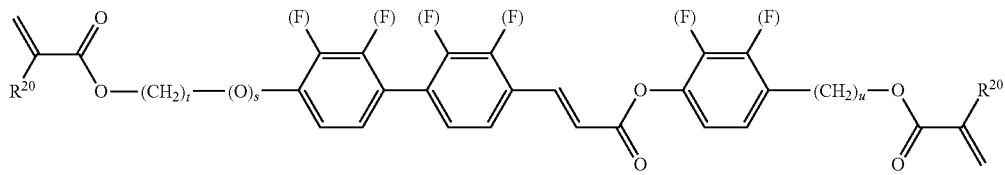

(M-12)

The antioxidant is effective for maintaining the large voltage holding ratio. Specific examples of a preferred antioxidant include compounds (AO-1) and (AO-2) described below; and IRGANOX 415, IRGANOX 565, IRGANOX 1010, IRGANOX 1035, IRGANOX 3114 and IRGANOX 1098 (trade names: BASF SE). The ultraviolet light absorber is effective for preventing a decrease of the maximum temperature. Specific examples of a preferred ultraviolet light absorber include a benzophenone derivative, a benzoate derivative and a triazole derivative. Specific examples include compounds (AO-3) and (AO-4) described below; TINUVIN 329, TINUVIN P, TINUVIN 326, TINUVIN 234, TINUVIN 213, TINUVIN 400, TINUVIN 328 and TINUVIN 99-2 (trade names: BASF SE); and 1,4-diazabicyclo[2.2.2]octane (DABCO).

The light stabilizer such as an amine having steric hindrance is preferred for maintaining the large voltage holding ratio. Specific examples of a preferred light stabilizer include compounds (AO-5) and (AO-6) described below; and TINUVIN 144, TINUVIN 765 and TINUVIN 770DF (trade names: BASF SE). The heat stabilizer is also effective for maintaining the large voltage holding ratio, and preferred examples include IRGAFOS 168 (trade name: BASF SE). The antifoaming agent is effective for preventing foam formation. Specific examples of a preferred antifoaming agent include dimethyl silicone oil and methylphenyl silicone oil.

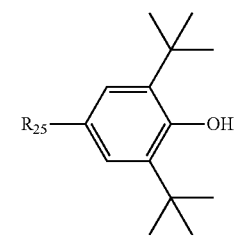
(AO-1)

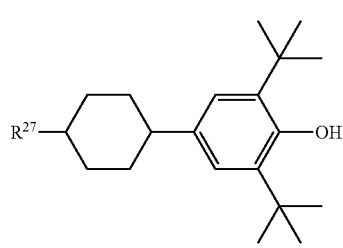
(AO-2)

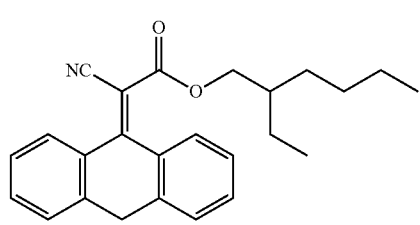
(AO-3)

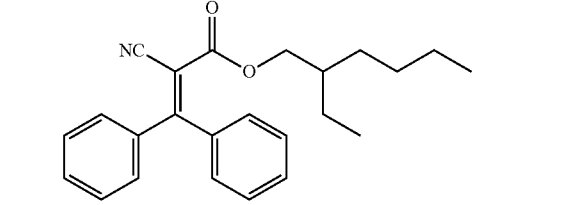
(AO-4)

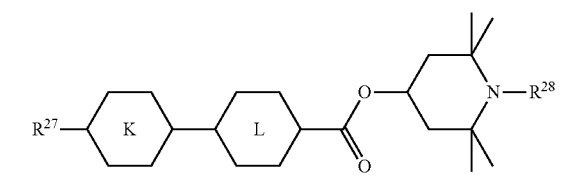
(AO-5)

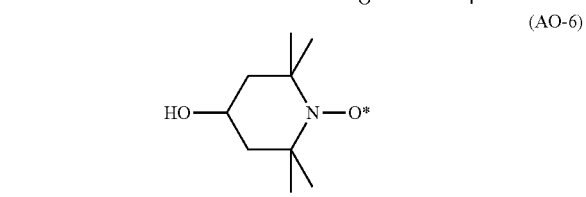
(AO-6)

In compound (AO-1), $R^{25}$ is alkyl having 1 to 20 carbons, alkoxy having 1 to 20 carbons, —COOR$^{26}$ or —CH$_2$CH$_2$COOR$^{26}$; wherein, $R^{26}$ is alkyl having 1 to 20 carbons. In compounds (AO-2) and (AO-5), $R^{27}$ is alkyl having 1 to 20 carbons. In compound (AO-5), ring K and ring L are 1,4-cyclohexylene or 1,4-phenylene, v is 0, 1 or 2, and $R^{28}$ is hydrogen, methyl or O'.

Composition (1) can be used for a guest host (GH) mode by addition of a dichroic dye of a merocyanine type, a styryl type, an azo type, an azomethine type, an azoxy type, a quinophthalone type, an anthraquinone type, a tetrazine type or the like.

In composition (1), the maximum temperature can be adjusted to be 70° C. or higher and the minimum temperature can be adjusted to be −10° C. or lower by suitably adjusting a kind and a proportion of component compounds, and therefore the temperature range of the nematic phase is wide. Accordingly, a liquid crystal display device including the composition can be used in the wide temperature range.

In composition (1), the optical anisotropy can be adjusted to the range of 0.10 to 0.13 or to the range of 0.05 to 0.18 by suitably adjusting a kind and a proportion of component compounds. In a similar manner, the dielectric anisotropy can be adjusted to the range of −5.0 to −2.0. Preferred dielectric anisotropy is in the range of −4.5 to −2.5. Composition (1) having dielectric anisotropy in the range can be preferably used in a liquid crystal display device that operates in the IPS mode, the VA mode or the PSA mode.

3. Liquid Crystal Display Device

Composition (1) can be used in an AM device. The composition can also be used in a PM device. The composition can also be used in the AM device and the PM device each having a mode such as the PC mode, the TN mode, the STN mode, the ECB mode, the OCB mode, the IPS mode, the FFS mode, the VA mode, the PSA and the FPA mode. Use in the AM device having the TN mode, the OCB mode, the IPS mode or the FFS mode is particularly preferred. In the AM device having the IPS mode or the FFS mode, alignment of liquid crystal molecules in a state in which no voltage is applied may be parallel or vertical to a panel substrate. The devices may be of a reflective type, a transmissive type or a transflective type. Use in the transmissive device is preferred. The composition can also be used in an amorphous silicon-TFT device or a polycrystal silicon-TFT device. The composition can also be used in a nematic curvilinear aligned phase (NCAP) device prepared by microencapsulating the composition and a polymer dispersed (PD) device in which a three-dimensional network-polymer is formed in the composition.

Composition (1) has negative dielectric anisotropy, and therefore can be suitably used in the liquid crystal display device having an operating mode such as the VA mode, the IPS mode or the PSA mode, and driven by the AM mode. The composition can be particularly suitably used in a liquid crystal display device having the VA mode, and driven by the AM mode.

In a liquid crystal display device that operates in the TN mode, the VA mode or the like, a direction of an electric field is vertical to a direction of a liquid crystal layer. On the other hand, in a liquid crystal display device that operates in the IPS mode or the like, the direction of the electric field is parallel to the direction of the liquid crystal layer. A structure of a liquid crystal display device that operates in the VA mode is reported in K. Ohmuro, S. Kataoka, T. Sasaki and Y. Koike, SID '97 Digest of Technical Papers, 28, 845 (1997). A structure of a liquid crystal display device that operates in the IPS mode is reported in WO 91/10936 A (family: U.S. Pat. No. 5,576,867 B).

EXAMPLES

The invention will be described in greater detail by way of Examples. However, the invention is not limited by the Examples.

1-1. Example of Compound (1)

Compound (1) was prepared according to procedures described below. The thus prepared compound was identified by methods such as an NMR analysis. Physical properties of the compound were measured by methods described below.

NMR Analysis

As a measuring apparatus, DRX-500 (made by Bruker BioSpin Corporation) was used. In $^1$H-NMR measurement, a sample was dissolved in a deuterated solvent such as $CDCl_3$, and measurement was carried out under conditions of room temperature, 500 MHz and 16 times of accumulation. Tetramethylsilane was used as an internal standard. In $^{19}$F-NMR measurement, $CFCl_3$ was used as an internal standard, and measurement was carried out under conditions of 24 times of accumulation. In explaining nuclear magnetic resonance spectra obtained, s, d, t, q, quin, sex and m stand for a singlet, a doublet, a triplet, a quartet, a quintet, a sextet and a multiplet, and br being broad, respectively.

Sample for Measurement

Upon measuring phase structure and a transition temperature, a liquid crystal compound itself was used as a sample. Upon measuring physical properties such as maximum temperature of a nematic phase, viscosity, optical anisotropy and dielectric anisotropy, a composition prepared by mixing the compound with a base liquid crystal was used as a sample.

When the sample prepared by mixing the compound with the base liquid crystal was used, measurement was carried out according to a method described below. The sample was prepared by mixing 15% by weight of the compound and 85% by weight of the base liquid crystal. Then, an extrapolated value was calculated from a measured value of the sample, according to an extrapolation method, represented by an equation below, and the value was described: [extrapolated value]=(100×[measured value of a sample]−[% by weight of a base liquid crystal]×[measured value of the base liquid crystal])/[% by weight of a compound].

When crystals (or a smectic phase) precipitated at 25° C. even at the ratio of the compound to the base liquid crystal, a ratio of the compound to the base liquid crystal was changed in the order of (10% by weight:90% by weight), (5% by weight:95% by weight) and (1% by weight:99% by weight), and physical properties of the sample at a ratio at which no crystals (or no smectic phase) precipitated at 25° C. were measured. In addition, unless otherwise noted, the ratio of the compound to base liquid crystal was 15% by weight:85% by weight.

As the base liquid crystal, base liquid crystal (i) described below was used. A proportion of the components of base liquid crystal (i) are expressed in terms of weight percent (% by weight).

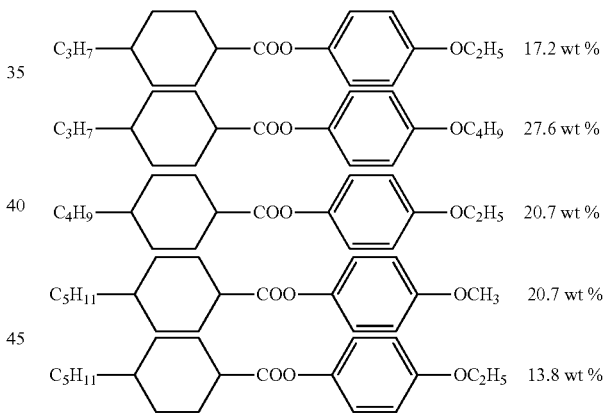

Measuring Method

Physical properties were measured according to methods described below. Most of the measuring methods are applied as described in the Standard of Japan Electronics and Information Technology Industries Association (hereinafter abbreviated as JEITA) (JEITA ED-2521A) discussed and established by JEITA, or modified thereon. No TFT was attached to a TN device used for measurement.

(1) Phase Structure

A sample was placed on a hot plate in a melting point apparatus (FP52 Hot Stage made by Mettler-Toledo International Inc.) equipped with a polarizing microscope, and a state of a phase and a change thereof were observed with the polarizing microscope while the sample was heated at a rate of 3° C. per minute, and a kind of the phase was specified.

(2) Transition Temperature (° C.)

A sample was heated and then cooled at a rate of 3° C. per minute using a differential scanning calorimeter, DSC-7

System or Diamond DSC System, made by PerkinElmer, Inc., and a starting point of an endothermic peak or an exothermic peak caused by a phase change of the sample was determined by extrapolation, and thus a transition temperature was determined. Temperature at which a compound undergoes transition from a solid to a liquid crystal phase such as the smectic phase and the nematic phase may be occasionally abbreviated as "minimum temperature of the liquid crystal phase." Temperature at which the compound undergoes transition from the liquid crystal phase to liquid may be occasionally abbreviated as "clearing point."

A crystal was expressed as C. When kinds of the crystals were distinguishable, each of the crystals was expressed as $C_1$ or $C_2$. The smectic phase or the nematic phase was expressed as S or N. When smectic A phase, smectic B phase, smectic C phase or smectic F phase was distinguishable among the smectic phases, the phases were expressed as $S_A$, $S_B$, $S_C$ or $S_F$, respectively. A liquid (isotropic) was expressed as I. A transition temperature was expressed as "C 50.0 N 100.0 I," for example. The expression indicates that a transition temperature from the crystals to the nematic phase is 50.0° C., and a transition temperature from the nematic phase to the liquid is 100.0° C.

(3) Compatibility at Low Temperature:

Samples in which the base liquid crystal and the compound were mixed for proportions of the compounds to be 20% by weight, 15% by weight, 10% by weight, 5% by weight, 3% by weight and 1% by weight were prepared, and put in glass vials. After the glass vials were kept in freezers at −10° C. or −20° C. fora predetermined period of time, whether or not crystals (or a smectic phase) precipitated was observed.

(4) Maximum Temperature of Nematic Phase ($T_{NI}$ or NI; ° C.)

A sample was placed on a hot plate in a melting point apparatus equipped with a polarizing microscope, and heated at a rate of 1° C. per minute. Temperature when part of the sample began to change from a nematic phase to an isotropic liquid was measured. A maximum temperature of the nematic phase may be occasionally abbreviated as "maximum temperature." When the sample was a mixture of a compound and the base liquid crystal, the maximum temperature was expressed in terms of a symbol TNI. When the sample was a mixture of a compound and component B and so forth, the maximum temperature was expressed in terms of a symbol NI.

(5) Minimum Temperature of Nematic Phase ($T_C$; ° C.)

Samples each having a nematic phase were kept in freezers at temperatures of 0° C., −10° C., −20° C., −30° C. and −40° C. for 10 days, and then liquid crystal phases were observed. For example, when the sample was maintained in the nematic phase at −20° C. and changed to crystals or a smectic phase at −30° C., Tc was expressed as $T_c \leq -20°$ C. A minimum temperature of the nematic phase may be occasionally abbreviated as "minimum temperature."

(6) Viscosity (Bulk Viscosity; η; Measured at 20° C.; mPa·s)

A cone-plate (E-type) rotational viscometer was used for measurement.

(7) Viscosity (Rotational Viscosity; γ1; Measured at 25° C.; mPa·s)

Measurement was carried out according to a method described in M. Imai et al., Molecular Crystals and Liquid Crystals, Vol. 259, p. 37 (1995). A sample was put in a VA device in which a distance (cell gap) between two glass substrates was 20 micrometers. Voltage was applied stepwise to the device in the range of 30 V to 50 V at an increment of 1 V. After a period of 0.2 second with no voltage application, voltage was repeatedly applied under conditions of only one rectangular wave (rectangular pulse; 0.2 second) and no voltage application (2 seconds). A peak current and a peak time of transient current generated by the applied voltage were measured. A value of rotational viscosity was obtained from the measured values and calculation equation (8) described on page 40 of the paper presented by M. Imai et al. In dielectric anisotropy required for the calculation, a value measured according to items of dielectric anisotropy described below was used.

(8) Optical Anisotropy (Refractive Index Anisotropy; Measured at 25° C.; Δn)

Measurement was carried out by an Abbe refractometer with a polarizing plate mounted on an ocular, using light at a wavelength of 589 nanometers. A surface of a main prism was rubbed in one direction, and then a sample was added dropwise onto the main prism. A refractive index (n∥) was measured when a direction of polarized light was parallel to a direction of rubbing. A refractive index (n⊥) was measured when the direction of polarized light was perpendicular to the direction of rubbing. A value of optical anisotropy (Δn) was calculated from an equation: Δn=n∥ −n⊥.

(9) Dielectric Anisotropy (Δε; Measured at 25° C.)

A value of dielectric anisotropy was calculated from an equation: Δε=ε∥−ε⊥. A dielectric constant (ε∥ and ε⊥) was measured as described below.

(1) Measurement of dielectric constant (ε∥): An ethanol (20 mL) solution of octadecyltriethoxysilane (0.16 mL) was applied to a well-cleaned glass substrate. After rotating the glass substrate with a spinner, the glass substrate was heated at 150° C. for 1 hour. A sample was put in a VA device in which a distance (cell gap) between two glass substrates was 4 micrometers, and the device was sealed with an ultraviolet-curable adhesive. Sine waves (0.5V, 1 kHz) were applied to the device, and after 2 seconds, a dielectric constant (ε∥) of liquid crystal molecules in a major axis direction was measured.

(2) Measurement of dielectric constant (ε⊥): A polyimide solution was applied to a well-cleaned glass substrate. After calcining the glass substrate, rubbing treatment was applied to the alignment film obtained. A sample was put in a TN device in which a distance (cell gap) between two glass substrates was 9 micrometers and a twist angle was 80 degrees. Sine waves (0.5 V, 1 kHz) were applied to the device, and after 2 seconds, a dielectric constant (ε⊥) of liquid crystal molecules in a minor axis direction was measured.

(10) Elastic Constant ($K_{11}$ and $K_{33}$; Measured at 25° C.; pN)

For measurement, Elastic Constant Measurement System Model EC-1 made by TOYO Corporation was used. A sample was put in a vertical alignment device in which a distance (cell gap) between two glass substrates was 20 micrometers. An electric charge of 20 V to 0 V was applied to the device, and electrostatic capacity and applied voltage were measured. Values of electrostatic capacity (C) and applied voltage (V) were fitted to equation (2.98) and equation (2.101) on page 75 of "Liquid Crystal Device Handbook" (Ekisho Debaisu Handobukku in Japanese; Nikkan Kogyo Shimbun, Ltd.), and a value of elastic constant was obtained from equation (2.100).

(11) Threshold Voltage (Vth; Measured at 25° C.; V)

For measurement, an LCD-5100 luminance meter made by Otsuka Electronics Co., Ltd. was used. A light source was a halogen lamp. A sample was put in a normally black mode VA device in which a distance (cell gap) between two glass substrates was 4 micrometers and a rubbing direction was anti-parallel, and the device was sealed with an ultraviolet-curable adhesive. A voltage (60 Hz, rectangular waves) to be applied to the device was stepwise increased from 0 V to 20 V at an increment of 0.02 V. On the occasion, the device was irradiated with light from a direction perpendicular to the device, and an amount of light transmitted through the device was measured. A voltage-transmittance curve was prepared, in which the maximum amount of light corresponds to 100% transmittance and the minimum amount of light corresponds to 0% transmittance. A threshold voltage is expressed in terms of a voltage at 10% transmittance.

(12) Voltage Holding Ratio (VHR-1; Measured at 25° C.; %)

A TN device used for measurement has a polyimide alignment film, and a distance (cell gap) between two glass substrates is 5 micrometers. A sample was put in the device, and then the device was sealed with an ultraviolet-curable adhesive. A pulse voltage (60 microseconds at 5 V) was applied to the TN device and the device was charged. A decaying voltage was measured for 16.7 milliseconds with a high-speed voltmeter, and area A between a voltage curve and a horizontal axis in a unit cycle was determined. Area B is an area without decay. A voltage holding ratio is a percentage of area A to area B.

(13) Voltage Holding Ratio (VHR-2; Measured at 80° C.; %)

A TN device used for measurement had a polyimide alignment film, and a distance (cell gap) between two glass substrates is 5 micrometers. A sample was put in the device, and then the device was sealed with an ultraviolet-curable adhesive. A pulse voltage (60 microseconds at 5 V) was applied to the TN device and the device was charged. A decaying voltage was measured for 16.7 milliseconds with a high-speed voltmeter, and area A between a voltage curve and a horizontal axis in a unit cycle was determined. Area B is an area without decay. A voltage holding ratio is a percentage of area A to area B.

Raw Material

Solmix A-11 (registered trademark) is a mixture of ethanol (85.5% by weight), methanol (13.4% by weight) and isopropanol (1.1% by weight), and was purchased from Japan Alcohol Trading Co., Ltd.

Example 1

Synthesis of Compound (No. 18)

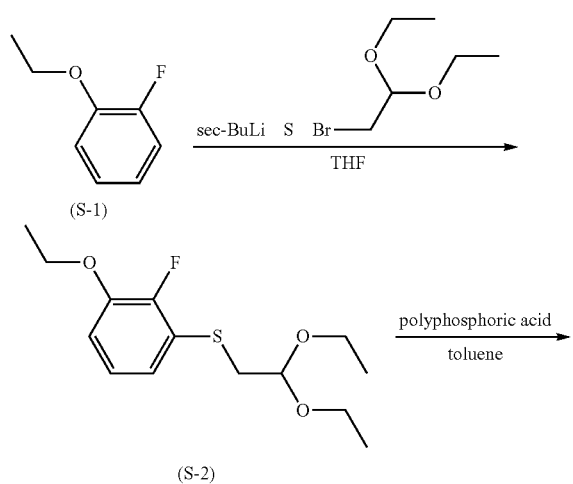

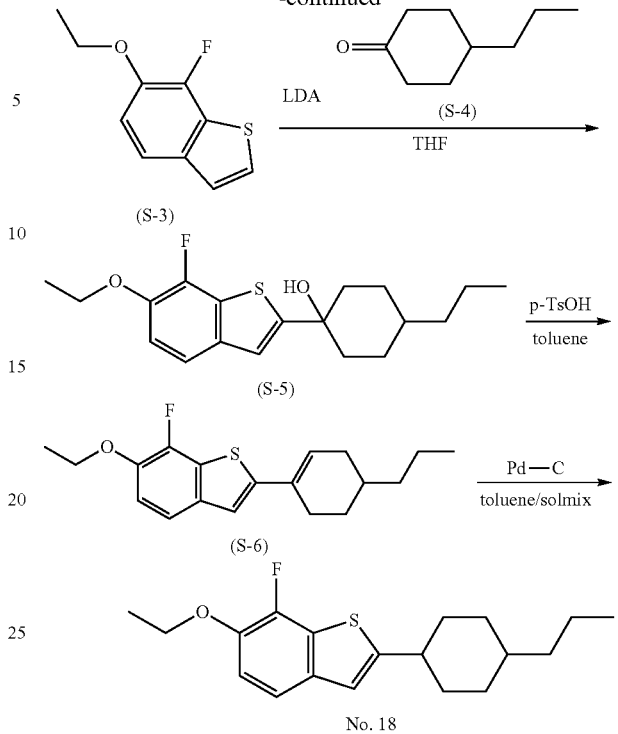

First Step

Under a nitrogen atmosphere, compound (S-1) (40 g) and THF (300 mL) were put in a reaction vessel, and the resulting mixture was cooled down to −74° C. Thereto, sec-butyl lithium (1 M; n-hexane, a cyclohexane solution; 313 mL) was added dropwise, and further the resulting mixture was stirred for 2 hours. Subsequently, sulfur powder (11.8 g) was added thereto and stirred for 2 hours while returning the resulting mixture to 25° C. Then, bromoacetaldehyde diethyl acetal (84 g) was added thereto, and subjected to reflux for 2 hours. A reaction mixture was poured into water, and the resulting reaction mixture was subjected to extraction with toluene. An organic layer was washed with water, and dried over anhydrous magnesium sulfate. The resulting solution was concentrated under reduced pressure, and a residue was purified by silica gel chromatography (toluene) to obtain compound (S-2) (31 g).

Second Step

Under a nitrogen atmosphere, compound (S-2) (31 g), polyphosphoric acid (150 g) and toluene (250 mL) were put in a reaction vessel, and subjected to reflux under heating for 3 hours. A reaction mixture was poured into water, and the resulting reaction mixture was subjected to extraction with toluene. An organic layer was washed with water, and dried over anhydrous magnesium sulfate. The resulting solution was concentrated under reduced pressure, and a residue was purified by silica gel chromatography (toluene:heptane=2:3 in a volume ratio) to obtain compound (S-3) (12.9 g).

Third Step

Under a nitrogen atmosphere, compound (S-3) (6 g) and THF (100 mL) were put in a reaction vessel, and the resulting mixture was cooled down to −74° C. Thereto, LDA (1 M; n-hexane, a THF solution; 37 mL) was added dropwise, and further the resulting mixture was stirred for 2 hours. Subsequently, compound (S-4) (6 g) was added thereto and stirred for 2 hours while returning the resulting mixture to 25° C. A reaction mixture was poured into water, and the resulting reaction mixture was subjected to extraction with toluene. An organic layer was washed with water, and dried over anhydrous magnesium sulfate to obtain compound (S-5). After then, a dehydration under adding p-toluenesulfonic acid thereto was performed according to a publicly known method described in the above scheme and to give compound (S-6), and a hydrogenation reaction and purification were performed with palladium carbon to obtain compound (No. 18). (1.7 g). In addition, if referring to Example described in WO 2009150966 A or the like, the dehydration and the hydrogenation reaction performed herein are easy to be implemented.

$^1$H-NMR (δ ppm; CDCl$_3$): 7.32 (d, 1H), 7.03 (t, 1H), 6.91 (d, 1H), 4.17 (q, 2H), 2.78 (tt, 1H), 2.12 (dd, 2H), 1.88 (dd, 2H), 1.60-1.20 (m, 10H), 0.91 (t, 3H).

Physical properties of compound (No. 18) were as described below. Transition temperature: C 68.4 N 86.0 I. T$_{NI}$=83.9° C.; Δn=0.153; Δε=−3.12; η=31.2 mPa·s.

Example 2

Synthesis of Compound (No. 41)

In Example 1, compound (No. 41) was obtained by using compound (S-7) in place of compound (S-4).

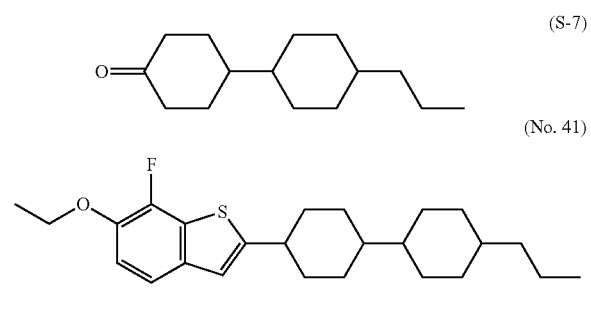

$^1$H-NMR (δ ppm; CDCl$_3$): 7.32 (d, 1H), 7.02 (t, 1H), 6.99 (d, 1H), 4.16 (q, 2H), 2.75 (tt, 1H), 2.13 (dd, 2H), 1.85 (d, 2H), 1.74 (t, 4H), 1.60-1.20 (m, 18H), 0.88 (t, 3H).

Physical properties of compound (No. 41) were as described below. Transition temperature: C 95.3 N 260.7 I. T$_{NI}$=210.6° C.; Δn=0.167; Δε=−3.29; η=53.4 mPa·s.

Example 3

Synthesis of Compound (No. 43)

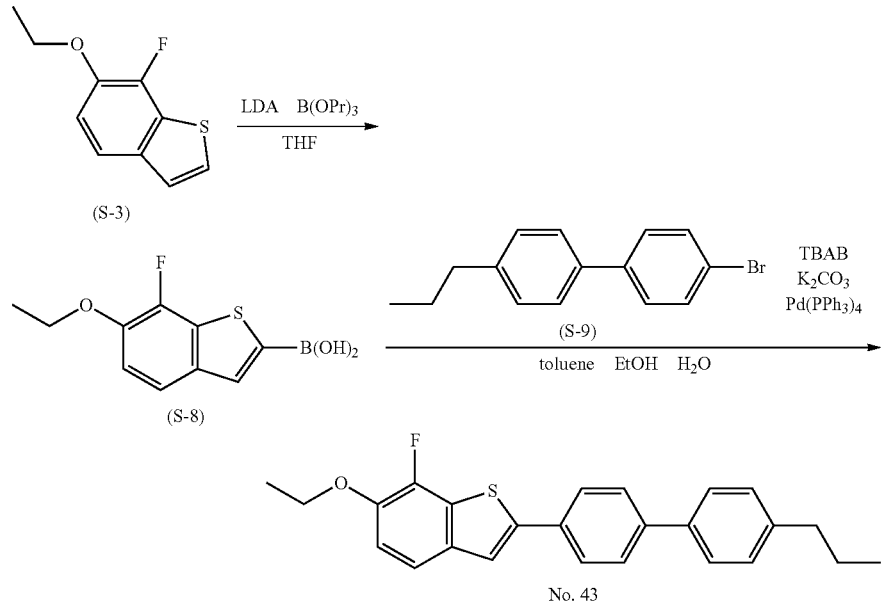

First Step

Under a nitrogen atmosphere, compound (S-3) (3 g) and THF (100 mL) were put in a reaction vessel, and the resulting mixture was cooled down to −74° C. Thereto, lithium diisopropylamide (1 M; an n-hexane solution; 18.34 mL) was added dropwise in a temperature range of −74° C. to −70° C., and further the resulting mixture was stirred for 2 hours. Subsequently, a THF (10 mL) solution of triisobutyl borate (4.02 g) was added thereto in a temperature range of −75° C. to −70° C., and stirred for 8 hours while returning the resulting mixture to 25° C. A reaction mixture was poured into hydrochloric acid aqueous solution, and the resulting reaction mixture was subjected to extraction with ethyl acetate. A combined organic layer was washed with water, saturated aqueous solution of sodium hydrogencarbonate and water, and dried over anhydrous magnesium sulfate. The resulting solution was concentrated under reduced pressure to obtain compound (S-8) (1.9 g).

Second Step

Then, compound (S-8) (1.3 g) and compound (S-9) (1.8 g) were dissolved in toluene, and water, ethanol, Pd(PPh$_3$)$_4$ (0.6 g), TBAB (0.17 g) and potassium carbonate (2.2 g) were added thereto, and the resulting mixture was refluxed under heating for 6 hours. After completion of the reaction, the resulting mixture was subjected to extraction with toluene, and washed with water, and then dried over anhydrous magnesium sulfate and concentrated under reduced pressure to obtain a light brown solid. The resulting solid was formed into a solution, and subjected to silica gel column chromatography (heptane:toluene=3:2 in a volume ratio) and recrystallization (ethanol) to obtain compound (No. 43) as a colorless crystal (1.5 g).

$^1$H-NMR (δ ppm; CDCl$_3$): 7.73 (d, 2H), 7.64 (d, 2H), 7.55 (d, 2H), 7.48 (d, 1H), 7.44 (d, 1H), 7.27 (d, 2H), 7.07 (t, 1H), 4.20 (q, 2H), 2.63 (t, 2H), 1.69 (sex, 2H), 1.47 (t, 3H), 0.98 (t, 3H).

Physical properties of compound (No. 43) were as described below. Transition temperature: C 205.9 S 265.6 N 295.5 I. $T_{NI}$=224.6° C.; Δn=0.587; Δε=−5.47; η=109.6 mPa·s. In addition, the sample for measurement was prepared from 1% by weight of compound (No. 43) and 99% by weight of base liquid crystal (i).

Example 4

Synthesis of Compound (No. 9)

In Example 3, compound (No. 9) was obtained by using compound (S-10) in place of compound (S-9).

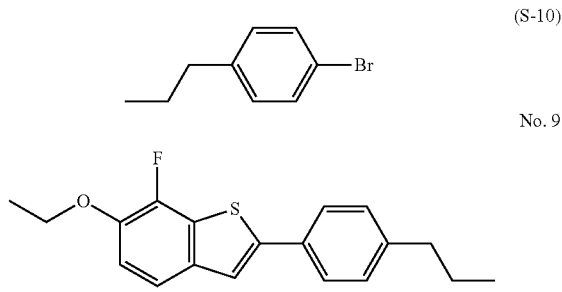

$^1$H-NMR (δ ppm; CDCl$_3$): 7.59 (d, 2H), 7.43 (d, 1H), 7.41 (d, 1H), 7.23 (d, 2H), 7.07 (t, 1H), 4.20 (q, 2H), 2.62 (t, 2H), 1.67 (sex, 2H), 1.47 (t, 3H), 0.97 (t, 3H).

Physical properties of compound (No. 9) were as described below. Transition temperature: C 89.5 N 99.4 I. $T_{NI}$=101.9° C.; Δn=0.287; Δε=−3.83; η=38.8 mPa·s.

Example 5

Synthesis of Compound (No. 25)

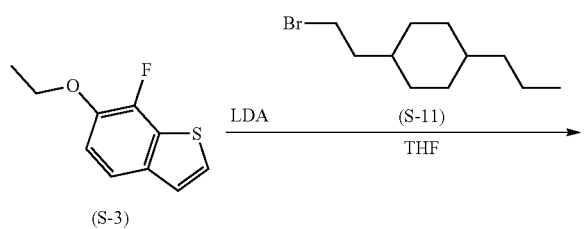

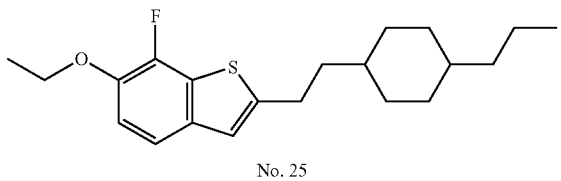

No. 25

First Step

Under a nitrogen atmosphere, compound (S-3) (3 g) and THF (100 mL) were put in a reaction vessel, and the resulting mixture was cooled down to −74° C. Thereto, lithium diisopropylamide (1 M; n-hexane solution; 16.82 mL) was added dropwise in a temperature range of −74° C. to −70° C., and further the resulting mixture was stirred for 2 hours. Subsequently, a THF (10 mL) solution of compound (S-11) (4.99 g) was added dropwise thereto in a temperature range of −75° C. to −70° C., and stirred for 8 hours while returning the resulting mixture to 25° C. A reaction mixture was poured into water, and the resulting reaction mixture was subjected to extraction with toluene, and washed with water, and then dried over anhydrous magnesium sulfate and concentrated under reduced pressure to obtain a light brown solid. The resulting material was subjected to silica gel column chromatography (heptane:toluene=3:1 in a volume ratio) and recrystallization (ethanol) to obtain compound (No. 25) as a colorless crystal (3.15 g).

$^1$H-NMR (δ ppm; CDCl$_3$): 7.28 (d, 1H), 7.02 (t, 1H), 6.89 (d, 1H), 4.16 (q, 2H), 2.87 (t, 2H), 1.79 (d, 2H), 1.73 (d, 2H), 1.62 (q, 2H), 1.44 (t, 3H), 1.35-0.79 (m, 10H), 0.88 (t, 3H).

Physical properties of compound (No. 25) were as described below. Transition temperature: C 88.2 I. $T_{NI}$=59.9° C.; Δn=0.133; Δε=−3.16; η=38.7 mPa·s.

Example 6

Synthesis of Compound (No. 105)

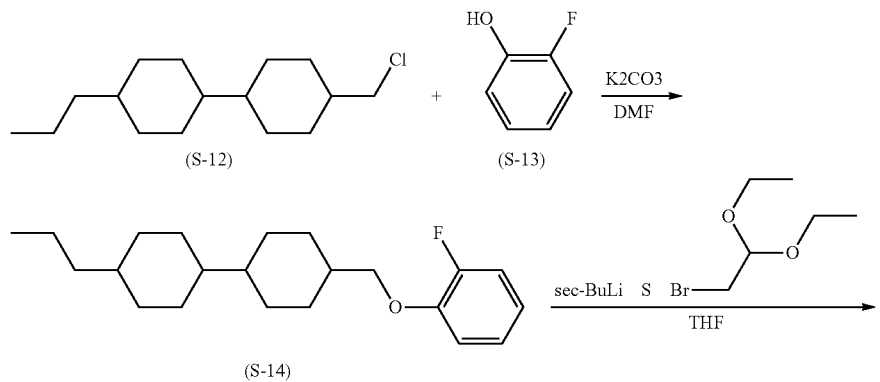

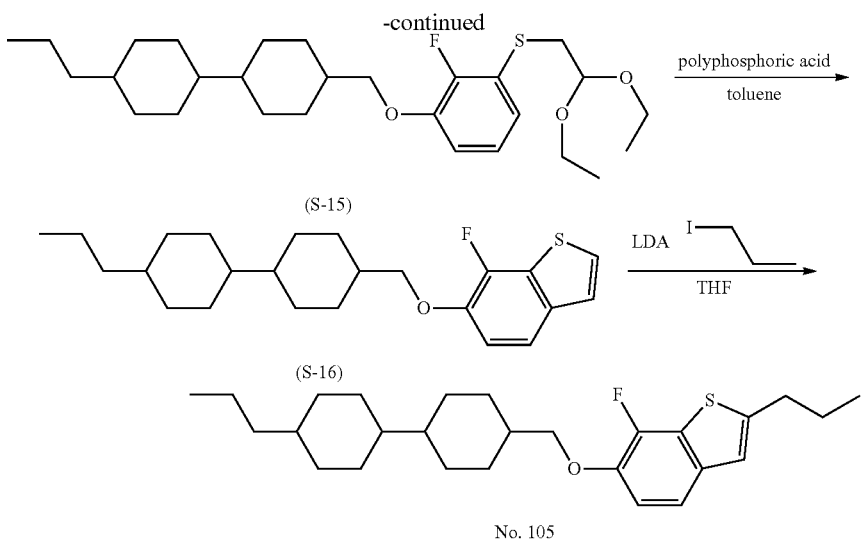

First Step

Under a nitrogen atmosphere, compound (S-12) (22.9 g), (S-13) (10.0 g), potassium carbonate (K₂CO₃; 18.5 g) and DMF (150 mL) were put in a reaction vessel, and the resulting mixture was stirred for 2 hours at 100° C. A reaction mixture was cooled to 25° C., and then a precipitate was filtered, and the filtrate was concentrated. A residue was purified by silica gel chromatography (heptane), and further purified by recrystallization from ethanol to obtain compound (S-14) (23.0 g).

Second Step

Under a nitrogen atmosphere, compound (S-14) (10 g) and THF (100 mL) were put in a reaction vessel, and the resulting mixture was cooled down to −74° C. Thereto, sec-butyl lithium (1 M; n-hexane, a cyclohexane solution; 33 mL) was added dropwise, and further the resulting mixture was stirred for 2 hours. Subsequently, sulfur powder (1.25 g) was added thereto, and stirred for 2 hours while returning the resulting mixture to 25° C. Then, bromoacetaldehyde diethyl acetal (8.89 g) was added thereto, and the resulting material was subjected to reflux for 2 hours. A reaction mixture was poured into water, and the resulting reaction mixture was subjected to extraction with toluene. An organic layer was washed with water, and dried over anhydrous magnesium sulfate. The resulting solution was concentrated under reduced pressure, and the residue was purified by silica gel chromatography (toluene) to obtain compound (S-15) (7.8 g).

Third Step

Under a nitrogen atmosphere, compound (S-15) (7.7 g), polyphosphoric acid (20 g) and toluene (150 mL) were put in a reaction vessel, and subjected to reflux under heating for 3 hours. A reaction mixture was poured into water, and the resulting reaction mixture was subjected to extraction with toluene. An organic layer was washed with water, and dried over anhydrous magnesium sulfate. The resulting solution was concentrated under reduced pressure, and a residue was purified by silica gel chromatography (toluene:heptane=2:3 in a volume ratio) to obtain compound (S-16) (3.9 g).

Fourth Step

Under a nitrogen atmosphere, compound (S-16) (3.9 g) and THF (100 mL) were put in a reaction vessel, and the resulting mixture was cooled down to −74° C. Thereto, lithium diisopropylamide (LDA, 1 M; an n-hexane solution; 16.82 mL) was added dropwise in a temperature range of −74° C. to −70° C., and further the resulting mixture was stirred for 2 hours. Subsequently, a THF (10 mL) solution of iodopropane (2.4 g) was added dropwise thereto in a temperature range of −75° C. to −70° C., and stirred for 8 hours while returning the resulting mixture to 25° C. A reaction mixture was poured into water, and the resulting reaction mixture was subjected to extraction with toluene, and washed with water, and then dried over anhydrous magnesium sulfate and concentrated under reduced pressure to obtain a light brown solid. The resulting material was subjected to silica gel column chromatography (heptane:toluene=4:1 in a volume ratio) and recrystallization (ethanol) to obtain compound (No. 105) as a colorless crystal (2.7 g).

¹H-NMR (δ ppm; CDCl₃): 7.31 (d, 1H), 7.01 (t, 1H), 6.90 (d, 1H), 3.88 (d, 2H), 2.83 (t, 2H), 1.95 (br, 2H), 1.79-1.69 (m, 9H), 1.30 (sex, 2H), 1.2-0.8 (m, 13H), 1.00 (t, 3H), 0.88 (t, 3H).

Physical properties of compound (No. 105) were as described below. Transition temperature: C 74.0 N 171.2 I. $T_{NI}$=145° C.; Δn=0.127; Δε=−2.0; η=51.4 mPa·s.

Example 7

Synthesis of Compound (No. 8)

In first step and second step in Example 1, compound (S-18) was prepared by using compound (S-17) in place of compound (S-1), and in Example 3, compound (No. 8) was obtained by using compound (S-10) in place of compound (S-9) and using compound (S-18) in place of compound (S-3).

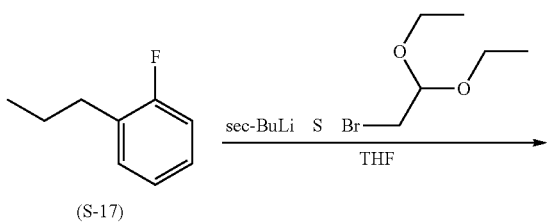

-continued

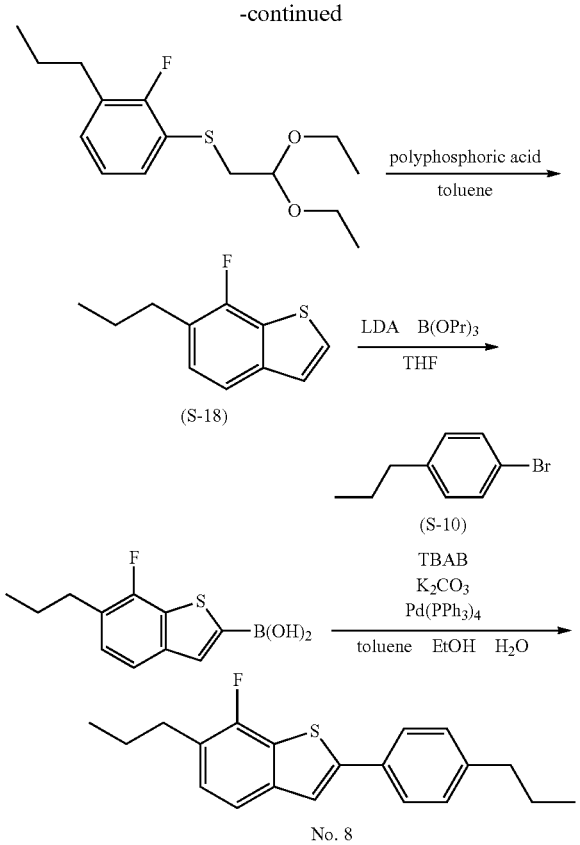

¹H-NMR (δ ppm; CDCl₃): 7.62 (d, 2H), 7.45 (s, 1H), 7.45 (d, 1H), 7.24 (d, 2H), 7.15 (t, 1H), 2.72 (t, 2H), 2.62 (t, 2H), 1.68 (sex, 2H), 1.67 (sex, 2H), 0.98 (t, 3H), 0.97 (t, 3H).

Physical properties of compound (No. 8) were as described below. Transition temperature: C 56.6 S 62.0 N 66.5 I. $T_{NI}$=65.0° C.; Δn=0.260; Δε=−0.7; η=40.8 mPa·s.

Example 8

Synthesis of Compound (No. 56)

In Example 3, compound (No. 56) was obtained by using compound (S-19) in place of compound (S-9).

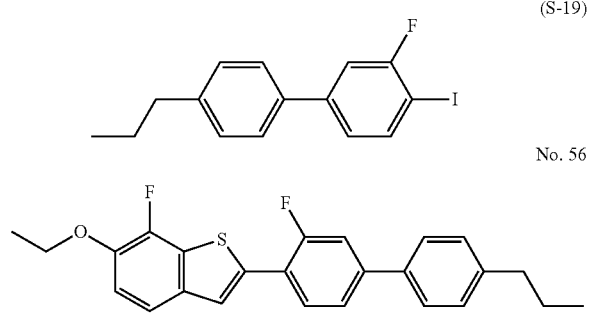

¹H-NMR (δ ppm; CDCl₃): 7.70 (t, 1H), 7.67 (dd, 1H), 7.54 (d, 2H), 7.48 (d, 1H), 7.43 (dd, 1H), 7.41 (dd, 1H), 7.27 (d, 2H), 7.09 (t, 1H), 4.21 (q, 2H), 2.64 (t, 2H), 1.69 (sex, 2H), 1.47 (t, 3H), 0.98 (t, 3H).

Physical properties of compound (No. 56) were as described below. Transition temperature: C 111.2 N 263.3 I. $T_{NI}$=201.7° C.; Δn=0.364; Δε=−3.80; η=66.4 mPa·s.

Example 9

Synthesis of Compound (No. 241)

In Example 3, compound (No. 241) was obtained by using compound (S-19) in place of compound (S-9).

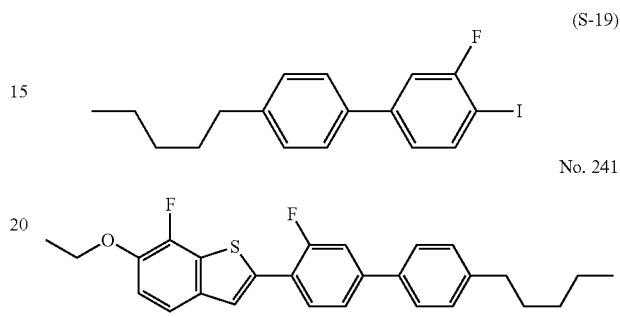

¹H-NMR (δ ppm; CDCl₃): 7.70 (t, 1H), 7.67 (dd, 1H), 7.53 (d, 2H), 7.48 (d, 1H), 7.43 (dd, 1H), 7.40 (dd, 1H), 7.27 (d, 2H), 7.09 (t, 1H), 4.21 (q, 2H), 2.65 (t, 2H), 1.66 (quint, 2H), 1.47 (t, 3H), 1.40-1.30 (m, 4H), 0.91 (t, 3H).

Physical properties of compound (No. 241) were as described below. Transition temperature: C 110.3 N 249.9 I. $T_{NI}$=192.7° C.; Δn=0.357; Δε=−3.70; η=61.7 mPa·s.

Example 10

Synthesis of Compound (No. 242)

In Example 3, compound (No. 242) was obtained by using compound (S-20) in place of compound (S-9).

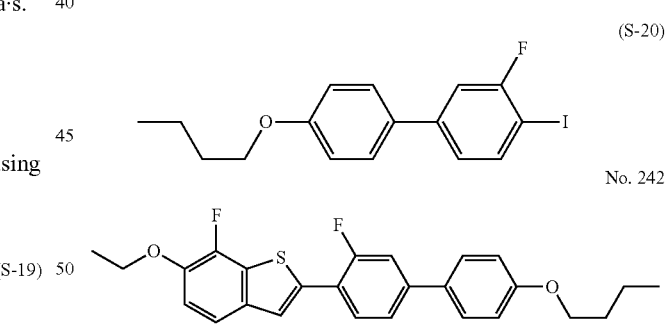

¹H-NMR (δ ppm; CDCl₃): 7.69 (t, 1H), 7.66 (dd, 1H), 7.54 (d, 2H), 7.47 (d, 1H), 7.40 (dd, 1H), 7.37 (dd, 1H), 7.09 (t, 1H), 6.98 (d, 2H), 4.21 (q, 2H), 4.01 (t, 2H), 2.64 (t, 2H), 1.80 (quint, 2H), 1.51 (sex, 2H), 1.48 (t, 3H), 0.99 (t, 3H).

Physical properties of compound (No. 242) were as described below. Transition temperature: C 128.5 N 281.3 I. $T_{NI}$=209.7° C.; Δn=0.377; Δε=−3.86; η=76.7 mPa·s.

Example 11

Synthesis of Compound (No. 244)

In Example 3, compound (No. 244) was obtained by using compound (S-21) in place of compound (S-9).

(S-21)

[Structure: 3-fluoro-4-iodo-propylbenzene]

No. 244

[Structure: ethoxy-fluoro-benzothiophene-fluorophenyl-propyl]

¹H-NMR (δ ppm; CDCl₃): 7.69 (t, 1H), 7.66 (dd, 1H), 7.47 (d, 1H), 7.40 (dd, 1H), 7.37 (dd, 1H), 7.09 (t, 1H), 4.21 (q, 2H), 4.01 (t, 2H), 2.64 (t, 2H), 1.69 (sex, 2H), 1.47 (t, 3H), 0.98 (t, 3H).

Physical properties of compound (No. 244) were as described below. Transition temperature: C 56.6 N 68.6 I. $T_{NI}$=88.4° C.; Δn=0.250; Δε=−3.89; η=37.4 mPa·s.

Example 12

Synthesis of Compound (No. 14)

In Example 3, compound (No. 14) was obtained by using compound (S-22) in place of compound (S-9).

(S-22)

[Structure: ethoxy-difluoro-bromobenzene]

No. 14

[Structure: ethoxy-fluoro-benzothiophene-difluorophenyl-ethoxy]

¹H-NMR (δ ppm; CDCl₃): 7.54 (dd, 1H), 7.46 (d, 1H), 7.29 (td, 1H), 7.08 (t, 1H), 6.78 (td, 1H), 4.21 (q, 2H), 4.16 (q, 2H), 1.47 (t, 3H), 1.46 (t, 3H).

Physical properties of compound (No. 14) were as described below. Transition temperature: C 140.4 I. $T_{NI}$=154.3° C.; Δn=0.387; Δε=−10.46; n=69.6 mPa·s.

Example 13

Synthesis of Compound (No. 243)

In Example 3, compound (No. 243) was obtained by using compound (S-23) in place of compound (S-9). In addition, compound (S-23) can be prepared according to a method described in Examples in JP 2010-270074 A, or the like.

(S-23)

[Structure: propylcyclohexyl-methoxy-difluoro-bromobenzene]

No. 243

[Structure: ethoxy-fluoro-benzothiophene-difluorophenyl-methoxy-cyclohexyl-ethyl]

¹H-NMR (δ ppm; CDCl₃): 7.54 (dd, 1H), 7.46 (d, 1H), 7.29 (td, 1H), 7.08 (t, 1H), 6.77 (td, 1H), 4.21 (q, 2H), 3.87 (d, 2H), 1.92 (d, 2H), 1.85-1.75 (m, 3H), 1.47 (t, 3H), 1.35-0.91 (m, 10H), 0.88 (t, 3H).

Physical properties of compound (No. 243) were as described below. Transition temperature: C 118.4 N 209.5 I. $T_{NI}$=190.3° C.; Δn=0.267; Δε=−3.69; η=79.4 mPa·s.

Example 14

Synthesis of Compound (No. 247)

In Example 3, compound (No. 247) was obtained by using compound (S-24) in place of compound (S-9). In addition, compound (S-24) is commercially available.

In Example 3, compound (No. 247) was obtained by using compound (S-24) in place of compound (S-9). In addition, (S-24) is commercially available.

(S-24)

[Structure: difluoro-bromophenyl-CF₂-O-trifluorophenyl]

No. 247

[Structure: ethoxy-fluoro-benzothiophene-difluorophenyl-CF₂-O-trifluorophenyl]

¹H-NMR (δ ppm; CDCl₃): 7.56 (d, 1H), 7.51 (d, 1H), 7.28 (d, 2H), 7.13 (t, 1H), 6.98 (t, 2H), 4.23 (q, 2H), 1.40 (t, 3H).

Physical properties of compound (No. 247) were as described below. Transition temperature: C 153.6 I. $T_{NI}$=111.7° C.; Δn=0.337; Δε=−0.98; η=77.5 mPa·s.

Example 15

Synthesis of Compound (No. 249)

In Example 3, compound (No. 249) was obtained by using compound (S-25) in place of compound (S-9).

(S-25)

[Structure: butyl-phenyl-fluorophenyl-iodide]

-continued
No. 249
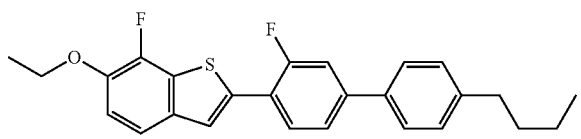
$^1$H-NMR (δ ppm; CDCl$_3$): 7.69 (t, 1H), 7.67 (dd, 1H), 7.52 (d, 2H), 7.47 (d, 1H), 7.42 (dd, 1H), 7.40 (dd, 1H), 7.27 (d, 2H), 7.08 (t, 1H), 4.21 (q, 2H), 2.66 (t, 2H), 1.65 (quint, 2H), 1.48 (t, 3H), 1.37 (sex, 2H), 0.95 (t, 3H).
Physical properties of compound (No. 249) were as described below. Transition temperature: C 102.24 N 249.2 I. $T_{NI}$=194.4° C.; Δn=0.350; Δε=−2.6; η=62.2 mPa·s.
Compounds (No. 1) to (No. 240) shown below can be prepared in a manner similar to the synthesis methods described in Examples 1 to 7.
| No. | |
|---|---|
| 1 | 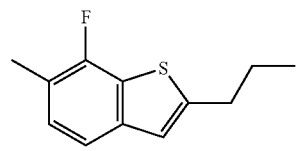 |
| 2 |  |
| 3 |  |
| 4 |  |
| 5 |  |
| 6 |  |
| 7 | 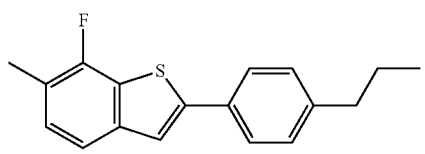 [SMILES: CCCc1ccc(-c2cc3ccc(C)c(F)c3s2)cc1] |
| 8 | 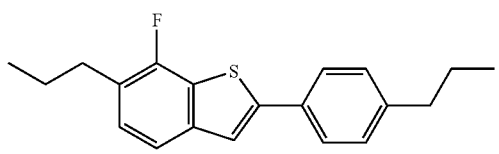 [SMILES: CCCc1ccc(-c2cc3ccc(CCC)c(F)c3s2)cc1] |

| No. | |
|---|---|
| 9 | 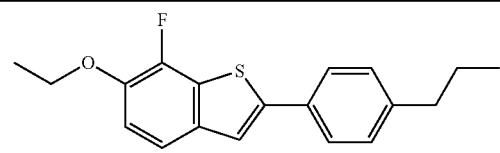 |
| 10 | 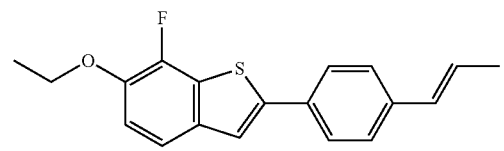 [SMILES: C/C=C/c1ccc(-c2cc3ccc(OCC)c(F)c3s2)cc1] |
| 11 | 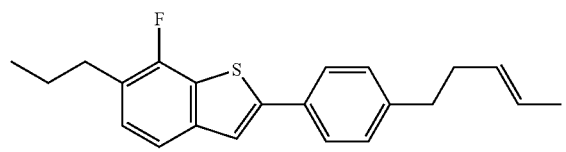 [SMILES: C/C=C/CCc1ccc(-c2cc3ccc(CCC)c(F)c3s2)cc1] |
| 12 | 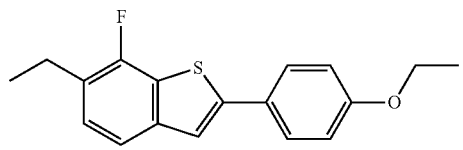 [SMILES: CCOc1ccc(-c2cc3ccc(CC)c(F)c3s2)cc1] |
| 13 | 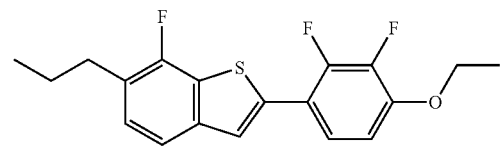 [SMILES: CCCc1ccc2cc(-c3ccc(OCC)c(F)c3F)sc2c1F] |
| 14 | 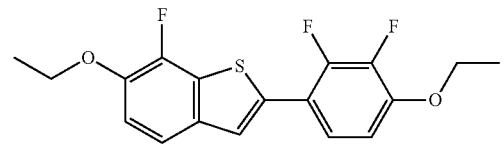 [SMILES: CCOc1ccc(-c2cc3ccc(OCC)c(F)c3s2)c(F)c1F] |
| 15 | 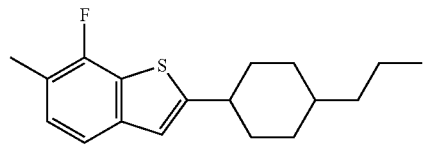 [SMILES: CCCC1CCC(c2cc3ccc(C)c(F)c3s2)CC1] |
| 16 | 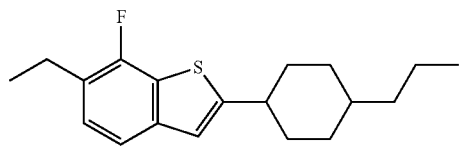 [SMILES: CCCC1CCC(c2cc3ccc(CC)c(F)c3s2)CC1] |
| 17 | 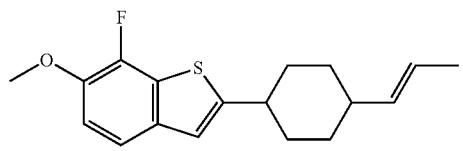 [SMILES: C/C=C/C1CCC(c2cc3ccc(OC)c(F)c3s2)CC1] |
| 18 | 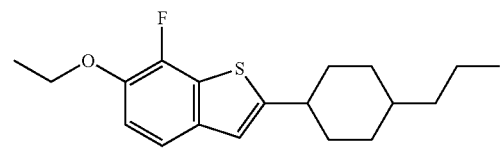 [SMILES: CCCC1CCC(c2cc3ccc(OCC)c(F)c3s2)CC1] |

|No.|  |
|---|---|
|19| 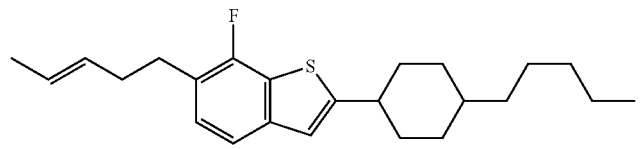 [SMILES: C/C=C/CCc1ccc2cc(C3CCC(CCCCC)CC3)sc2c1F] |
|20| 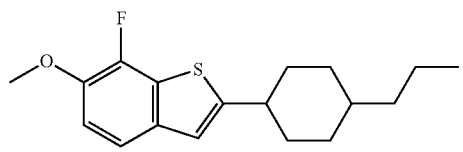 [SMILES: CCCC1CCC(c2cc3ccc(OC)c(F)c3s2)CC1] |
|21| 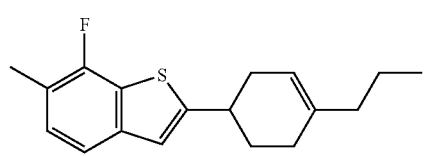 |
|22| 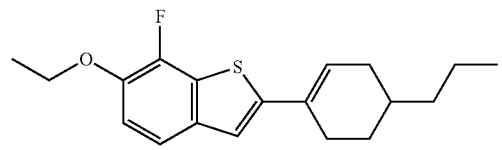 [SMILES: CCCC1CC=C(c2cc3ccc(OCC)c(F)c3s2)CC1] |
|23| 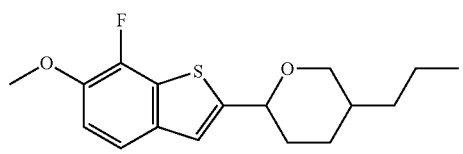 [SMILES: CCCC1CCC(c2cc3ccc(OC)c(F)c3s2)OC1] |
|24| 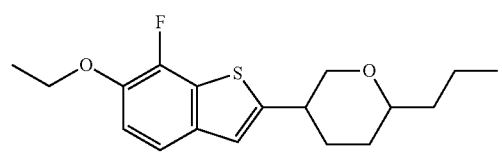 |
|25| 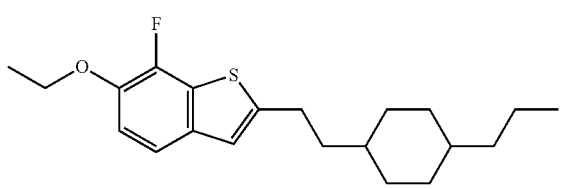 [SMILES: CCCC1CCC(CCc2cc3ccc(OCC)c(F)c3s2)CC1] |
|26| 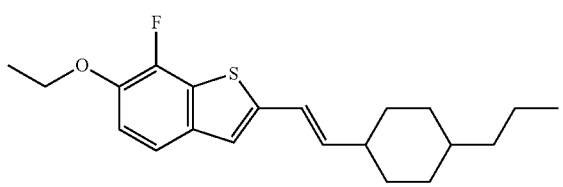 [SMILES: CCCC1CCC(/C=C/c2cc3ccc(OCC)c(F)c3s2)CC1] |
|27| 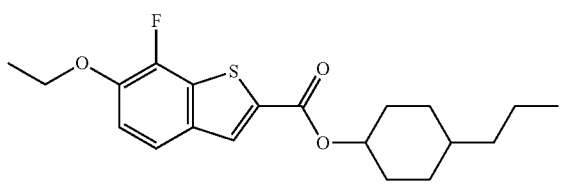 [SMILES: CCCC1CCC(OC(=O)c2cc3ccc(OCC)c(F)c3s2)CC1] |

| No. | |
|---|---|
| 28 | 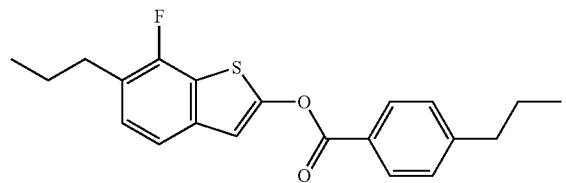 [SMILES: CCCc1ccc(C(=O)Oc2cc3ccc(CCC)c(F)c3s2)cc1] |
| 29 | 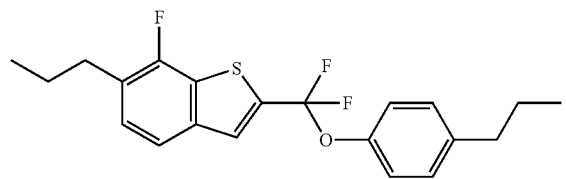 [SMILES: CCCc1ccc(OC(F)(F)c2cc3ccc(CCC)c(F)c3s2)cc1] |
| 30 | 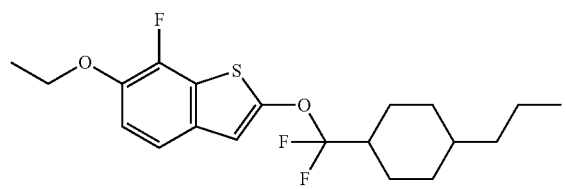 [SMILES: CCCC1CCC(C(F)(F)Oc2cc3ccc(OCC)c(F)c3s2)CC1] |
| 31 | 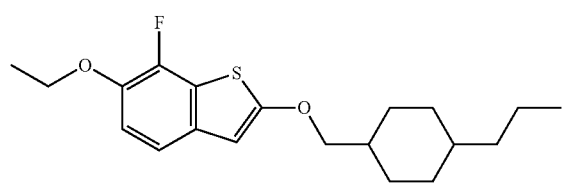 [SMILES: CCCC1CCC(COc2cc3ccc(OCC)c(F)c3s2)CC1] |
| 32 | 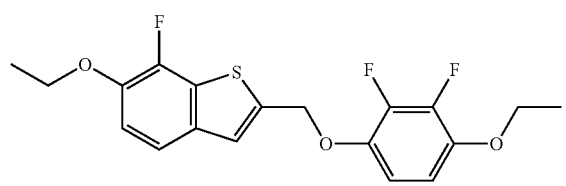 [SMILES: CCOc1ccc(OCc2cc3ccc(OCC)c(F)c3s2)c(F)c1F] |
| 33 | 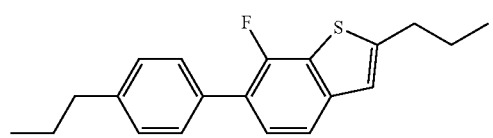 [SMILES: CCCc1ccc(-c2ccc3cc(CCC)sc3c2F)cc1] |
| 34 | 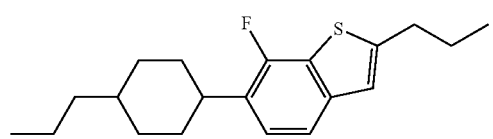 [SMILES: CCCc1cc2ccc(C3CCC(CCC)CC3)c(F)c2s1] |
| 35 | 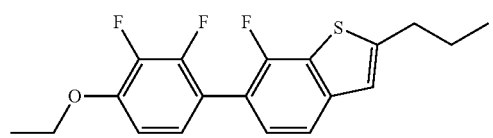 [SMILES: CCCc1cc2ccc(-c3ccc(OCC)c(F)c3F)c(F)c2s1] |
| 36 | 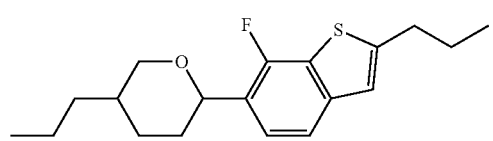 [SMILES: CCCc1cc2ccc(C3CCC(CCC)CO3)c(F)c2s1] |

| No. | |
|---|---|
| 37 | 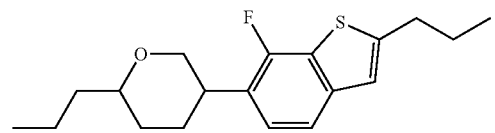 [SMILES: CCCc1cc2ccc(C3CCC(CCC)OC3)c(F)c2s1] |
| 38 | 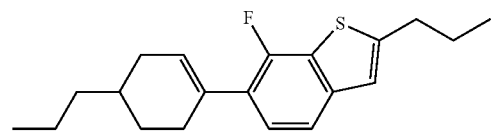 |
| 39 | 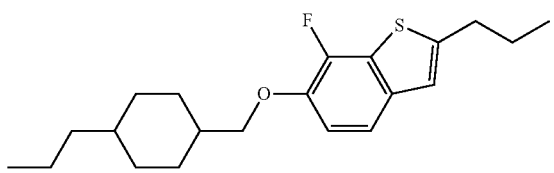 [SMILES: CCCc1cc2ccc(OCC3CCC(CCC)CC3)c(F)c2s1] |
| 40 | 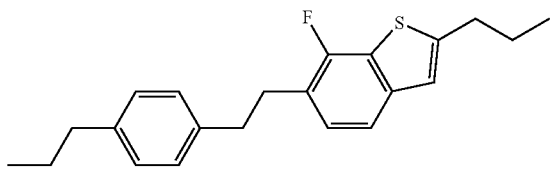 [SMILES: CCCc1ccc(CCc2ccc3cc(CCC)sc3c2F)cc1] |
| 41 | 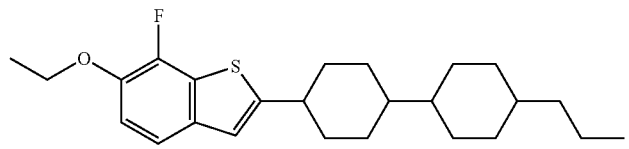 [SMILES: CCCC1CCC(C2CCC(c3cc4ccc(OCC)c(F)c4s3)CC2)CC1] |
| 42 | 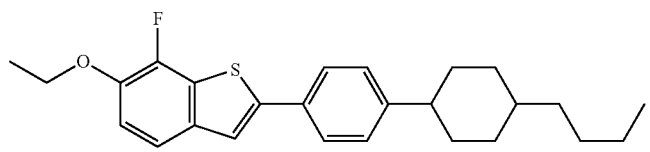 [SMILES: CCCCC1CCC(c2ccc(-c3cc4ccc(OCC)c(F)c4s3)cc2)CC1] |
| 43 | 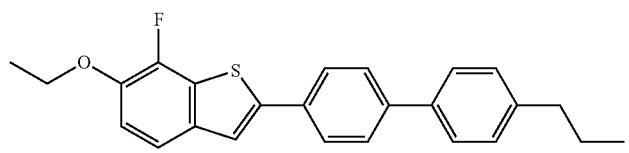 [SMILES: CCCc1ccc(-c2ccc(-c3cc4ccc(OCC)c(F)c4s3)cc2)cc1] |
| 44 | 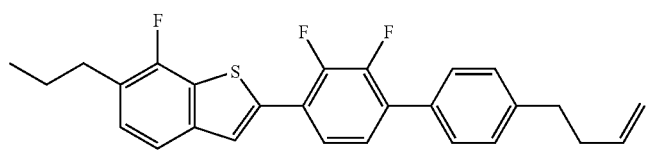 [SMILES: C=CCCc1ccc(-c2ccc(-c3cc4ccc(CCC)c(F)c4s3)c(F)c2F)cc1] |
| 45 | 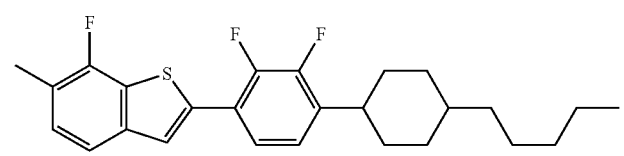 |
| 46 | 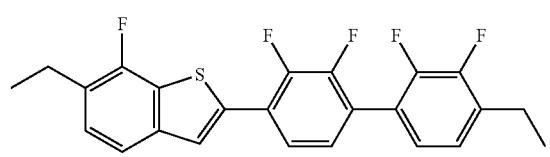 |

| No. | |
|---|---|
| 47 | 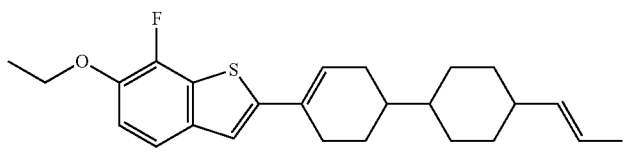 [SMILES: C/C=C/C1CCC(C2CC=C(c3cc4ccc(OCC)c(F)c4s3)CC2)CC1] |
| 48 | 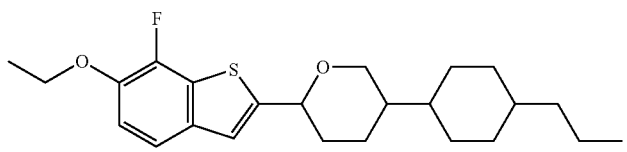 [SMILES: CCCC1CCC(C2CCC(c3cc4ccc(OCC)c(F)c4s3)OC2)CC1] |
| 49 | 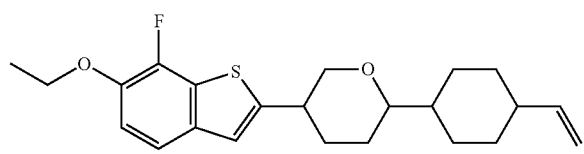 [SMILES: C=CC1CCC(C2CCC(c3cc4ccc(OCC)c(F)c4s3)CO2)CC1] |
| 50 | 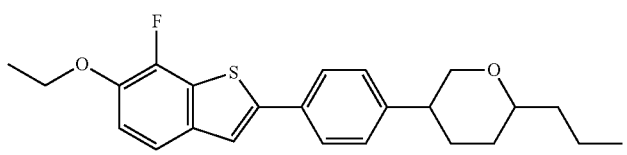 [SMILES: CCCC1CCC(c2ccc(-c3cc4ccc(OCC)c(F)c4s3)cc2)CO1] |
| 51 | 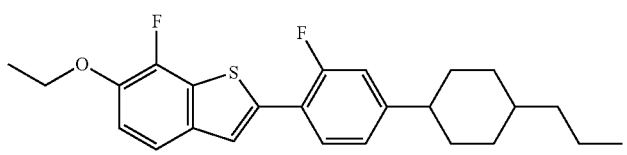 [SMILES: CCCC1CCC(c2ccc(-c3cc4ccc(OCC)c(F)c4s3)c(F)c2)CC1] |
| 52 | 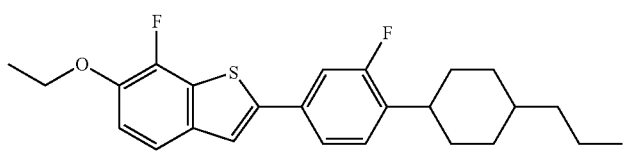 [SMILES: CCCC1CCC(c2ccc(-c3cc4ccc(OCC)c(F)c4s3)cc2F)CC1] |
| 53 | 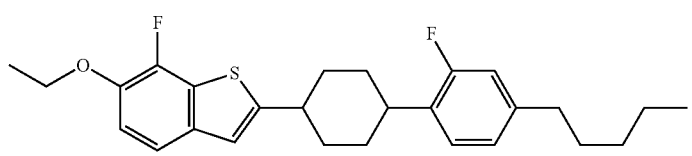 [SMILES: CCCCCc1ccc(C2CCC(c3cc4ccc(OCC)c(F)c4s3)CC2)c(F)c1] |
| 54 | 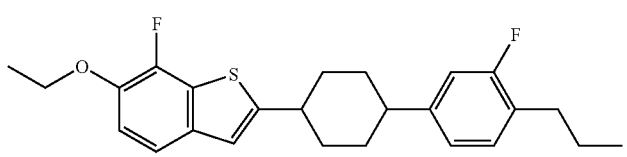 [SMILES: CCCc1ccc(C2CCC(c3cc4ccc(OCC)c(F)c4s3)CC2)cc1F] |
| 55 | 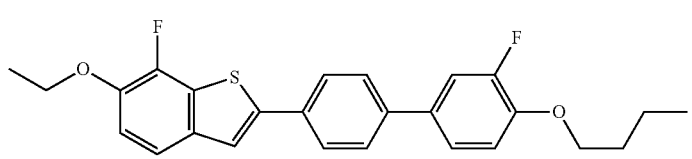 [SMILES: CCCCOc1ccc(-c2ccc(-c3cc4ccc(OCC)c(F)c4s3)cc2)cc1F] |
| 56 | 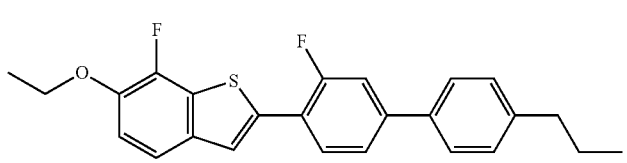 [SMILES: CCCc1ccc(-c2ccc(-c3cc4ccc(OCC)c(F)c4s3)c(F)c2)cc1] |

| No. | |
|---|---|
| 57 | 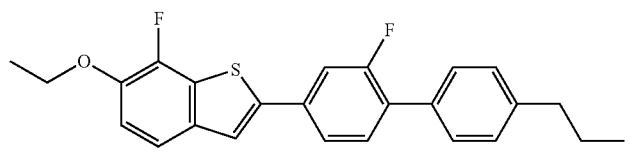 [SMILES: CCCc1ccc(-c2ccc(-c3cc4ccc(OCC)c(F)c4s3)cc2F)cc1] |
| 58 | 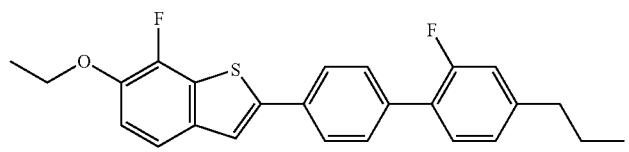 [SMILES: CCCc1ccc(-c2ccc(-c3cc4ccc(OCC)c(F)c4s3)cc2)c(F)c1] |
| 59 | 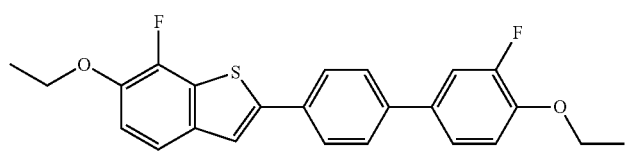 [SMILES: CCOc1ccc(-c2ccc(-c3cc4ccc(OCC)c(F)c4s3)cc2)cc1F] |
| 60 | 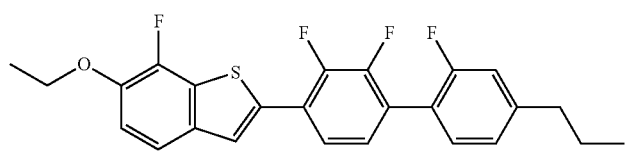 [SMILES: CCCc1ccc(-c2ccc(-c3cc4ccc(OCC)c(F)c4s3)c(F)c2F)c(F)c1] |
| 61 | 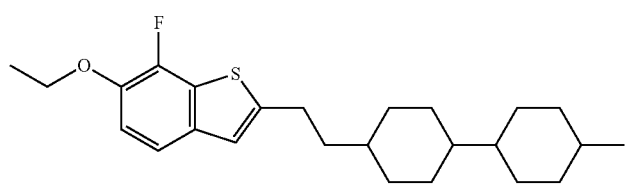 [SMILES: CCOc1ccc2cc(CCC3CCC(C4CCC(C)CC4)CC3)sc2c1F] |
| 62 | 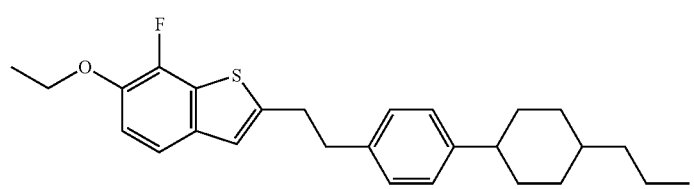 [SMILES: CCCC1CCC(c2ccc(CCc3cc4ccc(OCC)c(F)c4s3)cc2)CC1] |
| 63 | 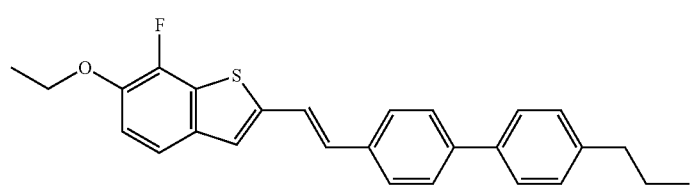 [SMILES: CCCc1ccc(-c2ccc(/C=C/c3cc4ccc(OCC)c(F)c4s3)cc2)cc1] |
| 64 | 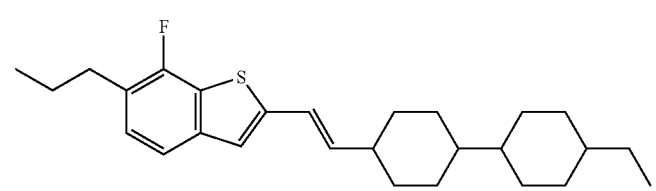 [SMILES: CCCc1ccc2cc(/C=C/C3CCC(C4CCC(CC)CC4)CC3)sc2c1F] |
| 65 | 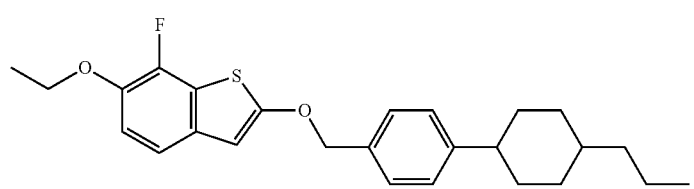 [SMILES: CCCC1CCC(c2ccc(COc3cc4ccc(OCC)c(F)c4s3)cc2)CC1] |

| No. | |
|---|---|
| 66 | 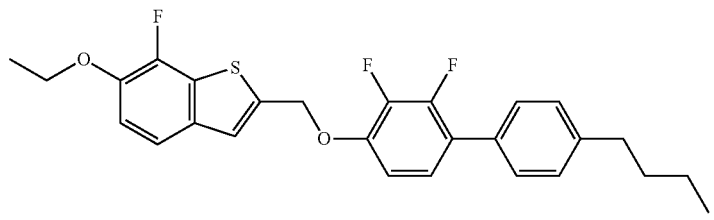 [SMILES: CCCCc1ccc(-c2ccc(OCc3cc4ccc(OCC)c(F)c4s3)c(F)c2F)cc1] |
| 67 | 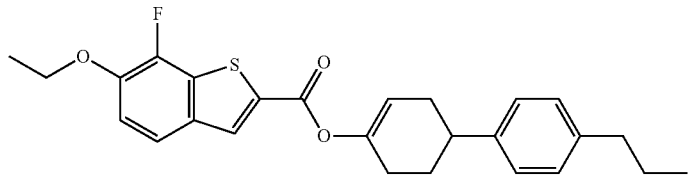 [SMILES: CCCc1ccc(C2CC=C(OC(=O)c3cc4ccc(OCC)c(F)c4s3)CC2)cc1] |
| 68 | 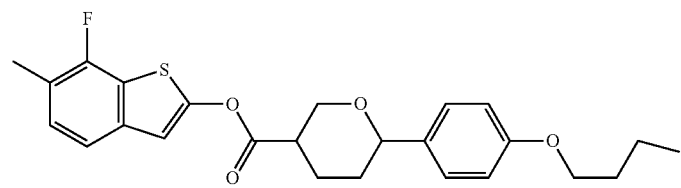 [SMILES: CCCCOc1ccc(C2CCC(C(=O)Oc3cc4ccc(C)c(F)c4s3)CO2)cc1] |
| 69 | 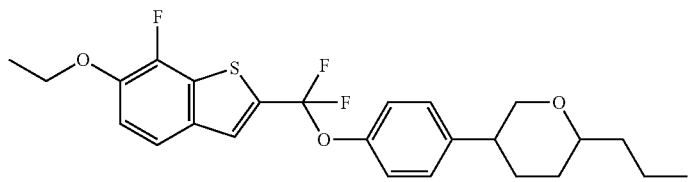 [SMILES: CCCC1CCC(c2ccc(OC(F)(F)c3cc4ccc(OCC)c(F)c4s3)cc2)CO1] |
| 70 | 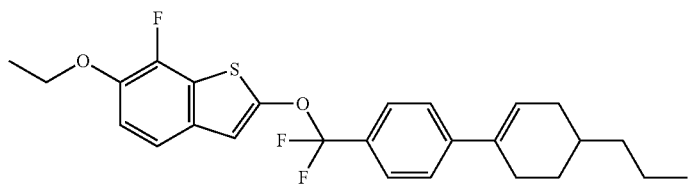 [SMILES: CCCC1CC=C(c2ccc(C(F)(F)Oc3cc4ccc(OCC)c(F)c4s3)cc2)CC1] |
| 71 | 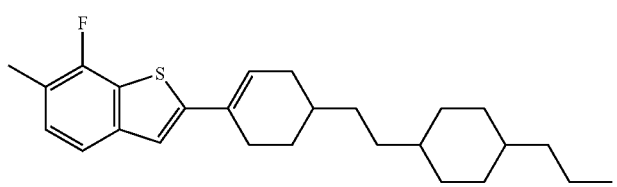 [SMILES: CCCC1CCC(CCC2CC=C(c3cc4ccc(C)c(F)c4s3)CC2)CC1] |
| 72 | 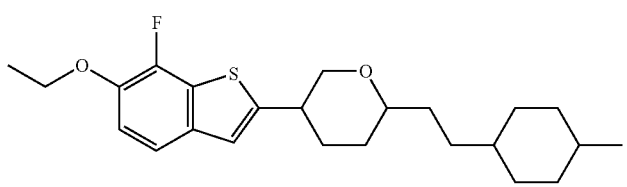 [SMILES: CCOc1ccc2cc(C3CCC(CCC4CCC(C)CC4)OC3)sc2c1F] |
| 73 | 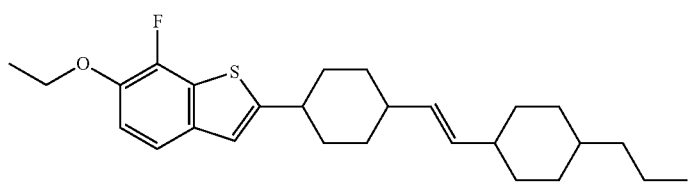 [SMILES: CCCC1CCC(/C=C/C2CCC(c3cc4ccc(OCC)c(F)c4s3)CC2)CC1] |

| No. | |
|---|---|
| 74 | 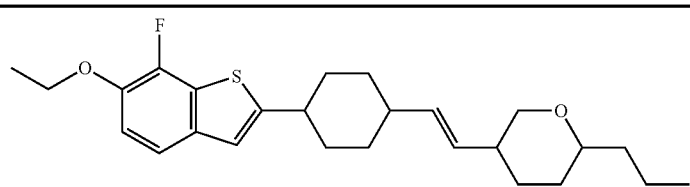 |
| 75 | 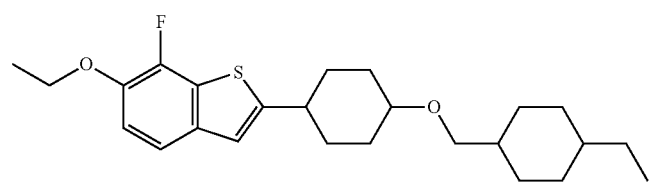 [SMILES: CCOc1ccc2cc(C3CCC(OCC4CCC(CC)CC4)CC3)sc2c1F] |
| 76 | 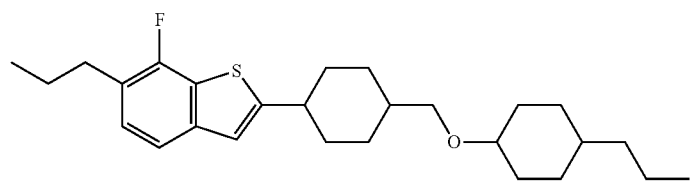 [SMILES: CCCc1ccc2cc(C3CCC(COC4CCC(CCC)CC4)CC3)sc2c1F] |
| 77 | 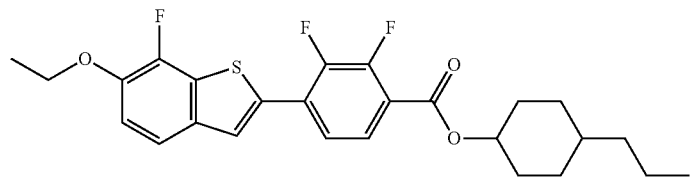 [SMILES: CCCC1CCC(OC(=O)c2ccc(-c3cc4ccc(OCC)c(F)c4s3)c(F)c2F)CC1] |
| 78 | 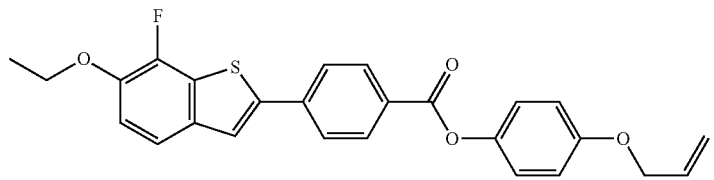 [SMILES: C=CCOc1ccc(OC(=O)c2ccc(-c3cc4ccc(OCC)c(F)c4s3)cc2)cc1] |
| 79 | 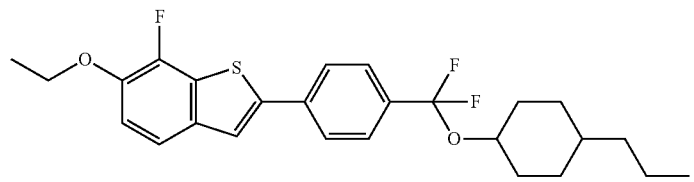 [SMILES: CCCC1CCC(OC(F)(F)c2ccc(-c3cc4ccc(OCC)c(F)c4s3)cc2)CC1] |
| 80 | 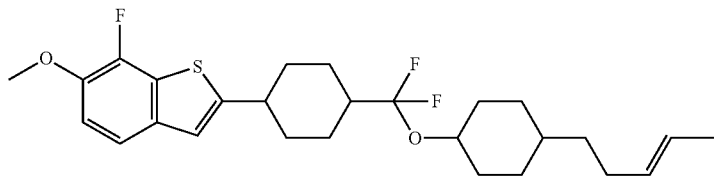 [SMILES: C/C=C/CCC1CCC(OC(F)(F)C2CCC(c3cc4ccc(OC)c(F)c4s3)CC2)CC1] |
| 81 | 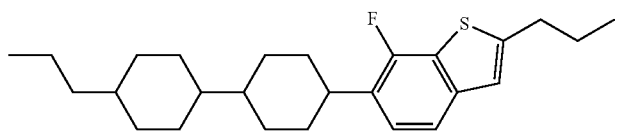 [SMILES: CCCc1cc2ccc(C3CCC(C4CCC(CCC)CC4)CC3)c(F)c2s1] |
| 82 | 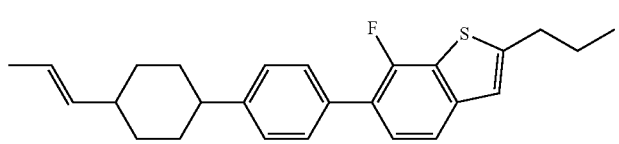 [SMILES: C/C=C/C1CCC(c2ccc(-c3ccc4cc(CCC)sc4c3F)cc2)CC1] |

| No. | |
|---|---|
| 83 | 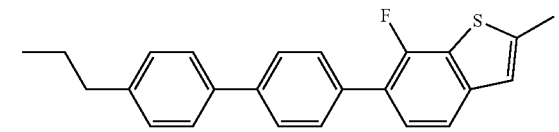 [SMILES: CCCc1ccc(-c2ccc(-c3ccc4cc(C)sc4c3F)cc2)cc1] |
| 84 | 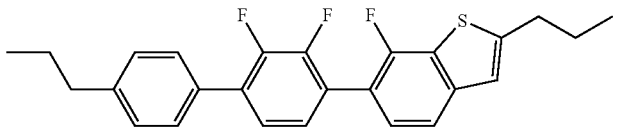 [SMILES: CCCc1ccc(-c2ccc(-c3ccc4cc(CCC)sc4c3F)c(F)c2F)cc1] |
| 85 | 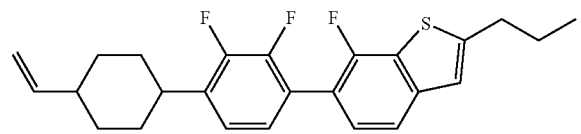 [SMILES: C=CC1CCC(c2ccc(-c3ccc4cc(CCC)sc4c3F)c(F)c2F)CC1] |
| 86 | 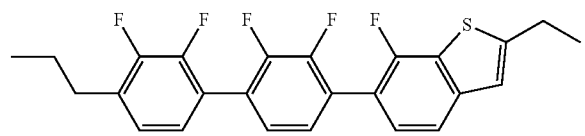 [SMILES: CCCc1ccc(-c2ccc(-c3ccc4cc(CC)sc4c3F)c(F)c2F)c(F)c1F] |
| 87 | 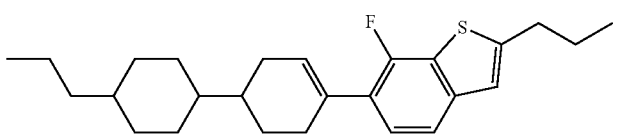 |
| 88 | 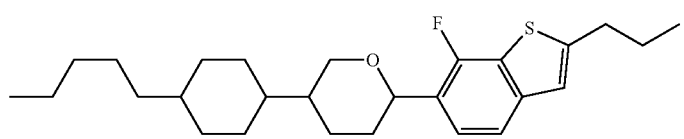 [SMILES: CCCCCC1CCC(C2CCC(c3ccc4cc(CCC)sc4c3F)OC2)CC1] |
| 89 | 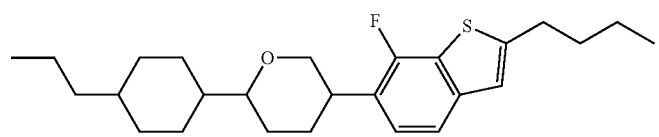 [SMILES: CCCCc1cc2ccc(C3CCC(C4CCC(CCC)CC4)OC3)c(F)c2s1] |
| 90 | 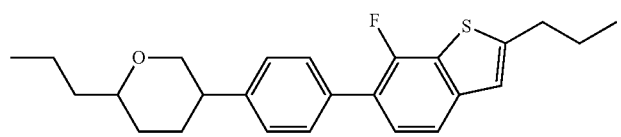 [SMILES: CCCc1cc2ccc(-c3ccc(C4CCC(CCC)OC4)cc3)c(F)c2s1] |
| 91 | 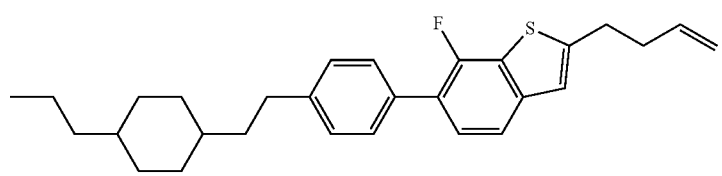 [SMILES: C=CCCc1cc2ccc(-c3ccc(CCC4CCC(CCC)CC4)cc3)c(F)c2s1] |
| 92 | 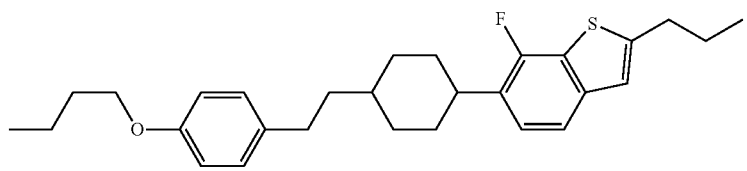 [SMILES: CCCCOc1ccc(CCC2CCC(c3ccc4cc(CCC)sc4c3F)CC2)cc1] |

-continued
| No. | |
|---|---|
| 93 | 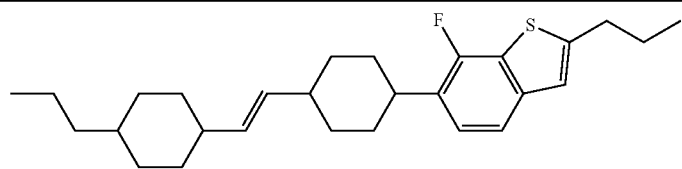 |
| 94 | 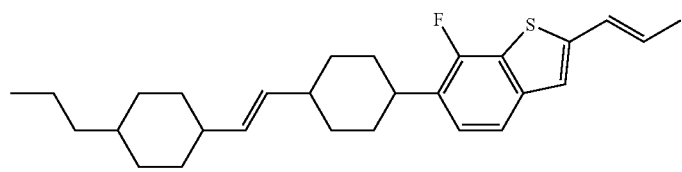 [SMILES: C/C=C/c1cc2ccc(C3CCC(/C=C/C4CCC(CCC)CC4)CC3)c(F)c2s1] |
| 95 | 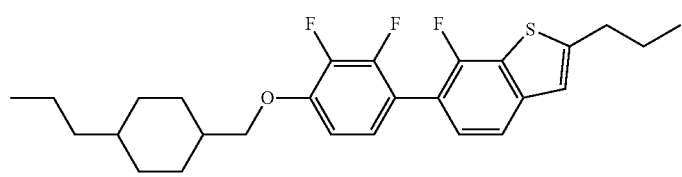 [SMILES: CCCc1cc2ccc(-c3ccc(OCC4CCC(CCC)CC4)c(F)c3F)c(F)c2s1] |
| 96 | 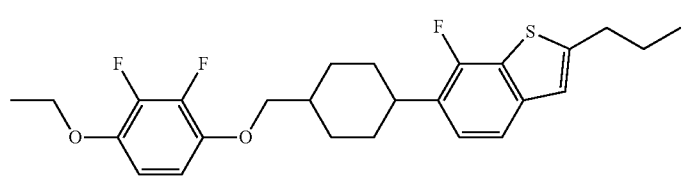 [SMILES: CCCc1cc2ccc(C3CCC(COc4ccc(OCC)c(F)c4F)CC3)c(F)c2s1] |
| 97 | 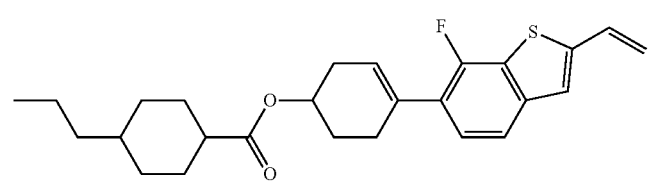 [SMILES: C=Cc1cc2ccc(C3=CCC(OC(=O)C4CCC(CCC)CC4)CC3)c(F)c2s1] |
| 98 | 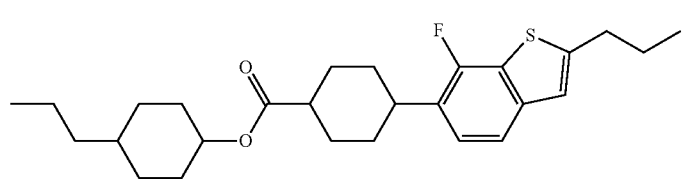 [SMILES: CCCc1cc2ccc(C3CCC(C(=O)OC4CCC(CCC)CC4)CC3)c(F)c2s1] |
| 99 | 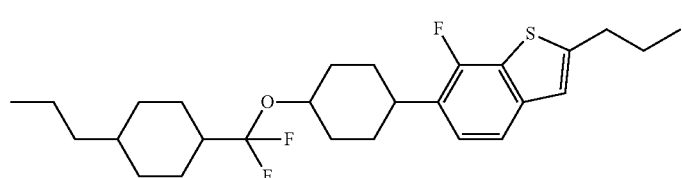 |
| 100 | 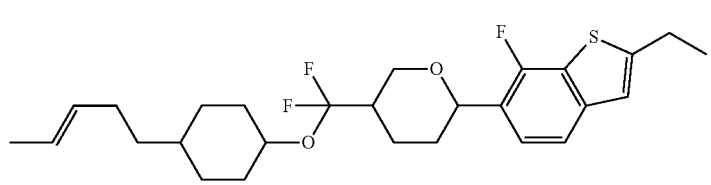 [SMILES: C/C=C/CCC1CCC(OC(F)(F)C2CCC(c3ccc4cc(CC)sc4c3F)OC2)CC1] |
| 101 | 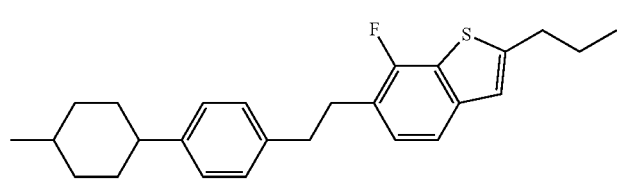 [SMILES: CCCc1cc2ccc(CCc3ccc(C4CCC(C)CC4)cc3)c(F)c2s1] |

| No. |
|---|
| 102 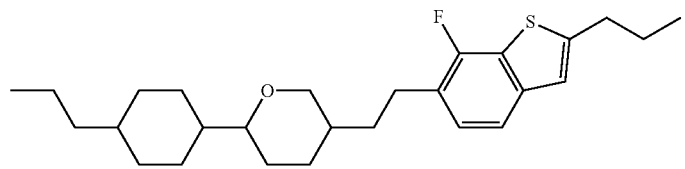 [SMILES: CCCc1cc2ccc(CCC3CCC(C4CCC(CCC)CC4)OC3)c(F)c2s1] |
| 103 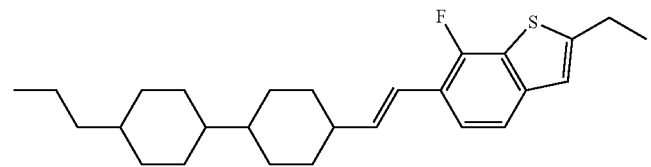 [SMILES: CCCC1CCC(C2CCC(/C=C/c3ccc4cc(CC)sc4c3F)CC2)CC1] |
| 104 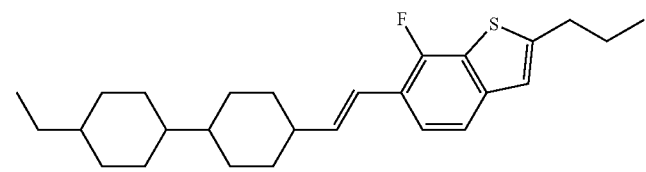 |
| 105 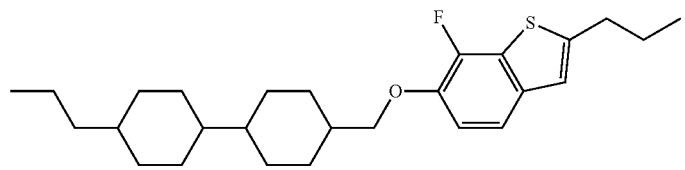 [SMILES: CCCc1cc2ccc(OCC3CCC(C4CCC(CCC)CC4)CC3)c(F)c2s1] |
| 106 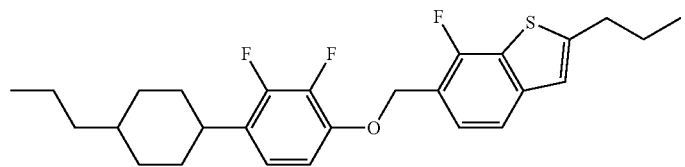 [SMILES: CCCc1cc2ccc(COc3ccc(C4CCC(CCC)CC4)c(F)c3F)c(F)c2s1] |
| 107 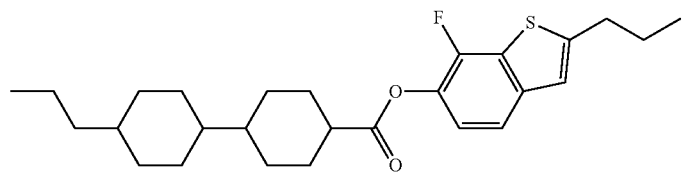 [SMILES: CCCc1cc2ccc(OC(=O)C3CCC(C4CCC(CCC)CC4)CC3)c(F)c2s1] |
| 108 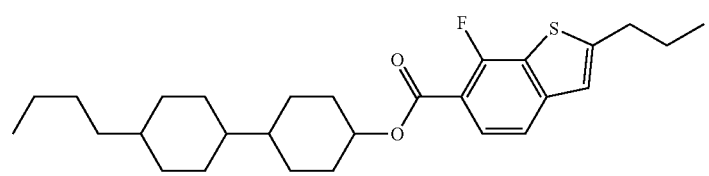 [SMILES: CCCCC1CCC(C2CCC(OC(=O)c3ccc4cc(CCC)sc4c3F)CC2)CC1] |
| 109 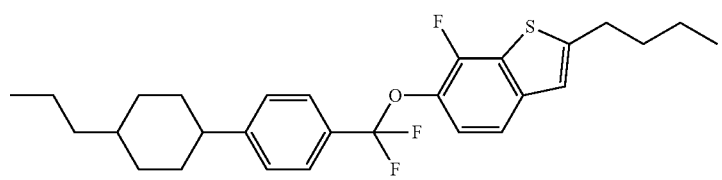 [SMILES: CCCCc1cc2ccc(OC(F)(F)c3ccc(C4CCC(CCC)CC4)cc3)c(F)c2s1] |

-continued
| No. | |
|---|---|
| 110 | 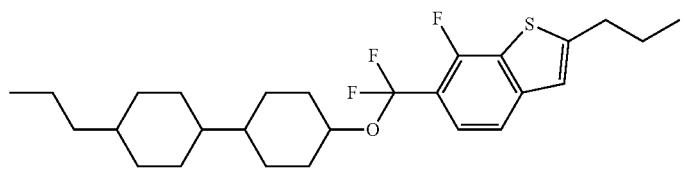 [SMILES: CCCc1cc2ccc(C(F)(F)OC3CCC(C4CCC(CCC)CC4)CC3)c(F)c2s1] |
| 111 | 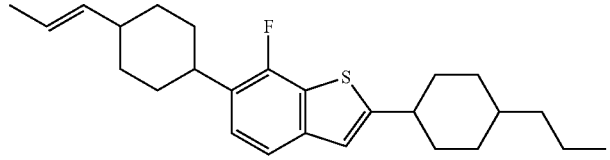 [SMILES: C/C=C/C1CCC(c2ccc3cc(C4CCC(CCC)CC4)sc3c2F)CC1] |
| 112 | 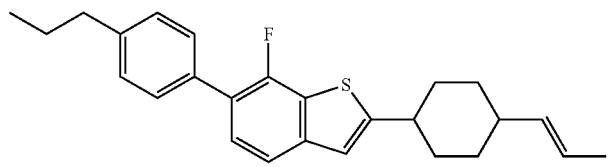 [SMILES: C/C=C/C1CCC(c2cc3ccc(-c4ccc(CCC)cc4)c(F)c3s2)CC1] |
| 113 | 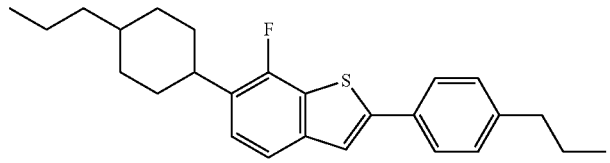 [SMILES: CCCc1ccc(-c2cc3ccc(C4CCC(CCC)CC4)c(F)c3s2)cc1] |
| 114 | 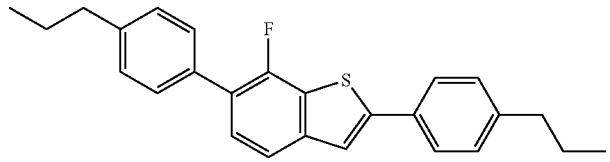 [SMILES: CCCc1ccc(-c2cc3ccc(-c4ccc(CCC)cc4)c(F)c3s2)cc1] |
| 115 | 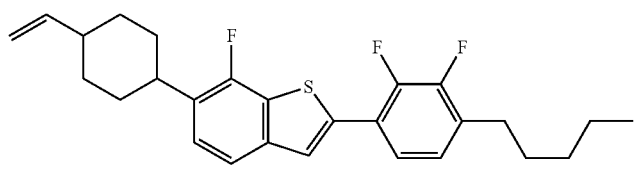 [SMILES: C=CC1CCC(c2ccc3cc(-c4ccc(CCCCC)c(F)c4F)sc3c2F)CC1] |
| 116 |  |
| 117 | 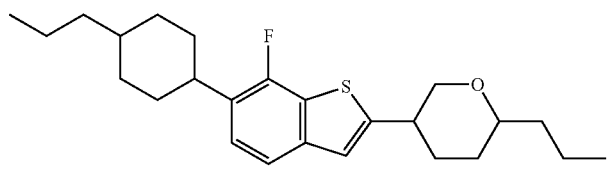 [SMILES: CCCC1CCC(c2ccc3cc(C4CCC(CCC)OC4)sc3c2F)CC1] |
| 118 | 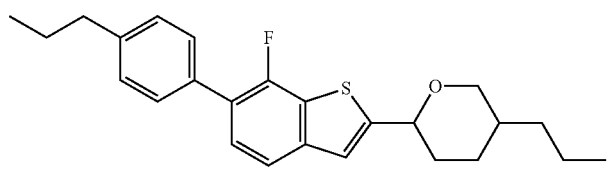 [SMILES: CCCc1ccc(-c2ccc3cc(C4CCC(CCC)CO4)sc3c2F)cc1] |

| No. | |
|---|---|
| 119 | 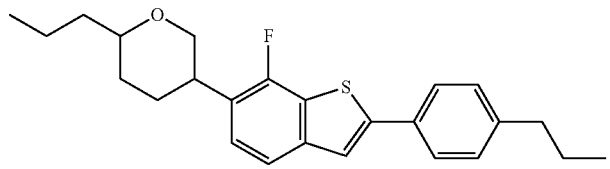 [SMILES: CCCc1ccc(-c2cc3ccc(C4CCC(CCC)OC4)c(F)c3s2)cc1] |
| 120 | 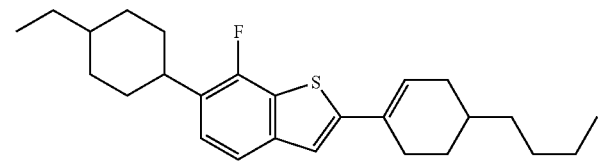 [SMILES: CCCCC1CC=C(c2cc3ccc(C4CCC(CC)CC4)c(F)c3s2)CC1] |
| 121 | 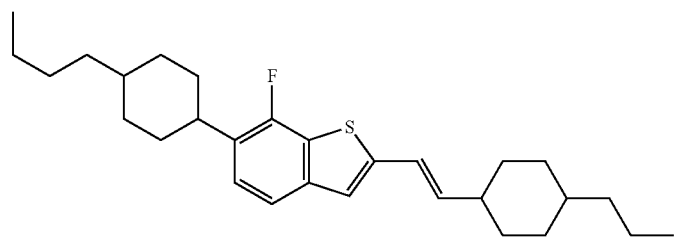 [SMILES: CCCCC1CCC(c2ccc3cc(/C=C/C4CCC(CCC)CC4)sc3c2F)CC1] |
| 122 | 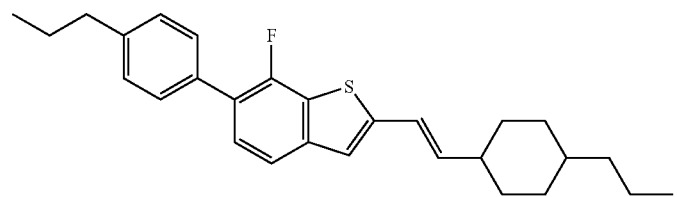 [SMILES: CCCc1ccc(-c2ccc3cc(/C=C/C4CCC(CCC)CC4)sc3c2F)cc1] |
| 123 | 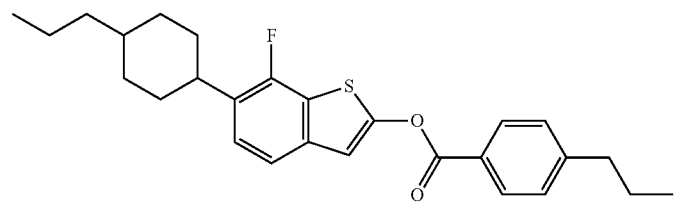 [SMILES: CCCc1ccc(C(=O)Oc2cc3ccc(C4CCC(CCC)CC4)c(F)c3s2)cc1] |
| 124 | 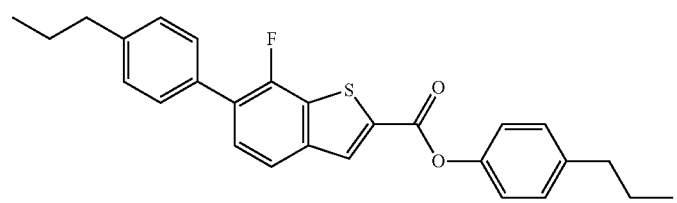 [SMILES: CCCc1ccc(OC(=O)c2cc3ccc(-c4ccc(CCC)cc4)c(F)c3s2)cc1] |
| 125 | 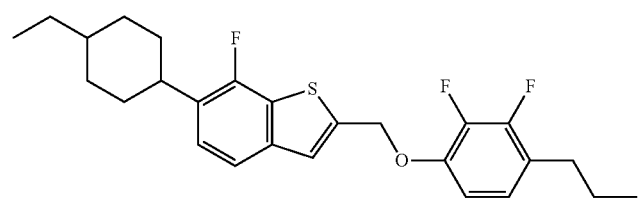 [SMILES: CCCc1ccc(OCc2cc3ccc(C4CCC(CC)CC4)c(F)c3s2)c(F)c1F] |

-continued
| No. | |
|---|---|
| 126 | 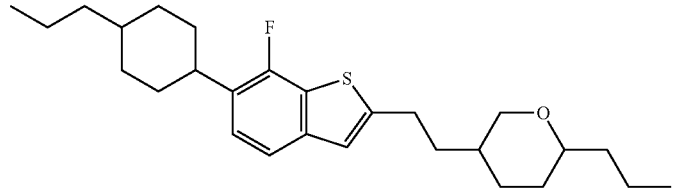 [SMILES: CCCC1CCC(c2ccc3cc(CCC4CCC(CCC)OC4)sc3c2F)CC1] |
| 127 | 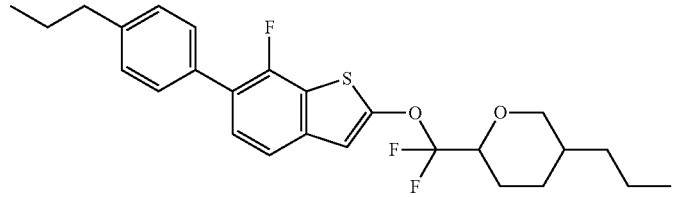 [SMILES: CCCc1ccc(-c2ccc3cc(OC(F)(F)C4CCC(CCC)CO4)sc3c2F)cc1] |
| 128 | 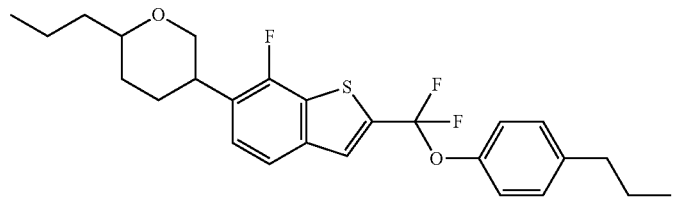 [SMILES: CCCc1ccc(OC(F)(F)c2cc3ccc(C4CCC(CCC)OC4)c(F)c3s2)cc1] |
| 129 | 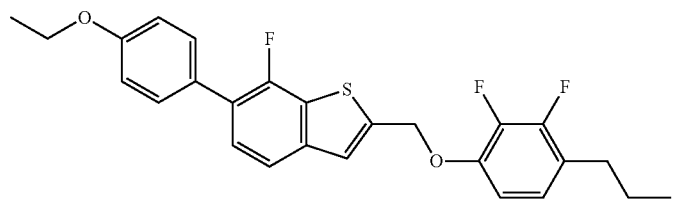 [SMILES: CCCc1ccc(OCc2cc3ccc(-c4ccc(OCC)cc4)c(F)c3s2)c(F)c1F] |
| 130 | 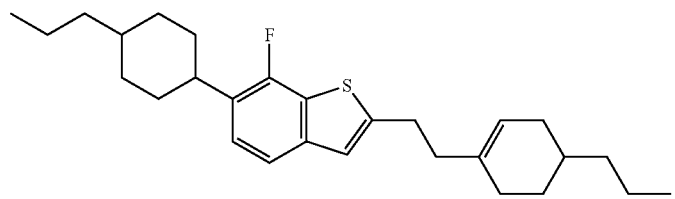 [SMILES: CCCC1CC=C(CCc2cc3ccc(C4CCC(CCC)CC4)c(F)c3s2)CC1] |
| 131 | 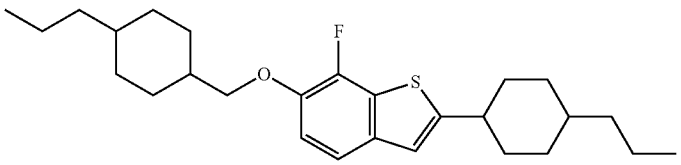 [SMILES: CCCC1CCC(COc2ccc3cc(C4CCC(CCC)CC4)sc3c2F)CC1] |
| 132 | 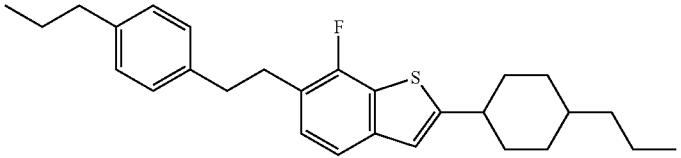 [SMILES: CCCc1ccc(CCc2ccc3cc(C4CCC(CCC)CC4)sc3c2F)cc1] |
| 133 | 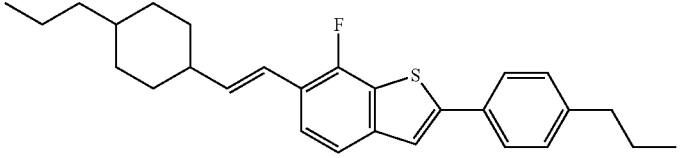 [SMILES: CCCc1ccc(-c2cc3ccc(/C=C/C4CCC(CCC)CC4)c(F)c3s2)cc1] |

| No. | |
|---|---|
| 134 | 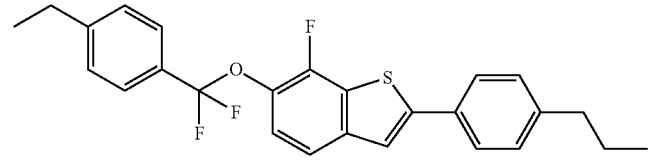 [SMILES: CCCc1ccc(-c2cc3ccc(OC(F)(F)c4ccc(CC)cc4)c(F)c3s2)cc1] |
| 135 | 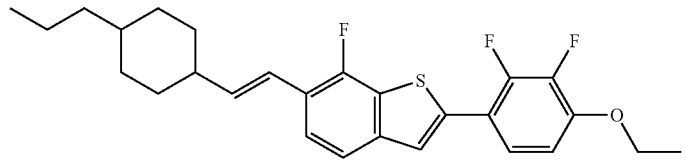 [SMILES: CCCC1CCC(/C=C/c2ccc3cc(-c4ccc(OCC)c(F)c4F)sc3c2F)CC1] |
| 136 | 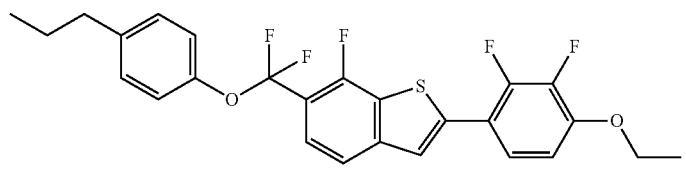 [SMILES: CCCc1ccc(OC(F)(F)c2ccc3cc(-c4ccc(OCC)c(F)c4F)sc3c2F)cc1] |
| 137 | 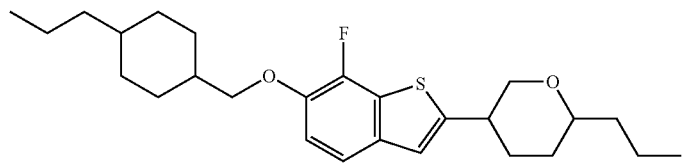 [SMILES: CCCC1CCC(COc2ccc3cc(C4CCC(CCC)OC4)sc3c2F)CC1] |
| 138 | 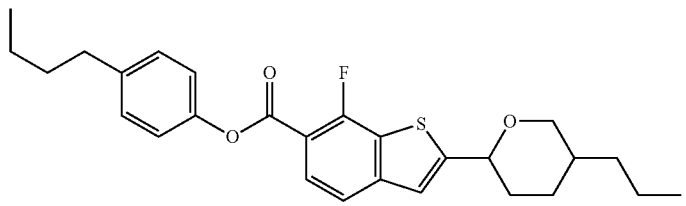 [SMILES: CCCCc1ccc(OC(=O)c2ccc3cc(C4CCC(CCC)CO4)sc3c2F)cc1] |
| 139 | 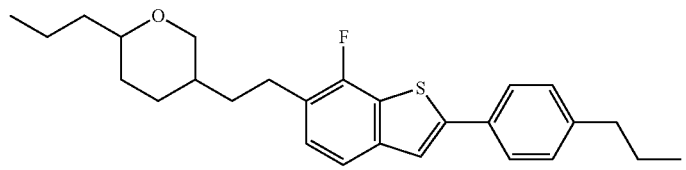 [SMILES: CCCc1ccc(-c2cc3ccc(CCC4CCC(CCC)OC4)c(F)c3s2)cc1] |
| 140 | 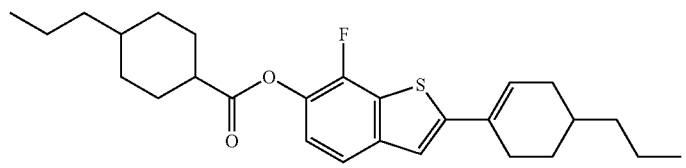 [SMILES: CCCC1CC=C(c2cc3ccc(OC(=O)C4CCC(CCC)CC4)c(F)c3s2)CC1] |
| 141 | 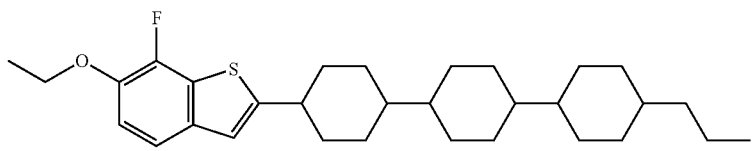 [SMILES: CCCC1CCC(C2CCC(C3CCC(c4cc5ccc(OCC)c(F)c5s4)CC3)CC2)CC1] |
| 142 | 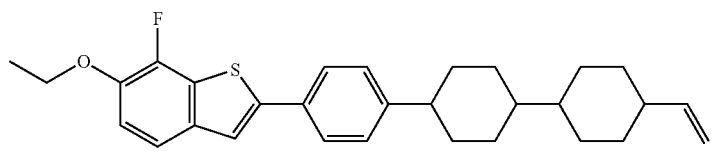 [SMILES: C=CC1CCC(C2CCC(c3ccc(-c4cc5ccc(OCC)c(F)c5s4)cc3)CC2)CC1] |

| No. | |
|---|---|
| 143 | 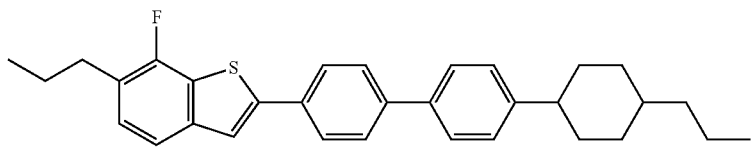 [SMILES: CCCc1ccc2cc(-c3ccc(-c4ccc(C5CCC(CCC)CC5)cc4)cc3)sc2c1F] |
| 144 | 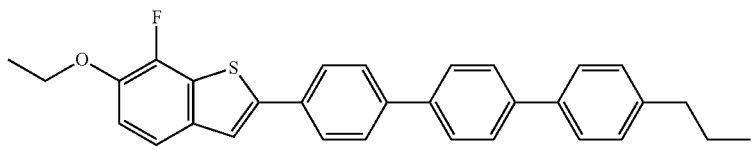 [SMILES: CCCc1ccc(-c2ccc(-c3ccc(-c4cc5ccc(OCC)c(F)c5s4)cc3)cc2)cc1] |
| 145 | 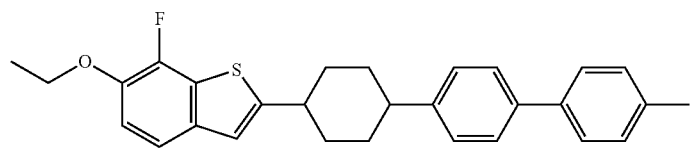 [SMILES: CCOc1ccc2cc(C3CCC(c4ccc(-c5ccc(C)cc5)cc4)CC3)sc2c1F] |
| 146 | 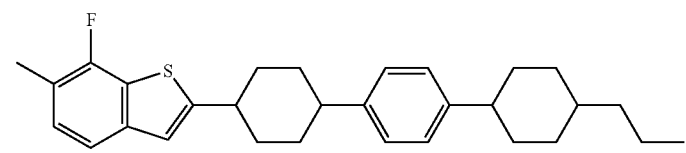 [SMILES: CCCC1CCC(c2ccc(C3CCC(c4cc5ccc(C)c(F)c5s4)CC3)cc2)CC1] |
| 147 | 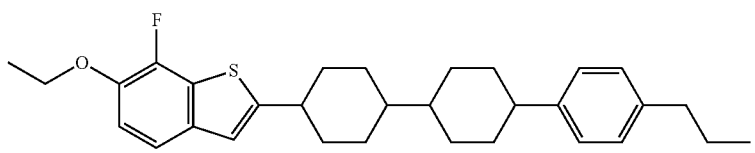 [SMILES: CCCc1ccc(C2CCC(C3CCC(c4cc5ccc(OCC)c(F)c5s4)CC3)CC2)cc1] |
| 148 | 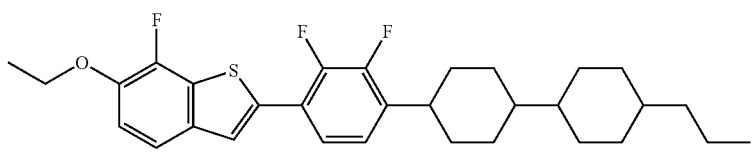 [SMILES: CCCC1CCC(C2CCC(c3ccc(-c4cc5ccc(OCC)c(F)c5s4)c(F)c3F)CC2)CC1] |
| 149 | 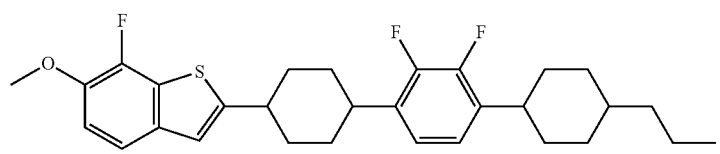 [SMILES: CCCC1CCC(c2ccc(C3CCC(c4cc5ccc(OC)c(F)c5s4)CC3)c(F)c2F)CC1] |
| 150 | 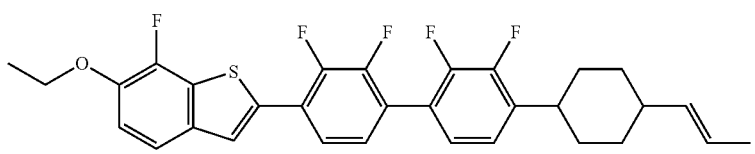 [SMILES: C/C=C/C1CCC(c2ccc(-c3ccc(-c4cc5ccc(OCC)c(F)c5s4)c(F)c3F)c(F)c2F)CC1] |
| 151 | 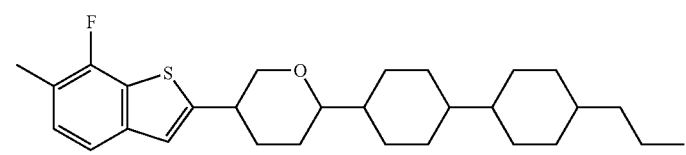 [SMILES: CCCC1CCC(C2CCC(C3CCC(c4cc5ccc(C)c(F)c5s4)CO3)CC2)CC1] |
| 152 | 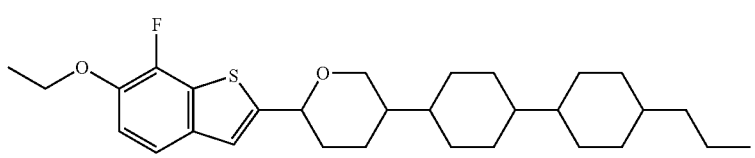 [SMILES: CCCC1CCC(C2CCC(C3CCC(c4cc5ccc(OCC)c(F)c5s4)OC3)CC2)CC1] |

| No. | |
|---|---|
| 153 | 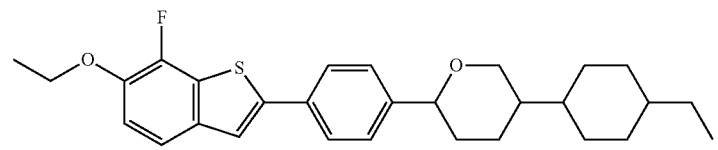 [SMILES: CCOc1ccc2cc(-c3ccc(C4CCC(C5CCC(CC)CC5)CO4)cc3)sc2c1F] |
| 154 | 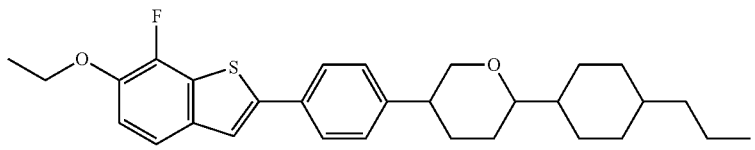 [SMILES: CCCC1CCC(C2CCC(c3ccc(-c4cc5ccc(OCC)c(F)c5s4)cc3)CO2)CC1] |
| 155 | 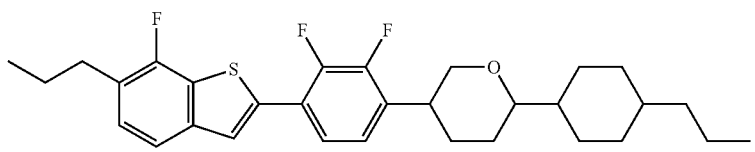 [SMILES: CCCc1ccc2cc(-c3ccc(C4CCC(C5CCC(CCC)CC5)OC4)c(F)c3F)sc2c1F] |
| 156 | 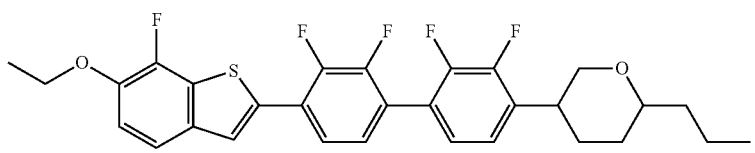 [SMILES: CCCC1CCC(c2ccc(-c3ccc(-c4cc5ccc(OCC)c(F)c5s4)c(F)c3F)c(F)c2F)CO1] |
| 157 | 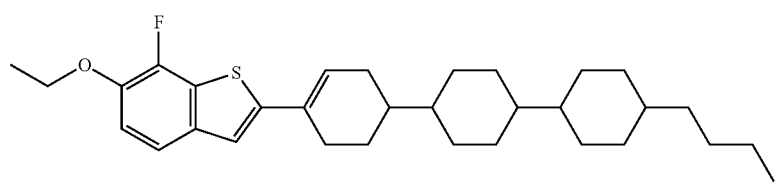 [SMILES: CCCCC1CCC(C2CCC(C3CC=C(c4cc5ccc(OCC)c(F)c5s4)CC3)CC2)CC1] |
| 158 | 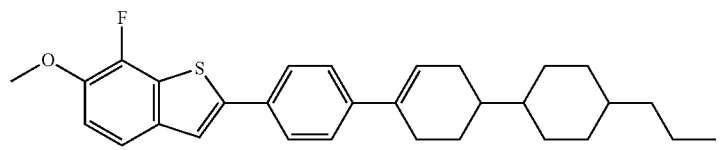 [SMILES: CCCC1CCC(C2CC=C(c3ccc(-c4cc5ccc(OC)c(F)c5s4)cc3)CC2)CC1] |
| 159 | 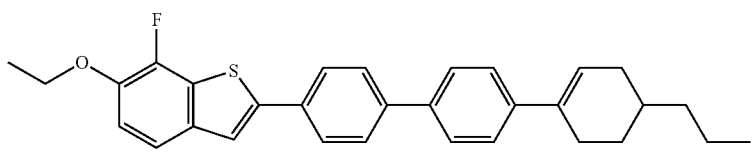 [SMILES: CCCC1CC=C(c2ccc(-c3ccc(-c4cc5ccc(OCC)c(F)c5s4)cc3)cc2)CC1] |
| 160 | 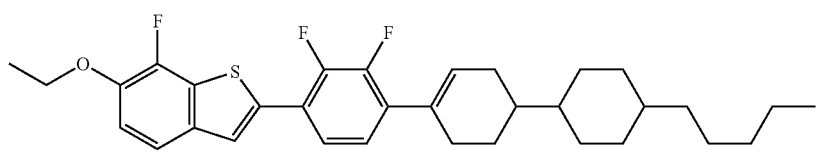 [SMILES: CCCCCC1CCC(C2CC=C(c3ccc(-c4cc5ccc(OCC)c(F)c5s4)c(F)c3F)CC2)CC1] |
| 161 | 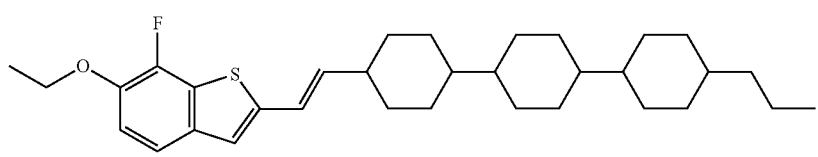 |
| 162 | 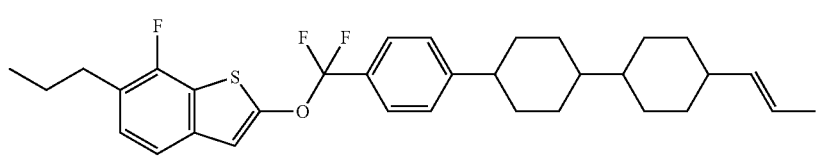 [SMILES: C/C=C/C1CCC(C2CCC(c3ccc(C(F)(F)Oc4cc5ccc(CCC)c(F)c5s4)cc3)CC2)CC1] |

| No. | |
|---|---|
| 163 | 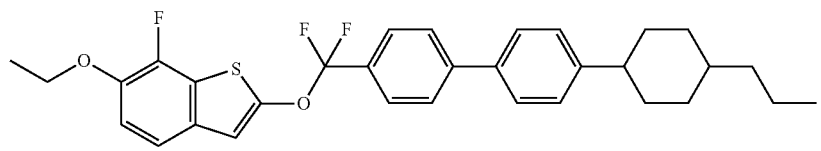 [SMILES: CCCC1CCC(c2ccc(-c3ccc(C(F)(F)Oc4cc5ccc(OCC)c(F)c5s4)cc3)cc2)CC1] |
| 164 | 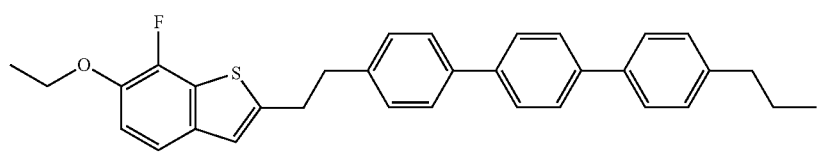 [SMILES: CCCc1ccc(-c2ccc(-c3ccc(CCc4cc5ccc(OCC)c(F)c5s4)cc3)cc2)cc1] |
| 165 | 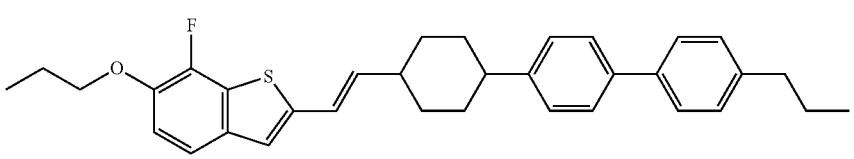 [SMILES: CCCOc1ccc2cc(/C=C/C3CCC(c4ccc(-c5ccc(CCC)cc5)cc4)CC3)sc2c1F] |
| 166 | 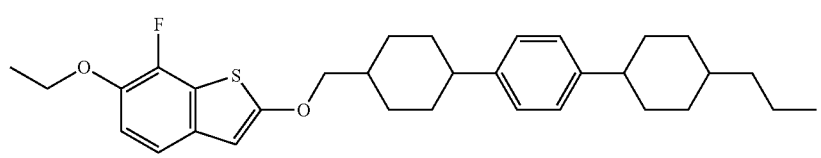 [SMILES: CCCC1CCC(c2ccc(C3CCC(COc4cc5ccc(OCC)c(F)c5s4)CC3)cc2)CC1] |
| 167 | 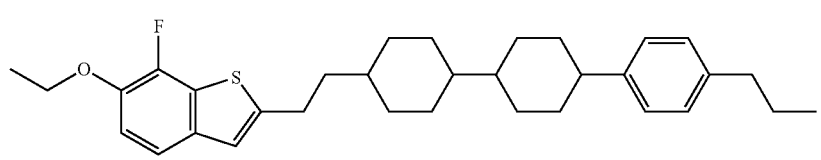 [SMILES: CCCc1ccc(C2CCC(C3CCC(CCc4cc5ccc(OCC)c(F)c5s4)CC3)CC2)cc1] |
| 168 | 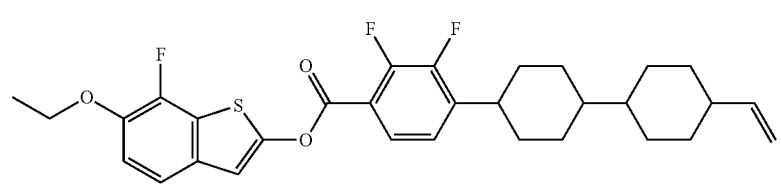 [SMILES: C=CC1CCC(C2CCC(c3ccc(C(=O)Oc4cc5ccc(OCC)c(F)c5s4)c(F)c3F)CC2)CC1] |
| 169 | 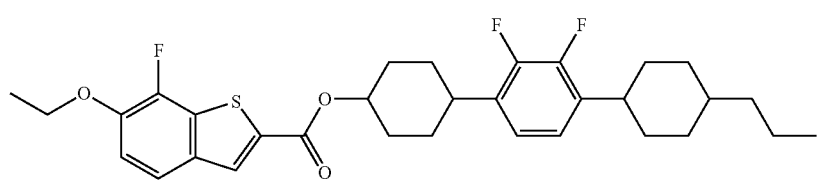 [SMILES: CCCC1CCC(c2ccc(C3CCC(OC(=O)c4cc5ccc(OCC)c(F)c5s4)CC3)c(F)c2F)CC1] |
| 170 | 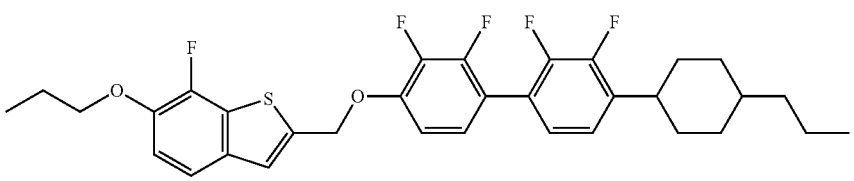 [SMILES: CCCOc1ccc2cc(COc3ccc(-c4ccc(C5CCC(CCC)CC5)c(F)c4F)c(F)c3F)sc2c1F] |
| 171 | 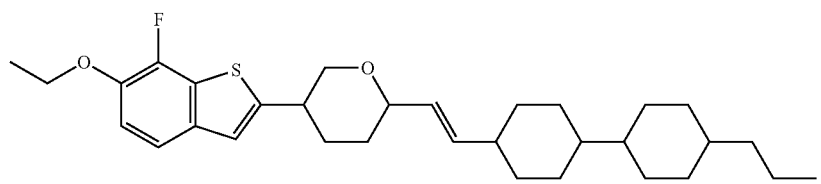 [SMILES: CCCC1CCC(C2CCC(/C=C/C3CCC(c4cc5ccc(OCC)c(F)c5s4)CO3)CC2)CC1] |

| No. | |
|---|---|
| 172 | 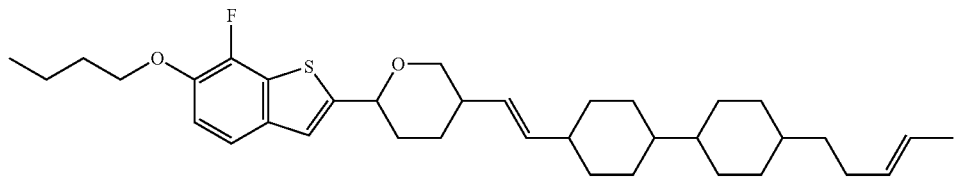 [SMILES: C/C=C/CCC1CCC(C2CCC(/C=C/C3CCC(c4cc5ccc(OCCCC)c(F)c5s4)OC3)CC2)CC1] |
| 173 | 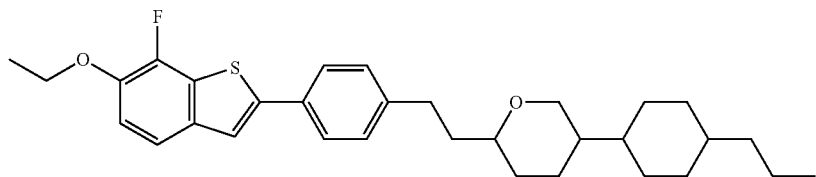 [SMILES: CCCC1CCC(C2CCC(CCc3ccc(-c4cc5ccc(OCC)c(F)c5s4)cc3)OC2)CC1] |
| 174 | 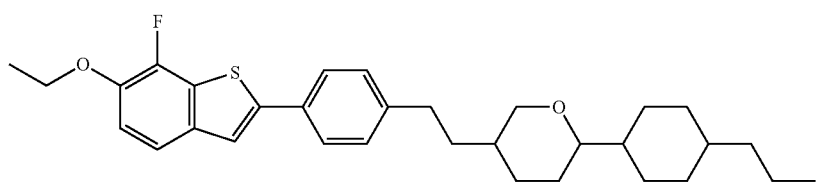 [SMILES: CCCC1CCC(C2CCC(CCc3ccc(-c4cc5ccc(OCC)c(F)c5s4)cc3)CO2)CC1] |
| 175 | 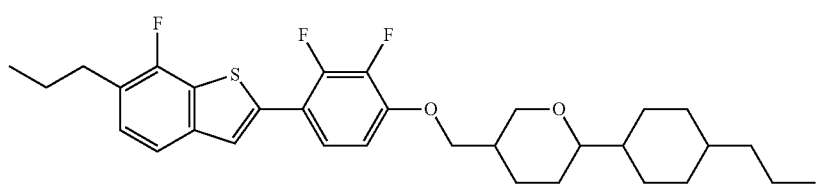 [SMILES: CCCc1ccc2cc(-c3ccc(OCC4CCC(C5CCC(CCC)CC5)OC4)c(F)c3F)sc2c1F] |
| 176 | 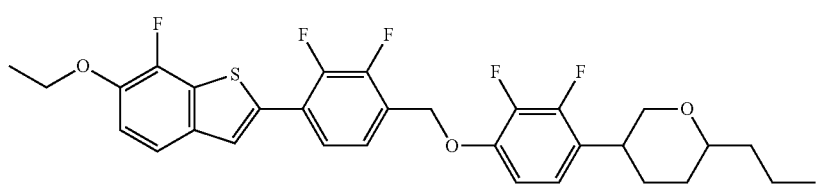 [SMILES: CCCC1CCC(c2ccc(OCc3ccc(-c4cc5ccc(OCC)c(F)c5s4)c(F)c3F)c(F)c2F)CO1] |
| 177 | 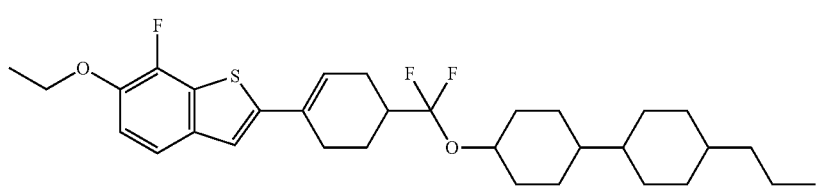 [SMILES: CCCC1CCC(C2CCC(OC(F)(F)C3CC=C(c4cc5ccc(OCC)c(F)c5s4)CC3)CC2)CC1] |
| 178 | 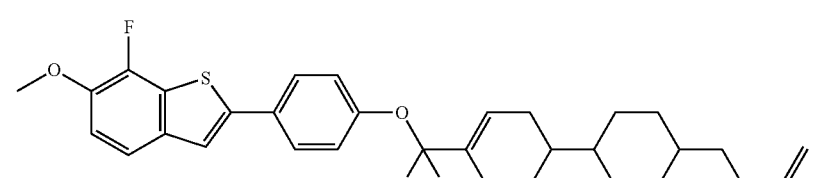 |
| 179 | 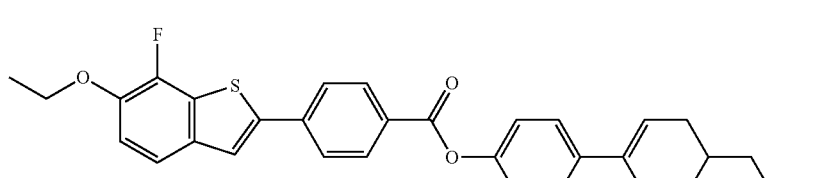 |

-continued
| No. | |
|---|---|
| 180 | 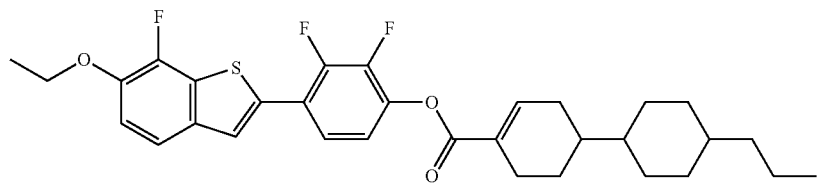 [SMILES: CCCC1CCC(C2CC=C(C(=O)Oc3ccc(-c4cc5ccc(OCC)c(F)c5s4)c(F)c3F)CC2)CC1] |
| 181 | 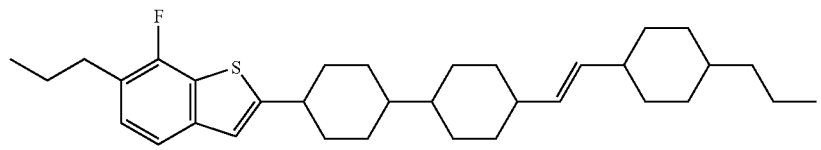 [SMILES: CCCc1ccc2cc(C3CCC(C4CCC(/C=C/C5CCC(CCC)CC5)CC4)CC3)sc2c1F] |
| 182 | 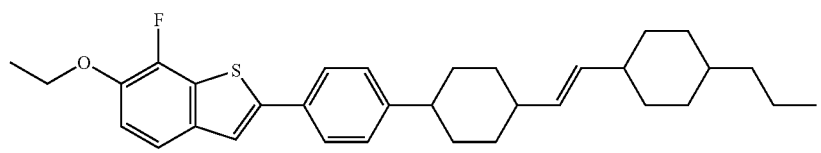 [SMILES: CCCC1CCC(/C=C/C2CCC(c3ccc(-c4cc5ccc(OCC)c(F)c5s4)cc3)CC2)CC1] |
| 183 | 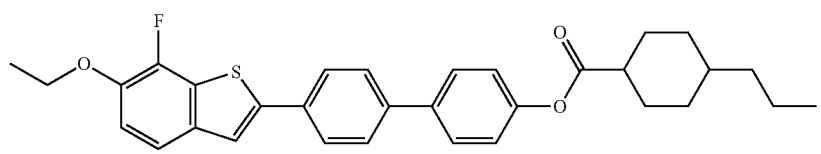 [SMILES: CCCC1CCC(C(=O)Oc2ccc(-c3ccc(-c4cc5ccc(OCC)c(F)c5s4)cc3)cc2)CC1] |
| 184 | 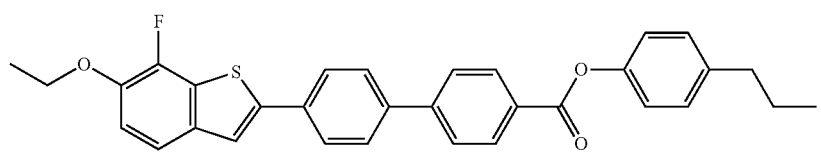 [SMILES: CCCc1ccc(OC(=O)c2ccc(-c3ccc(-c4cc5ccc(OCC)c(F)c5s4)cc3)cc2)cc1] |
| 185 | 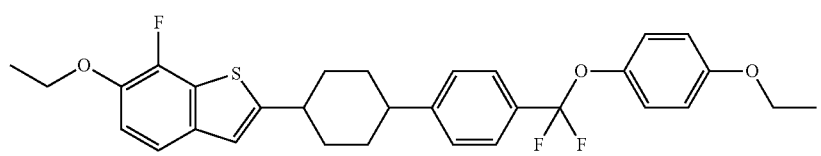 [SMILES: CCOc1ccc(OC(F)(F)c2ccc(C3CCC(c4cc5ccc(OCC)c(F)c5s4)CC3)cc2)cc1] |
| 186 | 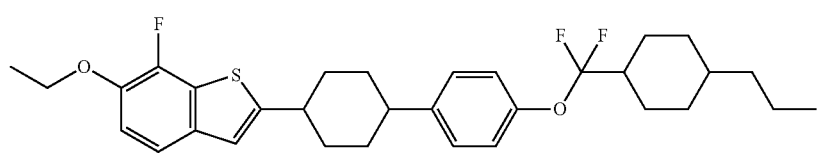 [SMILES: CCCC1CCC(C(F)(F)Oc2ccc(C3CCC(c4cc5ccc(OCC)c(F)c5s4)CC3)cc2)CC1] |
| 187 | 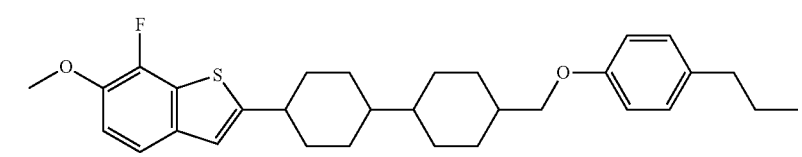 [SMILES: CCCc1ccc(OCC2CCC(C3CCC(c4cc5ccc(OC)c(F)c5s4)CC3)CC2)cc1] |
| 188 | 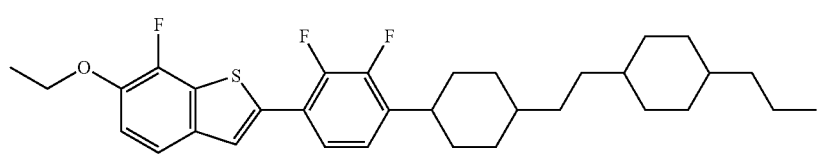 [SMILES: CCCC1CCC(CCC2CCC(c3ccc(-c4cc5ccc(OCC)c(F)c5s4)c(F)c3F)CC2)CC1] |

| No. | |
|---|---|
| 189 | 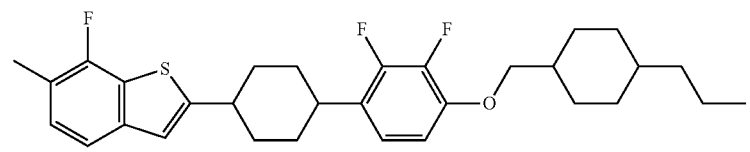 [SMILES: CCCC1CCC(COc2ccc(C3CCC(c4cc5ccc(C)c(F)c5s4)CC3)c(F)c2F)CC1] |
| 190 | 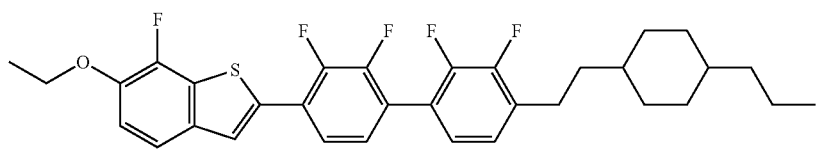 [SMILES: CCCC1CCC(CCc2ccc(-c3ccc(-c4cc5ccc(OCC)c(F)c5s4)c(F)c3F)c(F)c2F)CC1] |
| 191 | 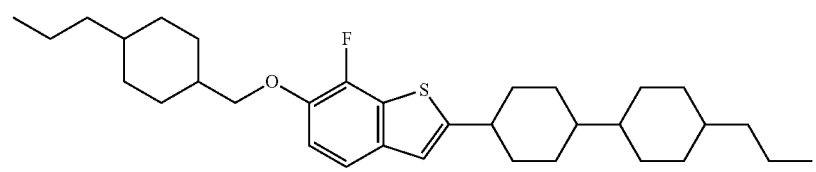 [SMILES: CCCC1CCC(COc2ccc3cc(C4CCC(C5CCC(CCC)CC5)CC4)sc3c2F)CC1] |
| 192 | 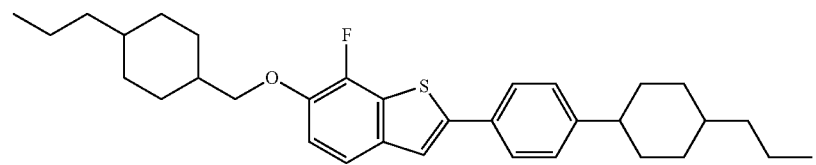 [SMILES: CCCC1CCC(COc2ccc3cc(-c4ccc(C5CCC(CCC)CC5)cc4)sc3c2F)CC1] |
| 193 | 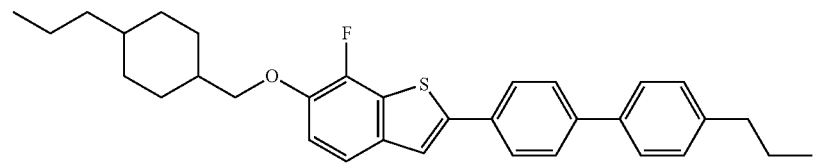 [SMILES: CCCc1ccc(-c2ccc(-c3cc4ccc(OCC5CCC(CCC)CC5)c(F)c4s3)cc2)cc1] |
| 194 | 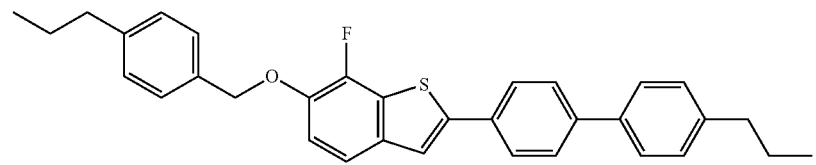 [SMILES: CCCc1ccc(COc2ccc3cc(-c4ccc(-c5ccc(CCC)cc5)cc4)sc3c2F)cc1] |
| 195 | 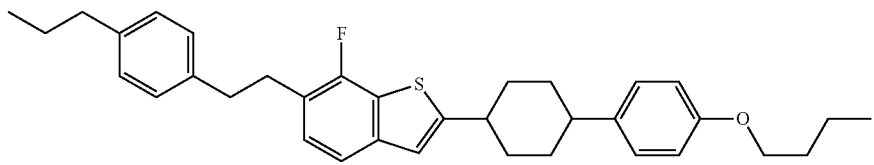 [SMILES: CCCCOc1ccc(C2CCC(c3cc4ccc(CCc5ccc(CCC)cc5)c(F)c4s3)CC2)cc1] |
| 196 | 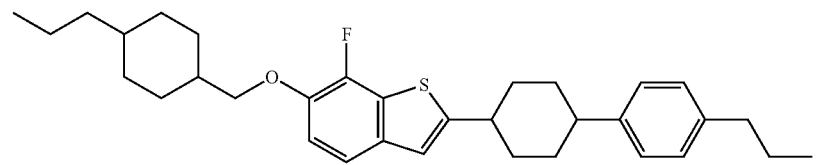 [SMILES: CCCc1ccc(C2CCC(c3cc4ccc(OCC5CCC(CCC)CC5)c(F)c4s3)CC2)cc1] |
| 197 | 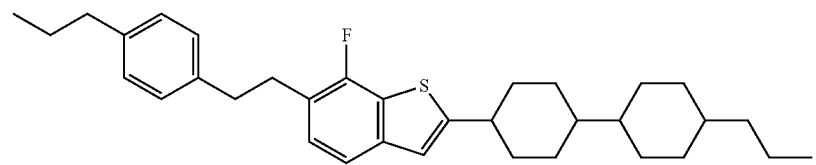 [SMILES: CCCc1ccc(CCc2ccc3cc(C4CCC(C5CCC(CCC)CC5)CC4)sc3c2F)cc1] |

-continued
| No. | |
|---|---|
| 198 | 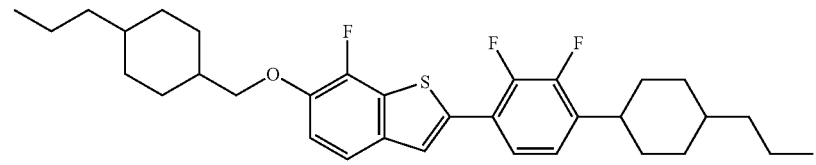 [SMILES: CCCC1CCC(COc2ccc3cc(-c4ccc(C5CCC(CCC)CC5)c(F)c4F)sc3c2F)CC1] |
| 199 | 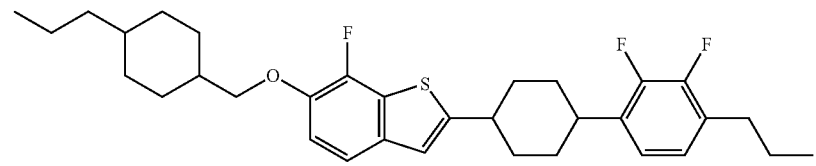 [SMILES: CCCc1ccc(C2CCC(c3cc4ccc(OCC5CCC(CCC)CC5)c(F)c4s3)CC2)c(F)c1F] |
| 200 | 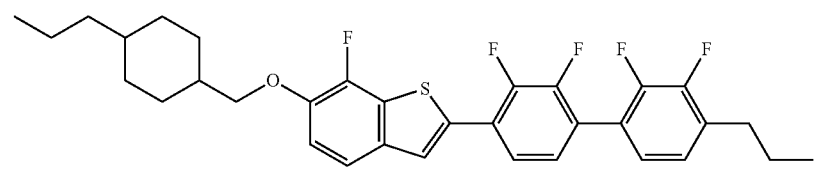 [SMILES: CCCc1ccc(-c2ccc(-c3cc4ccc(OCC5CCC(CCC)CC5)c(F)c4s3)c(F)c2F)c(F)c1F] |
| 201 | 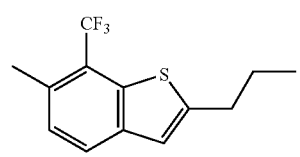 [SMILES: CCCc1cc2ccc(C)c(C(F)(F)F)c2s1] |
| 202 |  |
| 203 | 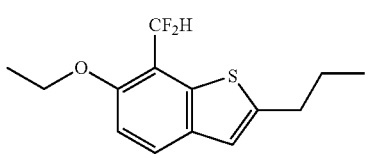 [SMILES: CCCc1cc2ccc(OCC)c(C(F)F)c2s1] |
| 204 | 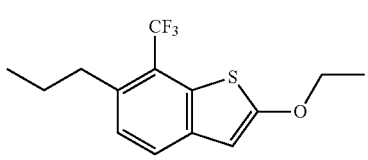 [SMILES: CCCc1ccc2cc(OCC)sc2c1C(F)(F)F] |
| 205 | 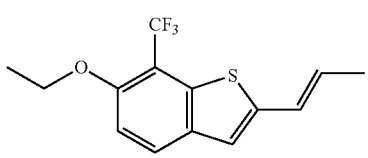 [SMILES: C/C=C/c1cc2ccc(OCC)c(C(F)(F)F)c2s1] |
| 206 | 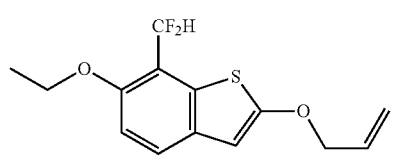 |

| No. | |
|---|---|
| 207 | 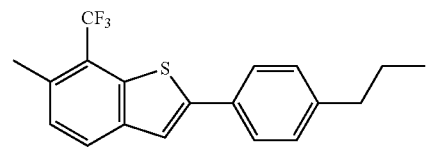 [SMILES: CCCc1ccc(-c2cc3ccc(C)c(C(F)(F)F)c3s2)cc1] |
| 208 | 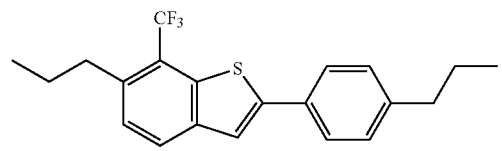 [SMILES: CCCc1ccc(-c2cc3ccc(CCC)c(C(F)(F)F)c3s2)cc1] |
| 209 | 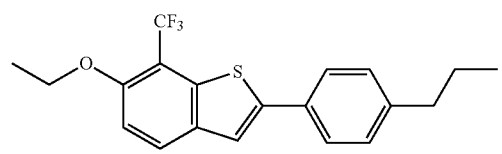 [SMILES: CCCc1ccc(-c2cc3ccc(OCC)c(C(F)(F)F)c3s2)cc1] |
| 210 | 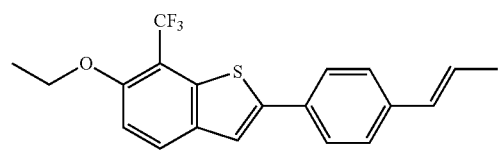 [SMILES: C/C=C/c1ccc(-c2cc3ccc(OCC)c(C(F)(F)F)c3s2)cc1] |
| 211 | 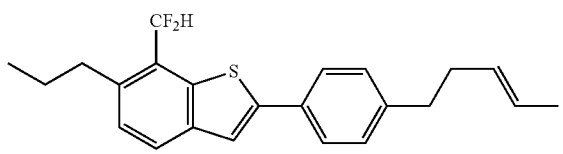 [SMILES: C/C=C/CCc1ccc(-c2cc3ccc(CCC)c(C(F)F)c3s2)cc1] |
| 212 | 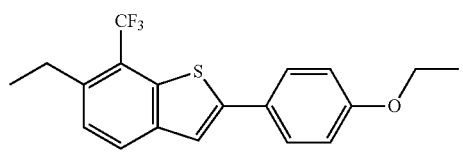 [SMILES: CCOc1ccc(-c2cc3ccc(CC)c(C(F)(F)F)c3s2)cc1] |
| 213 | 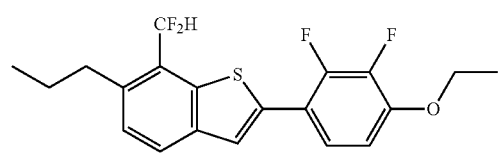 [SMILES: CCCc1ccc2cc(-c3ccc(OCC)c(F)c3F)sc2c1C(F)F] |
| 214 | 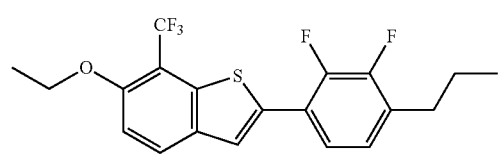 [SMILES: CCCc1ccc(-c2cc3ccc(OCC)c(C(F)(F)F)c3s2)c(F)c1F] |
| 215 | 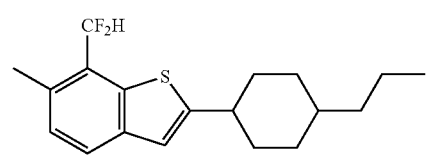 [SMILES: CCCC1CCC(c2cc3ccc(C)c(C(F)F)c3s2)CC1] |
| 216 | 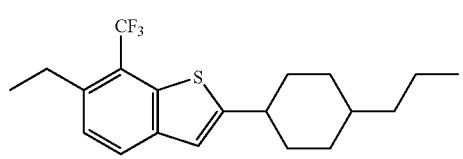 [SMILES: CCCC1CCC(c2cc3ccc(CC)c(C(F)(F)F)c3s2)CC1] |

-continued
| No. | |
|---|---|
| 217 | 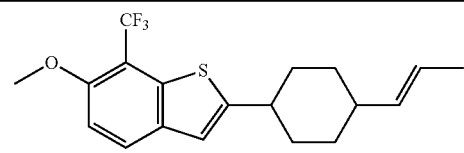 |
| 218 | 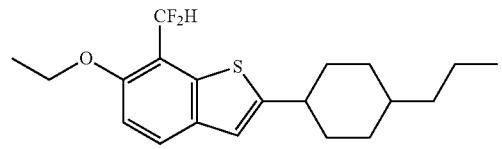 [SMILES: CCCC1CCC(c2cc3ccc(OCC)c(C(F)F)c3s2)CC1] |
| 219 | 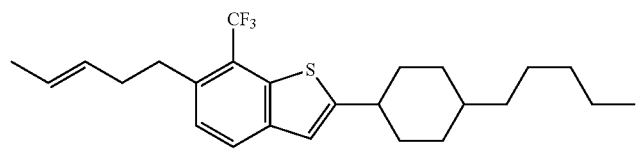 [SMILES: C/C=C/CCc1ccc2cc(C3CCC(CCCCC)CC3)sc2c1C(F)(F)F] |
| 220 | 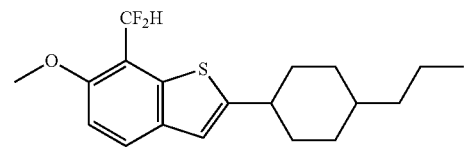 |
| 221 | 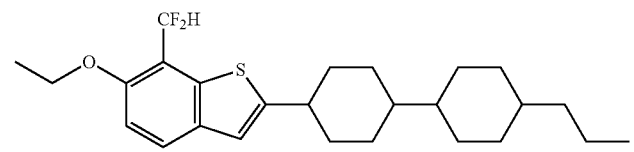 |
| 222 | 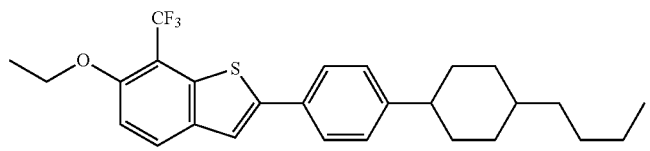 |
| 223 | 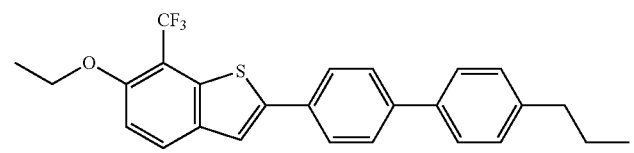 [SMILES: CCCc1ccc(-c2ccc(-c3cc4ccc(OCC)c(C(F)(F)F)c4s3)cc2)cc1] |
| 224 | 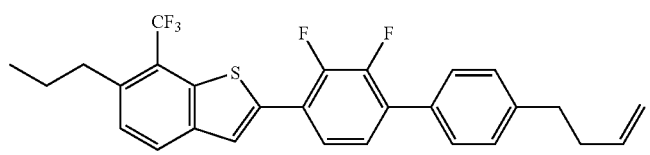 |
| 225 | 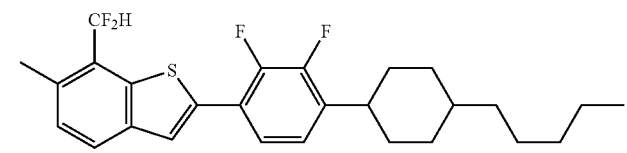 [SMILES: CCCCCC1CCC(c2ccc(-c3cc4ccc(C)c(C(F)F)c4s3)c(F)c2F)CC1] |
| 226 | 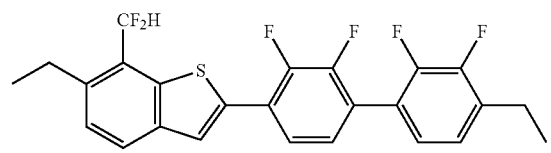 [SMILES: CCc1ccc(-c2ccc(-c3cc4ccc(CC)c(C(F)F)c4s3)c(F)c2F)c(F)c1F] |

-continued
| No. | |
|---|---|
| 227 | 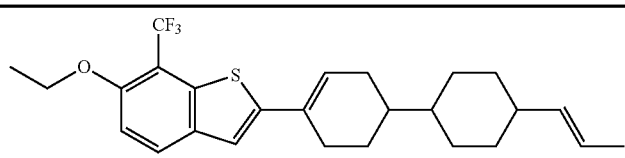 |
| 228 | 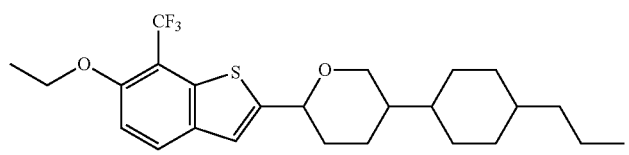 [SMILES: CCCC1CCC(C2CCC(c3cc4ccc(OCC)c(C(F)(F)F)c4s3)OC2)CC1] |
| 229 | 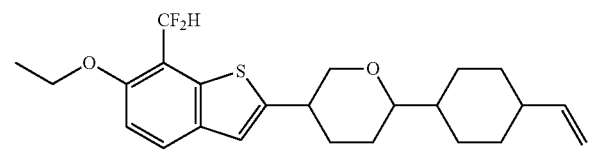 [SMILES: C=CC1CCC(C2CCC(c3cc4ccc(OCC)c(C(F)F)c4s3)CO2)CC1] |
| 230 | 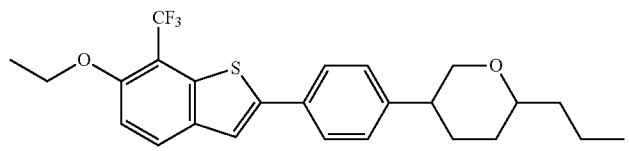 |
| 231 | 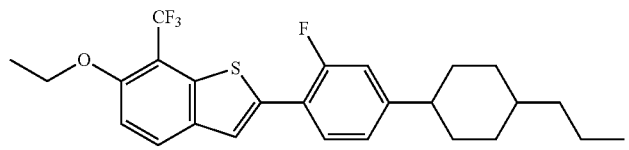 |
| 232 | 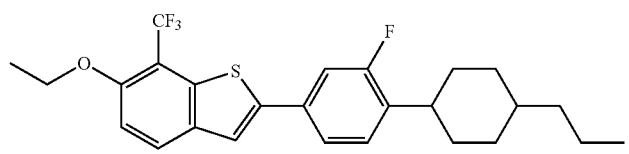 [SMILES: CCCC1CCC(c2ccc(-c3cc4ccc(OCC)c(C(F)(F)F)c4s3)cc2F)CC1] |
| 233 | 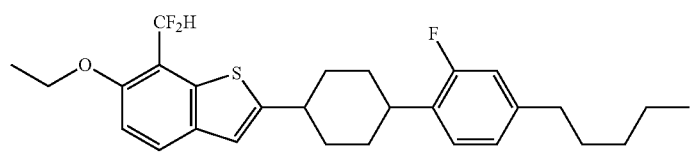 [SMILES: CCCCCc1ccc(C2CCC(c3cc4ccc(OCC)c(C(F)F)c4s3)CC2)c(F)c1] |
| 234 | 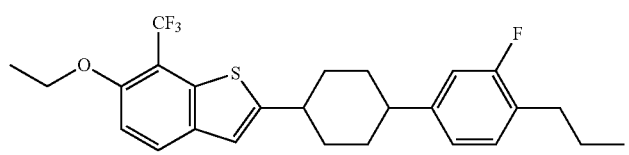 [SMILES: CCCc1ccc(C2CCC(c3cc4ccc(OCC)c(C(F)(F)F)c4s3)CC2)cc1F] |
| 235 | 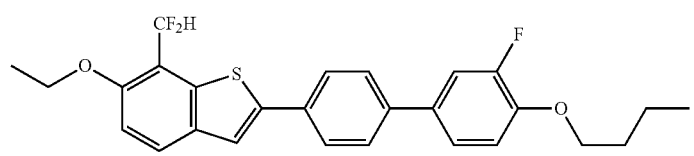 |
| 236 | 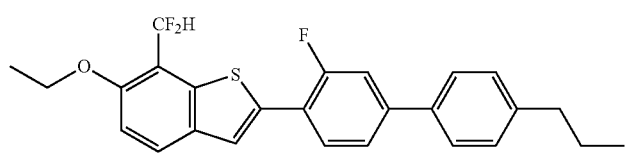 |

| No. | |
|---|---|
| 237 | 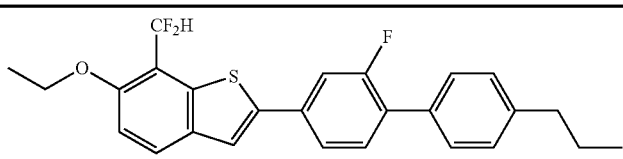 |
| 238 | 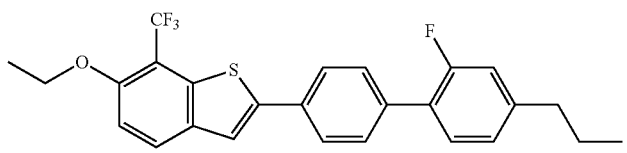 |
| 239 | 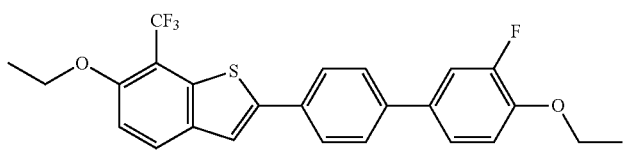 |
| 240 | 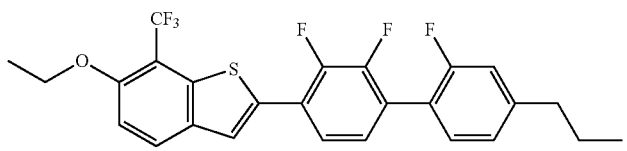 |

Comparative Example 1

Comparative compound (C-1) that is similar to the compound described in Examples in Patent literature No. 1 was prepared, in which an ethoxy group in a 6-position moves to a 5-position, and further fluorine is introduced to the 6-position in comparison with compound (No. 9).

Synthesis of Comparative Compound (C-1)

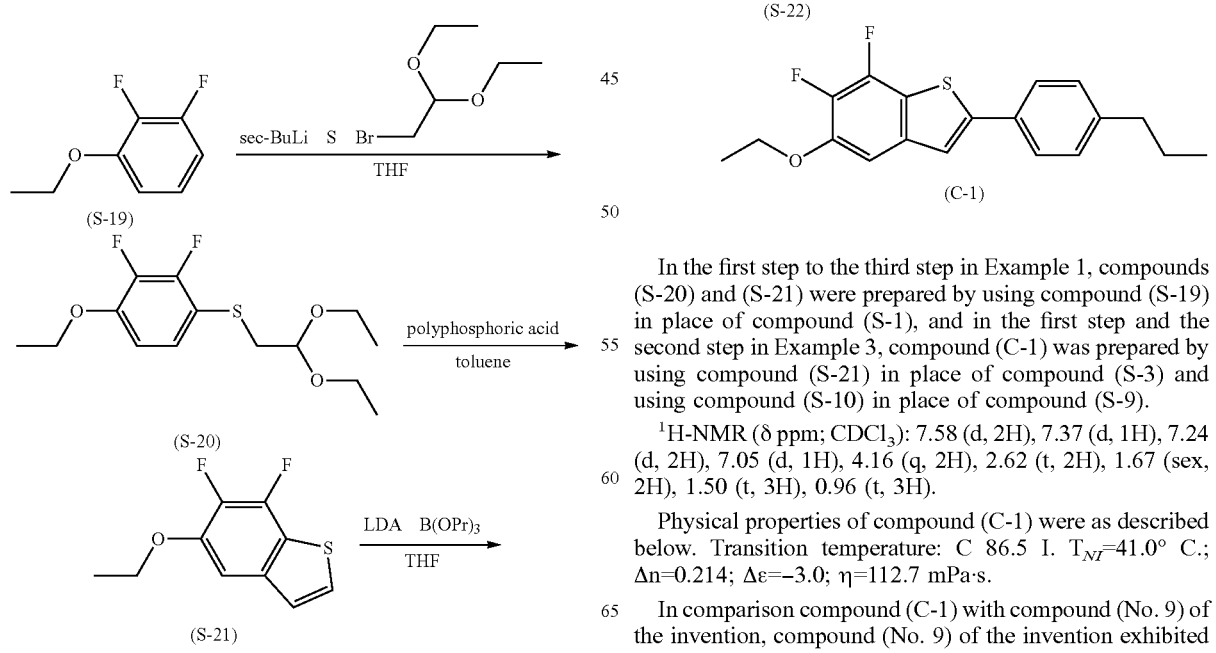

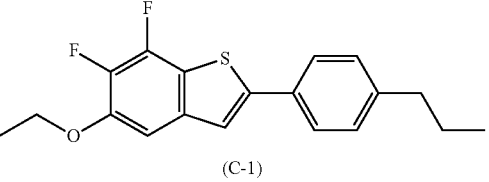

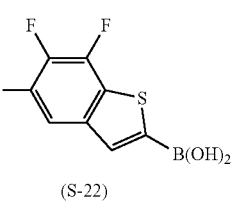

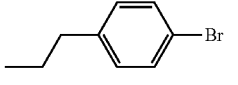

In the first step to the third step in Example 1, compounds (S-20) and (S-21) were prepared by using compound (S-19) in place of compound (S-1), and in the first step and the second step in Example 3, compound (C-1) was prepared by using compound (S-21) in place of compound (S-3) and using compound (S-10) in place of compound (S-9).

$^1$H-NMR (δ ppm; CDCl$_3$): 7.58 (d, 2H), 7.37 (d, 1H), 7.24 (d, 2H), 7.05 (d, 1H), 4.16 (q, 2H), 2.62 (t, 2H), 1.67 (sex, 2H), 1.50 (t, 3H), 0.96 (t, 3H).

Physical properties of compound (C-1) were as described below. Transition temperature: C 86.5 I. $T_{NI}$=41.0° C.; Δn=0.214; Δε=−3.0; η=112.7 mPa·s.

In comparison compound (C-1) with compound (No. 9) of the invention, compound (No. 9) of the invention exhibited larger negative dielectric anisotropy (Δε=−3.83), higher maximum temperature ($T_{NI}$=101), smaller viscosity (η=38.8) and larger optical anisotropy (Δn=0.287).

1-2. Example of Composition (1)

Liquid crystal composition (1) of the invention will be described in detail by way of Examples. The compounds in Examples were represented using symbols according to definitions in a table described below. In Table 1, the configuration of 1,4-cyclohexylene is trans. A parenthesized number next to a symbolized compound in Examples corresponds to the number of the compound. A symbol (-) means any other liquid crystal compound. A proportion (percentage) of the liquid crystal compound is expressed in terms of weight percent (% by weight) based on the total weight of the liquid crystal composition. Values of the physical properties of the composition are summarized in a last part. The physical properties were measured according to the methods described above, and measured values are directly described without extrapolation.

TABLE 1

Method for Description of Compounds using Symbols
R—(A$_1$)—Z$_1$— . . . —Z$_n$—(A$_n$)—R'

| 1) Left-terminal Group R- | Symbol |
|---|---|
| $C_nH_{2n+1}$— | n- |
| $C_nH_{2n+1}O$— | nO— |
| $C_mH_{2m+1}OC_nH_{2n}$— | mOn- |
| $CH_2=CH$— | V— |
| $C_nH_{2n+1}$—CH=CH— | nV— |
| $CH_2=CH$—$C_nH_{2n}$— | Vn- |
| $C_mH_{2m+1}$—CH=CH—$C_nH_{2n}$— | mVn- |
| $CF_2=CH$— | VFF— |
| $CF_2=CH$—$C_nH_{2n}$— | VFFn- |

| 2) Right-terminal Group -R' | Symbol |
|---|---|
| —$C_nH_{2n+1}$ | -n |
| —$OC_nH_{2n+1}$ | —On |
| —$COOCH_3$ | -Eme |
| —$CH=CH_2$ | —V |
| —CH=CH—$C_nH_{2n+1}$ | —Vn |
| —$C_nH_{2n}$—CH=$CH_2$ | -nV |
| —$C_mH_{2m}$—CH=CH—$C_nH_{2n+1}$ | -mVn |
| —CH=$CF_2$ | —VFF |
| —F | —F |
| —Cl | —CL |
| —$OCF_3$ | —OCF3 |
| —$OCF_2H$ | —OCF2H |
| —$CF_3$ | —CF3 |
| —OCH=CH—$CF_3$ | —OVCF3 |
| —C≡N | —C |

| 3) Bonding Group -Z$_n$- | Symbol |
|---|---|
| —$C_nH_{2n}$— | n |
| —COO— | E |
| —CH=CH— | V |
| —$CH_2O$— | 1O |
| —$OCH_2$— | O1 |
| —$CF_2O$— | X |
| —$OCF_2$— | x |
| —C≡C— | T |

| 4) Ring Structure -A$_n$- | Symbol |
|---|---|
| 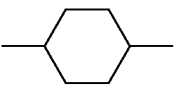 | H |
|  | B |

TABLE 1-continued

Method for Description of Compounds using Symbols
R—(A$_1$)—Z$_1$— . . . —Z$_n$—(A$_n$)—R'

| | |
|---|---|
| 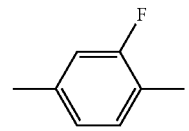 | B(F) |
| 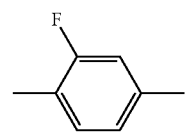 | B(2F) |
| 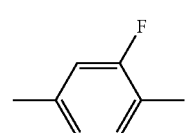 | B(F,F) |
| 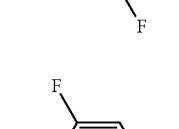 | B(2F,5F) |
| 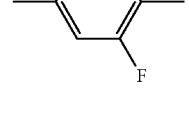 | B(2F,3F) |
| 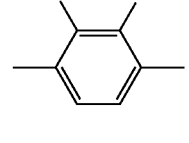 | Py |
| 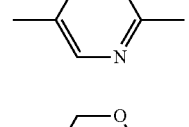 | G |
| 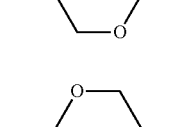 | Dh |
| 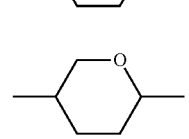 | dh |
| 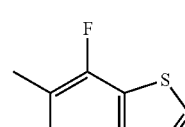 | bt(7F) |

TABLE 1-continued

Method for Description of Compounds using Symbols
R—(A₁)—Z₁— . . . —$Z_n$—($A_n$)—R'

5) Examples of Description

Example 1  2O-bt(7F)H-3

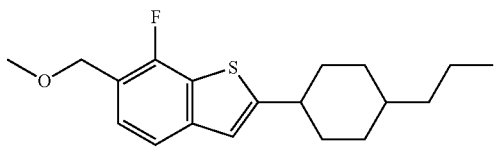

Example 2  3-BB(F,F)XB(F,F)-F

Example 16

| 2O-bt(7F)H-3 | (No. 18) | 5% |
|---|---|---|
| 3-HB-O2 | (13-5) | 10% |
| 5-HB-CL | (2-2) | 13% |
| 3-HBB(F,F)-F | (3-24) | 7% |
| 3-PyB(F)-F | (3-81) | 10% |
| 5-PyB(F)-F | (3-81) | 10% |
| 3-PyBB-F | (3-80) | 10% |
| 4-PyBB-F | (3-80) | 8% |
| 5-PyBB-F | (3-80) | 7% |
| 5-HBB(F)B-2 | (15-5) | 10% |
| 5-HBB(F)B-3 | (15-5) | 10% |

NI=96.5° C.; η=38.8 mPa·s; Δn=0.186; Δε=7.2.

Example 17

| 2O-bt(7F)2H-3 | (No. 25) | 4% |
|---|---|---|
| 2-HB-C | (5-1) | 5% |
| 3-HB-C | (5-1) | 11% |
| 3-HB-O2 | (13-5) | 14% |
| 2-BTB-1 | (13-10) | 3% |
| 3-HHB-F | (3-1) | 4% |
| 3-HHB-1 | (14-1) | 8% |
| 3-HHB-O1 | (14-1) | 5% |
| 3-HHB-3 | (14-1) | 14% |
| 3-HHEB-F | (3-10) | 4% |
| 5-HHEB-F | (3-10) | 3% |
| 2-HHB(F)-F | (3-2) | 7% |
| 3-HHB(F)-F | (3-2) | 6% |
| 5-HHB(F)-F | (3-2) | 7% |
| 3-HHB(F,F)-F | (3-3) | 5% |

Example 18

| 2O-bt(7F)2H-3 | (No. 25) | 5% |
|---|---|---|
| 7-HB(F,F)-F | (2-3) | 3% |
| 3-HB-O2 | (13-5) | 7% |
| 2-HHB(F)-F | (3-2) | 9% |
| 3-HHB(F)-F | (3-2) | 9% |
| 5-HHB(F)-F | (3-2) | 9% |
| 2-HBB(F)-F | (3-23) | 9% |
| 3-HBB(F)-F | (3-23) | 9% |
| 5-HBB(F)-F | (3-23) | 14% |
| 2-HBB-F | (3-22) | 4% |
| 3-HBB-F | (3-22) | 4% |
| 5-HBB-F | (3-22) | 3% |
| 3-HBB(F,F)-F | (3-24) | 6% |
| 5-HBB(F,F)-F | (3-24) | 9% |

NI=83.4° C.; η=25.4 mPa·s; Δn=0.117; Δε=5.4.

Example 19

| 3-HH1Obt(7F)-3 | (No. 105) | 5% |
|---|---|---|
| 5-HB-CL | (2-2) | 13% |
| 3-HH-4 | (13-1) | 12% |
| 3-HH-5 | (13-1) | 4% |
| 3-HHB-F | (3-1) | 4% |
| 3-HHB-CL | (3-1) | 3% |
| 4-HHB-CL | (3-1) | 4% |
| 3-HHB(F)-F | (3-2) | 10% |
| 4-HHB(F)-F | (3-2) | 8% |
| 5-HHB(F)-F | (3-2) | 8% |
| 7-HHB(F)-F | (3-2) | 8% |
| 5-HBB(F)-F | (3-23) | 3% |
| 1O1-HBBH-5 | (15-1) | 3% |
| 3-HHBB(F,F)-F | (4-6) | 3% |
| 4-HHBB(F,F)-F | (4-6) | 3% |
| 5-HHBB(F,F)-F | (4-6) | 3% |
| 3-HH2BB(F,F)-F | (4-15) | 3% |
| 4-HH2BB(F,F)-F | (4-15) | 3% |

NI=120.2° C.; η=21.6 mPa·s; Δn=0.094; Δε=3.5.

Example 20

| 2O-bt(7F)BB-3 | (No. 43) | 1% |
|---|---|---|
| 2O-bt(7F)HVH-3 | (No. 73) | 2% |
| 3-HHB(F,F)-F | (3-3) | 9% |
| 3-H2HB(F,F)-F | (3-15) | 7% |
| 4-H2HB(F,F)-F | (3-15) | 8% |
| 5-H2HB(F,F)-F | (3-15) | 8% |
| 3-HBB(F,F)-F | (3-24) | 20% |
| 5-HBB(F,F)-F | (3-24) | 20% |
| 3-H2BB(F,F)-F | (3-27) | 9% |
| 5-HHBB(F,F)-F | (4-6) | 3% |
| 5-HHEBB-F | (4-17) | 2% |
| 3-HH2BB(F,F)-F | (4-15) | 3% |
| 1O1-HBBH-4 | (15-1) | 4% |
| 1O1-HBBH-5 | (15-1) | 4% |

Example 21

| 3-bt(7F)B-3 | (No. 8) | 4% |
|---|---|---|
| 5-HB-F | (2-2) | 12% |
| 6-HB-F | (2-2) | 9% |
| 7-HB-F | (2-2) | 7% |
| 2-HHB-OCF3 | (3-1) | 7% |
| 3-HHB-OCF3 | (3-1) | 7% |
| 4-HHB-OCF3 | (3-1) | 7% |
| 5-HHB-OCF3 | (3-1) | 5% |
| 3-HH2B-OCF3 | (5-36) | 4% |

-continued

| | | |
|---|---|---|
| 5-HH2B-OCF3 | (5-36) | 4% |
| 3-HHB(F,F)-OCF2H | (5-30) | 3% |
| 3-HHB(F,F)-OCF3 | (5-30) | 5% |
| 3-HH2B(F)-F | (5-37) | 3% |
| 3-HBB(F)-F | (5-32) | 8% |
| 5-HBB(F)-F | (5-32) | 9% |
| 5-HBBH-3 | (15-1) | 3% |
| 3-HB(F)BH-3 | (15-2) | 3% |

NI=84.5° C.; η=15.1 mPa·s; Δn=0.097; Δε=4.1.

Example 22

| | | |
|---|---|---|
| 2O-bt(7F)B-3 | (No. 9) | 5% |
| 5-HB-CL | (2-2) | 11% |
| 3-HH-4 | (13-1) | 8% |
| 3-HHB-1 | (14-1) | 5% |
| 3-HHB(F,F)-F | (3-3) | 7% |
| 3-HBB(F,F)-F | (3-24) | 20% |
| 5-HBB(F,F)-F | (3-24) | 14% |
| 3-HHEB(F,F)-F | (3-12) | 9% |
| 4-HHEB(F,F)-F | (3-12) | 3% |
| 5-HHEB(F,F)-F | (3-12) | 3% |
| 2-HBEB(F,F) F | (3-39) | 3% |
| 3-HBEB(F,F)-F | (3-39) | 4% |
| 5-HBEB(F,F)-F | (3-39) | 3% |
| 3-HHBB(F,F)-F | (4-6) | 5% |

NI=80.3° C.; η=21.9 mPa·s; Δn=0.112; Δε=8.0.

Example 23

| | | |
|---|---|---|
| 2O-B(2F,3F)bt(7F)-3 | (No. 35) | 5% |
| 3-HB-CL | (2-2) | 6% |
| 5-HB-CL | (2-2) | 4% |
| 3-HHB-OCF3 | (3-1) | 5% |
| 3-H2HB-OCF3 | (3-13) | 5% |
| 5-H4HB-OCF3 | (3-13) | 13% |
| V-HHB(F)-F | (3-3) | 5% |
| 3-HHB(F)-F | (3-3) | 4% |
| 5-HHB(F)-F | (3-3) | 5% |
| 3-H4HB(F,F)-CF3 | (3-21) | 8% |
| 5-H4HB(F,F)-CF3 | (3-21) | 9% |
| 5-H2HB(F,F)-F | (3-15) | 5% |
| 5-H4HB(F,F)-F | (3-21) | 7% |
| 2-H2BB(F)-F | (3-14) | 4% |
| 3-H2BB(F)-F | (3-14) | 10% |
| 3-HBEB(F,F)-F | (3-39) | 5% |

Example 24

| | | |
|---|---|---|
| 2O-bt(7F)B(2F,3F)-O2 | (No. 14) | 5% |
| 5-HB-CL | (2-2) | 17% |
| 7-HB(F,F)-F | (2-4) | 3% |
| 3-HH-4 | (13-1) | 10% |
| 3-HH-5 | (13-1) | 3% |
| 3-HB-O2 | (13-5) | 12% |
| 3-HHB-1 | (14-1) | 8% |
| 3-HHB-O1 | (14-1) | 5% |
| 2-HHB(F)-F | (3-2) | 7% |
| 3-HHB(F)-F | (3-2) | 7% |
| 5-HHB(F)-F | (3-2) | 7% |
| 3-HHB(F,F)-F | (3-3) | 6% |
| 3-H2HB(F,F)-F | (3-15) | 5% |
| 4-H2HB(F,F)-F | (3-15) | 5% |

Example 25

| | | |
|---|---|---|
| 2O-bt(7F)1OB(2F,3F)-O2 | (No. 32) | 5% |
| 5-HB-CL | (2-2) | 3% |
| 7-HB(F)-F | (2-3) | 6% |
| 3-HH-4 | (13-1) | 8% |
| 3-HH-EMe | (13-2) | 22% |
| 3-HHEB-F | (3-10) | 8% |
| 5-HHEB-F | (3-10) | 8% |
| 3-HHEB(F,F)-F | (3-12) | 10% |
| 4-HHEB(F,F)-F | (3-12) | 4% |
| 4-HGB(F,F)-F | (3-103) | 4% |
| 5-HGB(F,F)-F | (3-103) | 6% |
| 2-H2GB(F,F)-F | (3-106) | 4% |
| 3-H2GB(F,F)-F | (3-106) | 5% |
| 5-GHB(F,F)-F | (3-109) | 7% |

Example 26

| | | |
|---|---|---|
| 3-Dhbt(7F)-3 | (No. 37) | 4% |
| 1V2-BEB(F,F)-C | (5-15) | 6% |
| 3-HB-C | (5-1) | 15% |
| 2-BTB-1 | (13-10) | 10% |
| 5-HH-VFF | (13-1) | 29% |
| 3-HHB-1 | (14-1) | 4% |
| VFF-HHB-1 | (14-1) | 8% |
| VFF2-HHB-1 | (14-1) | 11% |
| 3-H2BTB-2 | (14-17) | 5% |
| 3-H2BTB-3 | (14-17) | 4% |
| 3-H2BTB-4 | (14-17) | 4% |

Example 27

| | | |
|---|---|---|
| 2O-bt(7F)xH-3 | (No. 30) | 5% |
| 3-GB(F)B(F,F)XB(F,F)-F | (4-57) | 5% |
| 3-BB(F)B(F,F)XB(F,F)-F | (4-47) | 3% |
| 4-BB(F)B(F,F)XB(F,F)-F | (4-47) | 5% |
| 5-BB(F)B(F,F)XB(F,F)-F | (4-47) | 3% |
| 3-HH-V | (13-1) | 41% |
| 3-HH-V1 | (13-1) | 6% |
| 3-HHEH-5 | (14-13) | 3% |
| 3-HHB-1 | (14-1) | 4% |
| V-HHB-1 | (14-1) | 4% |
| V2-BB(F)B-1 | (14-6) | 5% |
| 1V2-BB-F | (2-1) | 3% |
| 3-BB(F,F)XB(F,F)-F | (3-97) | 10% |
| 3-HHBB(F,F)-F | (4-6) | 3% |

Example 28

| | | |
|---|---|---|
| 2O-bt(7F)dh-3 | (No. 24) | 5% |
| 3-GB(F)B(F,F)XB(F,F)-F | (4-57) | 5% |
| 3-BB(F)B(F,F)XB(F,F)-F | (4-47) | 3% |
| 4-BB(F)B(F,F)XB(F,F)-F | (4-47) | 6% |
| 5-BB(F)B(F,F)XB(F,F)-F | (4-47) | 3% |
| 3-HH-V | (13-1) | 38% |
| 3-HH-V1 | (13-1) | 7% |
| 3-HHEH-5 | (14-13) | 3% |
| 3-HHB-1 | (14-1) | 4% |
| V-HHB-1 | (14-1) | 4% |
| V2-BB(F)B-1 | (14-6) | 5% |
| 1V2-BB-F | (2-1) | 3% |
| 3-BB(F,F)XB(F,F)-F | (3-97) | 6% |
| 3-GB(F,F)XB(F,F)-F | (3-113) | 5% |
| 3-HHBB(F,F)-F | (4-6) | 3% |

Example 29

| | | |
|---|---|---|
| 2O-bt(7F)B(2F)B-3 | (No. 56) | 3% |
| 2O-bt(7F)B(2F,3F)-O2 | (No. 14) | 1% |
| 7-HB(F,F)-F | (2-3) | 3% |
| 3-HB-O2 | (13-5) | 7% |
| 2-HHB(F)-F | (3-2) | 8% |
| 3-HHB(F)-F | (3-2) | 9% |
| 5-HHB(F)-F | (3-2) | 9% |
| 2-HBB(F)-F | (3-23) | 9% |
| 3-HBB(F)-F | (3-23) | 9% |
| 5-HBB(F)-F | (3-23) | 16% |
| 2-HBB-F | (3-22) | 4% |
| 3-HBB-F | (3-22) | 4% |
| 5-HBB-F | (3-22) | 3% |
| 3-HBB(F,F)-F | (3-24) | 5% |
| 5-HBB(F,F)-F | (3-24) | 10% |

NI=89.2° C.; η=26.5 mPa·s; Δn=0.127; Δε=5.7.

Example 30

| | | |
|---|---|---|
| 2O-bt(7F)B(2F)B-5 | (No. 241) | 3% |
| 2O-bt(7F)B(2F,3F)O1H-3 | (No. 243) | 1% |
| 5-HB-F | (2-2) | 12% |
| 6-HB-F | (2-2) | 9% |
| 7-HB-F | (2-2) | 7% |
| 2-HHB-OCF3 | (3-1) | 7% |
| 3-HHB-OCF3 | (3-1) | 5% |
| 4-HHB-OCF3 | (3-1) | 7% |
| 5-HHB-OCF3 | (3-1) | 5% |
| 3-HH2B-OCF3 | (5-36) | 4% |
| 5-HH2B-OCF3 | (5-36) | 4% |
| 3-HHB(F,F)-OCF2H | (5-30) | 3% |
| 3-HHB(F,F)-OCF3 | (5-30) | 4% |
| 3-HH2B(F)-F | (5-37) | 3% |
| 3-HBB(F)-F | (5-32) | 10% |
| 5-HBB(F)-F | (5-32) | 10% |
| 5-HBBH-3 | (15-1) | 3% |
| 3-HB(F)BH-3 | (15-2) | 3% |

NI=89.0° C.; η=16.2 mPa·s; Δn=0.102; Δε=4.4.

Example 31

| | | |
|---|---|---|
| 2O-bt(7F)B(2F)B-O4 | (No. 242) | 3% |
| 2O-bt(7F)B(F,F)XB(F,F)-F | (No. 247) | 1% |
| 5-HB-CL | (2-2) | 3% |
| 7-HB(F)-F | (2-3) | 7% |
| 3-HH-4 | (13-1) | 9% |
| 3-HH-EMe | (13-2) | 22% |
| 3-HHEB-F | (3-10) | 8% |
| 5-HHEB-F | (3-10) | 8% |
| 3-HHEB(F,F)-F | (3-12) | 10% |
| 4-HHEB(F,F)-F | (3-12) | 5% |
| 4-HGB(F,F)-F | (3-103) | 4% |
| 5-HGB(F,F)-F | (3-103) | 5% |
| 2-H2GB(F,F)-F | (3-106) | 4% |
| 3-H2GB(F,F)-F | (3-106) | 5% |
| 5-GHB(F,F)-F | (3-109) | 6% |

NI=84.4° C.; η=21.5 mPa·s; Δn=0.076; Δε=6.0.

Example 32

| | | |
|---|---|---|
| 2O-bt(7F)B(2F)-3 | (No. 244) | 4% |
| 2O-bt(7F)B(2F)-4 | (No. 249) | 5% |
| 3-HB-O2 | (13-5) | 10% |
| 5-HB-CL | (2-2) | 11% |
| 3-HBB(F,F)-F | (3-24) | 8% |
| 3-PyB(F)-F | (3-81) | 10% |
| 5-PyB(F)-F | (3-81) | 10% |
| 3-PyBB-F | (3-80) | 7% |
| 4-PyBB-F | (3-80) | 8% |
| 5-PyBB-F | (3-80) | 9% |
| 5-HBB(F)B-2 | (15-5) | 9% |
| 5-HBB(F)B-3 | (15-5) | 9% |

NI=99.7° C.; η=40.7 mPa·s; Δn=0.119; Δε=7.7.

INDUSTRIAL APPLICABILITY

A liquid crystal compound of the invention has high stability to heat, light and so forth, a high clearing point, low minimum temperature of a liquid crystal phase, small viscosity, suitable optical anisotropy, large negative dielectric anisotropy, a suitable elastic constant and excellent compatibility with other liquid crystal compounds. A liquid crystal composition of the invention contains the compound, and has high maximum temperature of a nematic phase, low minimum temperature of the nematic phase, small viscosity, suitable optical anisotropy, large negative dielectric anisotropy and a suitable elastic constant. The composition has a suitable balance regarding at least two of physical properties. A liquid crystal display device of the invention includes the composition, and has a wide temperature range in which the device can be used, a short response time, a large voltage holding ratio, low threshold voltage, a large contrast ratio and along service life. Accordingly, the device can be widely used in a display of a personal computer, a television and so forth.

What is claimed is:
1. A compound, represented by formula (1):

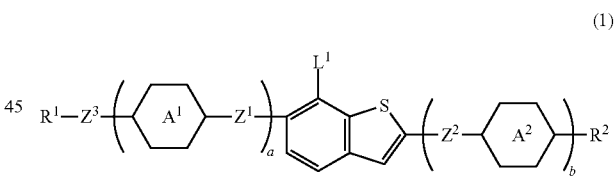

(1)

wherein, in formula (1),
$R^1$ and $R^2$ are independently hydrogen, halogen or alkyl having 1 to 20 carbons, and in the alkyl, at least one piece of —$CH_2$— may be replaced by —O— or —S—, at least one piece of —$(CH_2)_2$— may replace by —CH=CH—, and in the groups, at least one piece of hydrogen may be replaced by halogen;
ring $A^1$ and ring $A^2$ are independently 1,4-cyclohexylene, 1,4-cyclohexenylene, 1,4-phenylene, tetrahydropyran-2,5-diyl, 1,3-dioxane-2,5-diyl, pyrimidine-2,5-diyl, 2,6,7-trioxabicyclo[2.2.2]octane-1,4-diyl, naphthalene-2,6-diyl, or pyridine-2,5-diyl, and at least one piece of hydrogen on the rings may be replaced by halogen;
$Z^1$ and $Z^2$ are independently a single bond or alkylene having 1 to 4 carbons, in the alkylene, at least one piece of —$CH_2$— may be replaced by —O— or —COO—, and at least one piece of —$(CH_2)_2$— may replace by —CH═CH— or —C≡C—, and in the groups, at least one piece of hydrogen may be replaced by halogen;

Z³ is —O— or a single bond;

L¹ is F, CF₃ or CF₂H; and a and b are independently 0, 1, 2, 3 or 4, and a sum of a and b is 4 or less, and when a or b is 2 or more, two of arbitrary ring A¹, two of arbitrary ring A², two pieces of arbitrary Z¹ or two pieces of arbitrary Z² may be identical or different.

2. The compound according to claim 1, represented by formula (1-2):

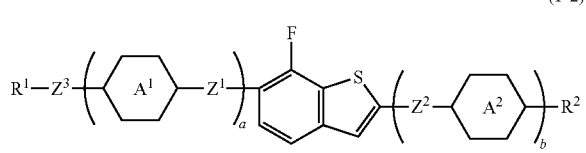

(1-2)

wherein, in formula (1-2),

R¹ and R² are independently hydrogen, halogen or alkyl having 1 to 20 carbons, and in the alkyl, at least one piece of —CH₂— may be replaced by —O— or —S—, at least one piece of —(CH₂)₂— may replace by —CH═CH—, and in the groups, at least one piece of hydrogen may be replaced by halogen;

ring A¹ and ring A² are independently 1,4-cyclohexylene, 1,4-cyclohexenylene, 1,4-phenylene, tetrahydropyran-2,5-diyl, 1,3-dioxane-2,5-diyl, pyrimidine-2,5-diyl, 2,6,7-trioxabicyclo[2.2.2]octane-1,4-diyl, naphthalene-2,6-diyl, or pyridine-2,5-diyl, and at least one piece of hydrogen on the rings may be replaced by halogen;

Z¹ and Z² are independently a single bond or alkylene having 1 to 4 carbons, in the alkylene, at least one piece of —CH₂— may be replaced by —O— or —COO—, and at least one piece of —(CH₂)₂— may replace by —CH═CH— or and in the groups, at least one piece of hydrogen may be replaced by halogen;

Z³ is —O— or a single bond; and a and b are independently 0, 1, 2, 3 or 4, and a sum of a and b is 4 or less, and when a or b is 2 or more, two of ring A¹ and A², and two of Z¹ and Z² may be identical or different.

3. The compound according to claim 2, wherein, in formula (1-2), R¹ and R² are independently chlorine, fluorine, alkyl having 1 to 10 carbons, alkoxy having 1 to 9 carbons, alkenyl having 2 to 10 carbons, polyfluoroalkyl having 1 to 10 carbons or polyfluoroalkyl having 1 to 9 carbons;

ring A¹ and ring A² are independently 1,4-cyclohexylene, 1,4-cyclohexenylene, 1,4-phenylene in which at least one piece of hydrogen may be replaced by halogen, or tetrahydropyran-2,5-diyl;

Z¹ and Z² are independently a single bond, —(CH₂)₂—, —CH═CH—, —CF═CF—, —COO—, —OCO—, —CF₂O—, —OCF₂—, —CH₂O—, —OCH₂—, —(CH₂)₄—, —(CH₂)₂CF₂O—, —(CH₂)₂OCF₂-₅—CF₂O(CH₂)₂—, —OCF₂(CH₂)₂—CH═CH—(CH₂)₂— or —(CH₂)₂—CH═CH—; and a and b are independently 0, 1, 2, 3 or 4, and a sum of a and b is 4 or less.

4. The compound according to claim 2, wherein, in formula (1-2), a sum of a and b is 0, 1, 2 or 3;

R¹ and R² are independently chlorine, fluorine, alkyl having 1 to 10 carbons, alkoxy having 1 to 9 carbons, alkenyl having 2 to 10 carbons, polyfluoroalkyl having 1 to 10 carbons or polyfluoroalkyl having 1 to 9 carbons;

ring A¹ and ring A² are independently 1,4-cyclohexylene, 1,4-cyclohexenylene, 1,4-phenylene in which at least one piece of hydrogen may be replaced by halogen, tetrahydropyran-2,5-diyl; and Z¹ and Z² are independently a single bond, —(CH₂)₂—, —CH═CH—, —CF═CF—, —C≡C—, —COO—, —OCO—, —CF₂O—, —OCF₂—, —CH₂O—, —OCH₂—, —(CH₂)₄—, —(CH₂)₂CF₂O—, —(CH₂)₂OCF₂—CF₂O(CH₂)₂—, —OCF₂(CH₂)₂—CH═CH—(CH₂)₂— or —(CH₂)₂—CH═CH—.

5. The compound according to claim 1, represented by any one of formulas (1-2-1) to (1-2-10):

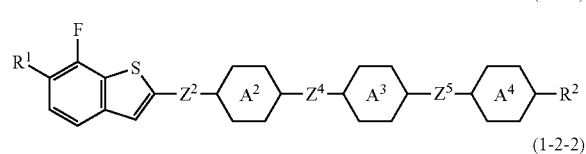

(1-2-1)

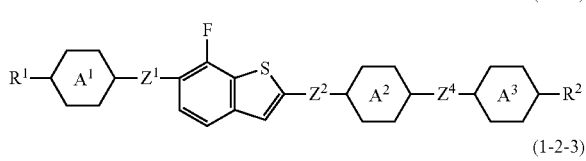

(1-2-2)

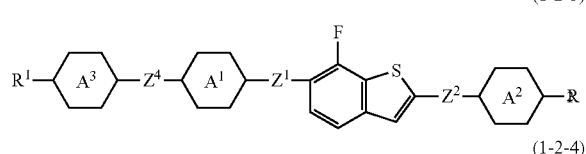

(1-2-3)

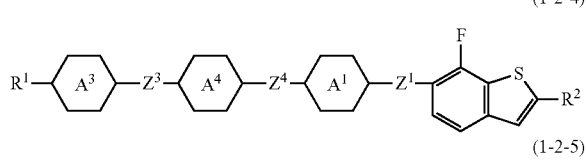

(1-2-4)

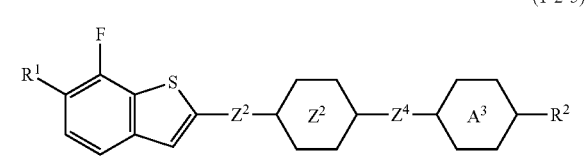

(1-2-5)

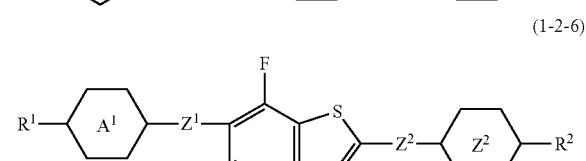

(1-2-6)

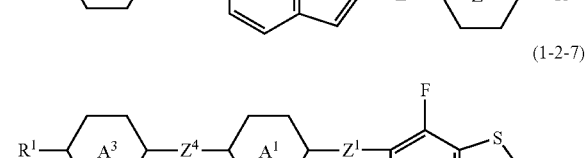

(1-2-7)

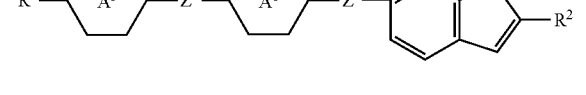

(1-2-8)

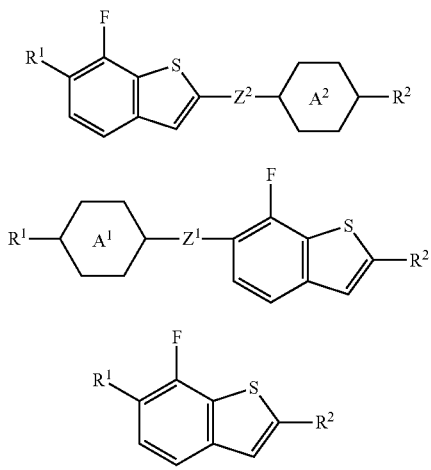

(1-2-9)

(1-2-10)

(1-2-7)

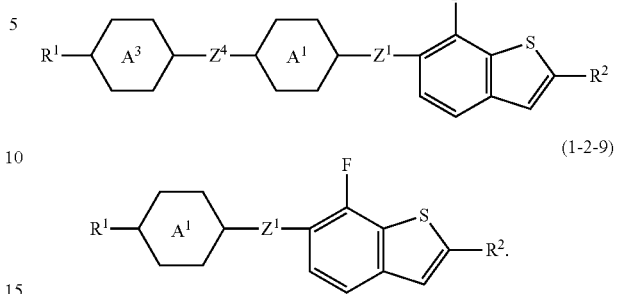

(1-2-9)

wherein, in formulas (1-2-1) to (1-2-10), $R^1$ and $R^2$ are independently chlorine, fluorine, alkyl having 1 to 10 carbons, alkoxy having 1 to 9 carbons, alkenyl having 2 to 10 carbons, polyfluoroalkyl having 1 to 10 carbons or polyfluoroalkyl having 1 to 9 carbons;

ring $A^1$, ring $A^2$, ring $A^3$ and ring $A^4$ are independently 1,4-cyclohexylene, 1,4-cyclohexenylene, 1,4-phenylene, 1,4-phenylene in which at least one piece of hydrogen is replaced by halogen, or tetrahydropyran-2,5-diyl; and $Z^1$, $Z^2$, $Z^4$ and $Z^5$ are independently a single bond, —(CH$_2$)$_2$—CH=CH—, —CF=CF—, —C≡C—, —COO—, —OCO—, —CF$_2$O—, —OCF$_2$—, —CH$_2$O—, —OCH$_2$—, —(CH$_2$)$_4$—, —(CH$_2$)$_2$CF$_2$O—, —(CH$_2$)$_2$OCF$_2$—CF$_2$O(CH$_2$)$_2$—, —OCF$_2$(CH$_2$)$_2$—CH=CH—(CH$_2$)$_2$— or —(CH$_2$)$_2$—CH=CH—.

6. The compound according to claim 5, wherein, in formulas (1-2-1) to (1-2-10), $R^1$ and $R^2$ are independently fluorine, alkyl having 1 to 10 carbons, alkoxy having 1 to 9 carbons, alkenyl having 2 to 10 carbons or polyfluoroalkyl having 1 to 9 carbons;

ring $A^1$, ring $A^2$, ring $A^3$ and ring $A^4$ are independently 1,4-cyclohexylene, 1,4-cyclohexenylene, 1,4-phenylene in which at least one piece of hydrogen may be replaced by halogen, or tetrahydropyran-2,5-diyl; and $Z^1$, $Z^2$, $Z^4$ and $Z^5$ are independently a single bond, —(CH$_2$)$_2$—CH=CH—, —CF$_2$O—, —OCF$_2$—, —CH$_2$O— or —OCH$_2$—.

7. The compound according to claim 6, represented by any one of formulas (1-2-4), (1-2-7) and (1-2-9):

(1-2-4)

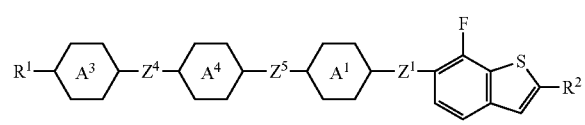

8. The compound according to claim 6, represented by any one of formulas (1-2-1), (1-2-5), (1-2-8) and (1-2-10), wherein, $R^1$ is alkoxy having 1 to 6 carbons:

(1-2-1)

(1-2-5)

(1-2-8)

(1-2-10)

9. A liquid crystal composition, containing at least one compound according to claim 1.

10. The liquid crystal composition according to claim 9, further containing at least one compound selected from the group of compounds represented by formulas (6) to (12):

(6)

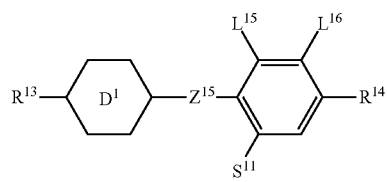

(7)

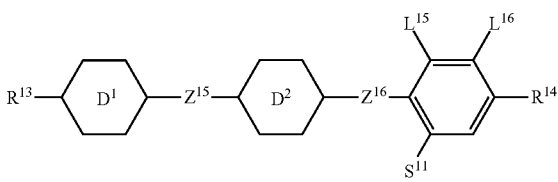

-continued

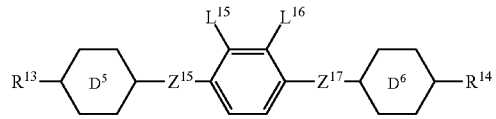
(8)

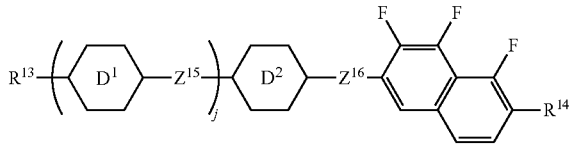
(9)

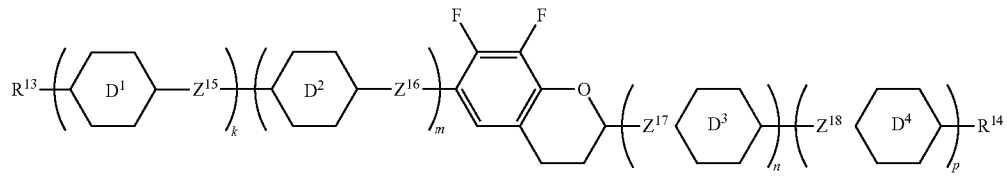
(10)

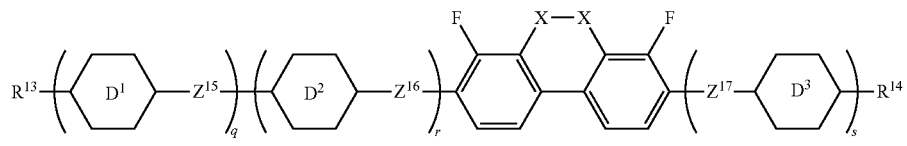
(11)

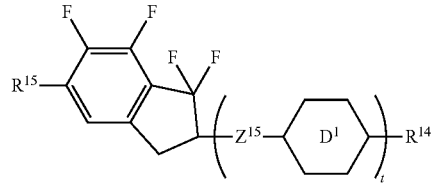
(12)

wherein in formulas (6) to (12),
R$^{13}$ is alkyl having 1 to 10 carbons or alkenyl having 2 to 10 carbons, and in the alkyl and the alkenyl, at least one piece of —CH$_2$— may be replaced by —O—, and at least one piece of hydrogen may be replaced by fluorine;
R$^{14}$ is alkyl having 1 to 10 carbons, in the alkyl, at least one piece of —CH$_2$— may be replaced by —O—, and at least one piece of hydrogen may be replaced by fluorine;
R$^{15}$ is hydrogen, fluorine, alkyl having 1 to 10 carbons or alkenyl having 2 to 10 carbons, and in the alkyl and the alkenyl, at least one piece of —CH$_2$— may be replaced by —O—, and at least one piece of hydrogen may be replaced by fluorine;
S$^{11}$ is hydrogen or methyl;
X is —CF$_2$—, —O— or —CHF—;
ring D$^1$, ring D$^2$, ring D$^3$ and ring D$^4$ are independently 1,4-cyclohexylene, 1,4-cyclohexenylene, 1,4-phenylene in which at least one piece of hydrogen may be replaced by fluorine, tetrahydropyran-2,5-diyl, or decahydronaphthalene-2,6-diyl;
ring D$^5$ and ring D$^6$ are independently 1,4-cyclohexylene, 1,4-cyclohexenylene, 1,4-phenylene, tetrahydropyran-2,5-diyl or decahydronaphthalene-2,6-diyl;
Z$^{15}$, Z$^{16}$, Z$^{17}$ and Z$^{18}$ are independently a single bond, —CH$_2$CH$_2$—, —OCO—, —CH$_2$O—, —OCF$_2$— or —OCF$_2$CH$_2$CH$_2$—;
L$^{15}$ and L$^{16}$ are independently fluorine or chlorine; and
j, k, m, n, p, q, r and s are independently 0 or 1, a sum of k, m, n and p is 1 or 2, and a sum of q, r and s is 0, 1, 2 or 3, and t is 1, 2 or 3.

11. The liquid crystal composition according to claim 9, further containing at least one compound selected from the group of compounds represented by formulas (13) to (15):

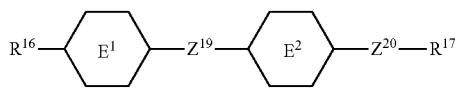
(13)

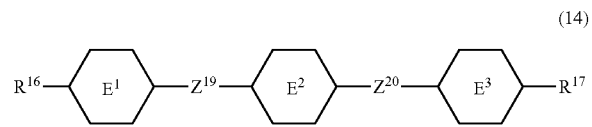
(14)

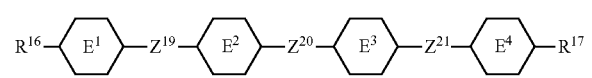
(15)

wherein in formulas (13) to (15),
R$^{16}$ and R$^{17}$ are independently alkyl having 1 to 10 carbons or alkenyl having 2 to 10 carbons, and in the alkyl and the alkenyl, at least one piece of —CH$_2$— may be replaced by —O—, and at least one piece of hydrogen may be replaced by fluorine;
ring E$^1$, ring E$^2$, ring E$^3$ and ring E$^4$ are independently 1,4-cyclohexylene, 1,4-phenylene, 2-fluoro-1,4-phenylene, 2,5-difluoro-1,4-phenylene or pyrimidine-2,5-diyl; and
Z$^{19}$, Z$^{20}$ and Z$^{21}$ are independently a single bond, —CH$_2$CH$_2$—, —CH═CH—, —C≡C— or —COO—.

12. The liquid crystal composition according to claim 9, further containing at least one compound selected from the group of compounds represented by formulas (2) to (4):

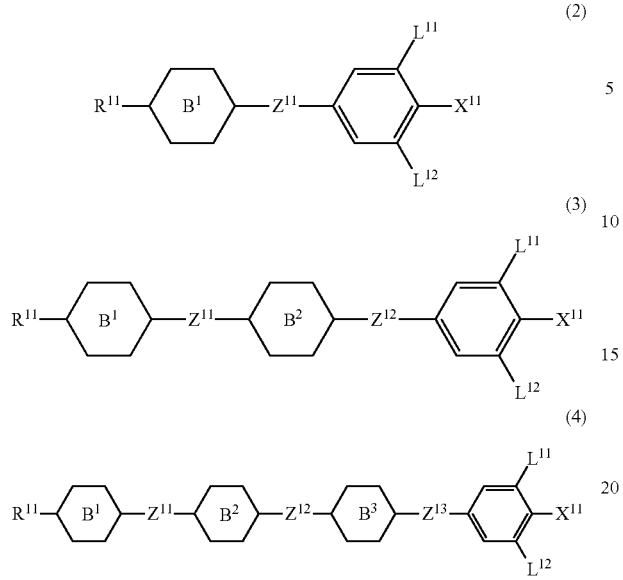

wherein in formulas (2) to (4), $R^{11}$ is alkyl having 1 to 10 carbons or alkenyl having 2 to 10 carbons, and in the alkyl and the alkenyl, at least one piece of hydrogen may be replaced by fluorine, and at least one piece of —$CH_2$— may be replaced by —O—;

$X^{11}$ is fluorine, chlorine, —$OCF_3$, —$OCHF_2$, —$CF_3$, —$CHF_2$, —$CH_2F$, —$OCF_2CHF_2$ or —$OCF_2CHFCF_3$;

ring $B^1$, ring $B^2$ and ring $B^3$ are independently 1,4-cyclohexylene, 1,4-phenylene in which at least one piece of hydrogen may be replaced by fluorine, tetrahydropyran-2,5-diyl, 1,3-dioxane-2,5-diyl, or pyrimidine-2,5-diyl;

$Z^{11}$, $Z^{12}$ and $Z^{13}$ are independently a single bond, —$CH_2CH_2$—, —CH=CH—, —C≡C—, —COO—, —$CF_2O$—, —$OCF_2$—, —$CH_2O$— or —$(CH_2)_4$—; and $L^{11}$ and $L^{12}$ are independently hydrogen or fluorine.

13. The liquid crystal composition according to claim 9, further containing at least one optically active compound and/or at least one polymerizable compound.

14. The liquid crystal composition according to claim 9, further containing at least one antioxidant and/or at least one ultraviolet light absorbent.

15. A liquid crystal display device, including the liquid crystal composition according to claim 9.

16. A liquid crystal display device, wherein the liquid crystal composition according to claim 9 is encapsulated.

* * * * *